United States Patent
Patel et al.

(10) Patent No.: US 12,202,903 B2
(45) Date of Patent: Jan. 21, 2025

(54) HUMANISED ANTI-IL17BR ANTIBODY

(71) Applicant: LIFEARC, Greater London (GB)

(72) Inventors: Seema Patel, Greater London (GB); David Matthews, Greater London (GB)

(73) Assignee: LIFEARC, Greater London (GB)

( * ) Notice: Subject to any disclaimer, the term of this patent is extended or adjusted under 35 U.S.C. 154(b) by 904 days.

(21) Appl. No.: 17/299,212

(22) PCT Filed: Dec. 6, 2019

(86) PCT No.: PCT/EP2019/084083
§ 371 (c)(1),
(2) Date: Jun. 2, 2021

(87) PCT Pub. No.: WO2020/115319
PCT Pub. Date: Jun. 11, 2020

(65) Prior Publication Data
US 2022/0041740 A1    Feb. 10, 2022

(30) Foreign Application Priority Data

Dec. 7, 2018 (GB) .................................. 1820006

(51) Int. Cl.
C07K 16/28 (2006.01)
A61K 39/00 (2006.01)

(52) U.S. Cl.
CPC ........... C07K 16/2866 (2013.01); A61K 39/001119 (2018.08); *C07K 2317/24* (2013.01); *C07K 2317/92* (2013.01); *C07K 2317/94* (2013.01)

(58) Field of Classification Search
CPC ............. C07K 16/2866; C07K 2317/24
See application file for complete search history.

(56) References Cited

U.S. PATENT DOCUMENTS

| 8,852,589 B2 * | 10/2014 | McKenzie ............. A61P 1/04 424/139.1 |
| 2010/0266531 A1 | 10/2010 | Hsieh et al. |
| 2018/0237529 A1 | 8/2018 | Back et al. |

FOREIGN PATENT DOCUMENTS

| CN | 1341660 A | 9/2002 |
| CN | 1997667 A | 7/2007 |
| WO | WO2006004663 A | 1/2006 |
| WO | WO2010116123 | 10/2010 |
| WO | WO2013053021 A | 4/2013 |
| WO | WO2016180721 A | 11/2016 |
| WO | WO2018183889 | 10/2018 |

OTHER PUBLICATIONS

Almagro et. al., Front. Immunol. 2018; 8:1751 (Year: 2018).*
Reichert & Valge-Archer, Nat. Rev. Drug Disc. 2007; 6:349-356 (Year: 2007).*
Chan and Carter, Nature Reviews Immunology, 2010; 10:301-316 (Year: 2010).*
HogenEsch and Nikitin, J Control Release, 10:183-186 (2012) (Year: 2012).*
Aalberse et al. (2002) "IgG4 breaking the rules", Immunology, vol. 105, No. 1, pp. 9-19.
Camel0 et al. (2012) "Blocking IL-25 signaling protects against gut inflammation in a type-2 model of colitis by suppressing nuocyte and NKT derived IL-13", J0urnal 0f Gastroenterol0gy, vol. 47, No. 11, pp. 1198-1211.
Desai et al. (2011) "Differential expression of monocyte/macrophage-selective markers in human idiopathic pulmonary fibrosis", Experimental Lung Research, Taylor & Francis Group, UK, vol. 37, No. pp. 227-238.
Laprevotte et al. (2017) "The IL-17B-IL-17 receptor B pathway promotes resistance 1 paclitaxel in breast tumors through activation of the ERKI/2 pathway", Oncotarget, vol. 8, No. 69, pp. 113360-113372.
Wu et al. (2015) "Targeting IL-17B-IL-17RB signaling with an anti-IL-17RB antibody blocks pancreatic cancer metastasis by silencing multiple chemokines", J. Exp. Med, vol. 212, No. 3 pp. 333-349.
Tang, et al. (2016) "Allergen-induced increases in interleukin-25 and interleukin-25 receptor expression in mature eosinophils from atopic asthmatics." *International archives of allergy and immunology* 170(4): 234-242.
Gurezynski, et al.(2018) "IL-17 in the lung: the good, the bad, and the ugly" *Am J Physiol Lung Cell Mol Physiol*, 314: L6-L6.

* cited by examiner

*Primary Examiner* — Jessica H Roark
*Assistant Examiner* — Francesca Edgingtongiordano
(74) *Attorney, Agent, or Firm* — Pamela J. Sherwood; Bozicevic, Filed & Francis LLP

(57) ABSTRACT

This invention relates to humanised versions of the murine anti-IL17BR antibody D9.2 which comprise mutations of certain residues within the heavy chain and/or light chain variable domains that display improved expression without deleterious effects on specificity or affinity. The humanised antibodies may comprise a heavy chain variable (VH) domain which comprises a VHCDR1 of SEQ ID NO: 1, a VHCDR2 of SEQ ID NO: 2, and a VHCDR3 of SEQ ID NO: 3, for example, a VH domain of SEQ ID NO: 9, SEQ ID NO: 10 or SEQ ID NO: 11. The humanised antibodies may comprise a light chain variable (VL) domain which comprises a VLCDR1 of SEQ ID NO: 4, a VLCDR2 of SEQ ID NO: 5, and a VLCDR3 of SEQ ID NO: 6, for example a VL domain of SEQ ID NO: 13. Antibodies, pharmaceutical compositions and methods of use, for example in the treatment of cancer are provided.

21 Claims, 26 Drawing Sheets
Specification includes a Sequence Listing.

| Human IL-17BR | ka (1/Ms) | kd (1/s) | KD (pM) |
|---|---|---|---|
| cD9001 | 2.90E+06 | 5.00E-05 | 17 |
| hD9040 | 3.42E+06 | 6.66E-05 | 20 |
| hD9041 | 3.89E+06 | 4.44E-05 | 11 |
| hD9042 | 4.85E+06 | 8.23E-05 | 17 |

FIGURE 5 CONTINUED

HUMANISED ANTI-IL17BR ANTIBODY

FIELD

The present invention relates to humanised antibodies that bind interleukin-17 receptor B (IL17BR).

BACKGROUND

IL-17B receptors (IL-25 receptors) are expressed on innate lymphoid cells (ILC2s), which serve an important role in the initiation of type-2 immune responses and have recently been linked to complex roles in the transition from innate to adaptive immunity. ILC2s provide a critical source of type-2 cytokines, which in turn stimulate the effector response leading to inflammation.

The murine anti-IL17BR antibody D9.2 was initially raised against a murine IL-17Br/Fc fusion protein (Neill D R, et al. Nature. 2010 464:1367-1370; U.S. Pat. No. 8,852,589) and has been shown to slow ongoing inflammation in colitis models (Camelo et al J Gastroenterol. 2012 47(11): 1198-1211)

Humanised versions of D9.2 would be useful for clinical applications, for example in the treatment of allergic and inflammatory conditions, such as colitis.

SUMMARY

The present inventors have unexpectedly discovered that the expression of humanised versions of the D9.2 murine anti-IL17BR antibody is improved without reducing specificity or affinity by mutation of certain residues within the, heavy chain and/or light chain variable domains. This may be useful for example in development candidate molecules for clinical use.

A first aspect of the invention provides a humanised antibody molecule comprising a heavy chain variable domain and a light chain variable domain, wherein
 a) the heavy chain variable domain (VH) comprises a VHCDR1 of SEQ ID NO: 1, a VHCDR2 of SEQ ID NO: 2, and a VHCDR3 of SEQ ID NO: 3, and
 b) the light chain variable domain (VL domain) comprises a VLCDR1 of SEQ ID NO: 4, a VLCDR2 of SEQ ID NO: 5, and a VLCDR3 of SEQ ID NO: 6.

The antibody molecule may specifically bind to interleukin-17 receptor B (IL17BR), preferably the extracellular domain of IL17BR.

An antibody molecule of the first aspect may comprise the VH domain of SEQ ID NO: 8, optionally with up to four additional framework substitutions. For example, the antibody may comprise a VH domain of SEQ ID NO: 9, SEQ ID NO: 10 or SEQ ID NO: 11, optionally with up to four additional framework substitutions. An antibody of the first aspect may comprise the VL domain of SEQ ID NO: 13, optionally with up to four additional framework substitutions.

In some preferred embodiments, an antibody molecule of the first aspect may comprise the VH domain of SEQ ID NO: 9 and the VL domain of SEQ ID NO: 13.

A second aspect described herein provides a pharmaceutical composition comprising an antibody molecule of the first aspect and a pharmaceutically acceptable carrier.

A third aspect described herein provides a nucleic acid encoding an antibody molecule of the first aspect or a heavy chain variable domain and/or light chain variable domain thereof.

A fourth aspect described herein provides a vector comprising a nucleic acid of the third aspect.

A fifth aspect described herein provides a host cell comprising a nucleic acid of the third aspect or a vector of the fourth aspect.

A sixth aspect described herein provides a method for making an antibody molecule according to the first aspect the method comprising expressing, in a host cell culture, a vector according to the fourth aspect to produce said antibody; and recovering the antibody molecule from the cell culture.

A seventh aspect described herein provides a method of treatment of an allergic or inflammatory condition by administering, to an individual in need of treatment, an effective amount of an antibody molecule according to the first aspect or the pharmaceutical composition according to the second aspect.

An eighth aspect described herein provides an antibody molecule according to the first aspect or the pharmaceutical composition according to the second aspect, for use as a medicament or for use in a method of treatment of the human or animal body.

A ninth aspect described herein provides an antibody molecule according to the first aspect or the pharmaceutical composition according to the second aspect, for use in a method of treatment of an allergic or inflammatory condition or a cancer condition in an individual.

These and other aspects and embodiments described herein are described in more detail below.

DETAILED DESCRIPTION

Figure 1:
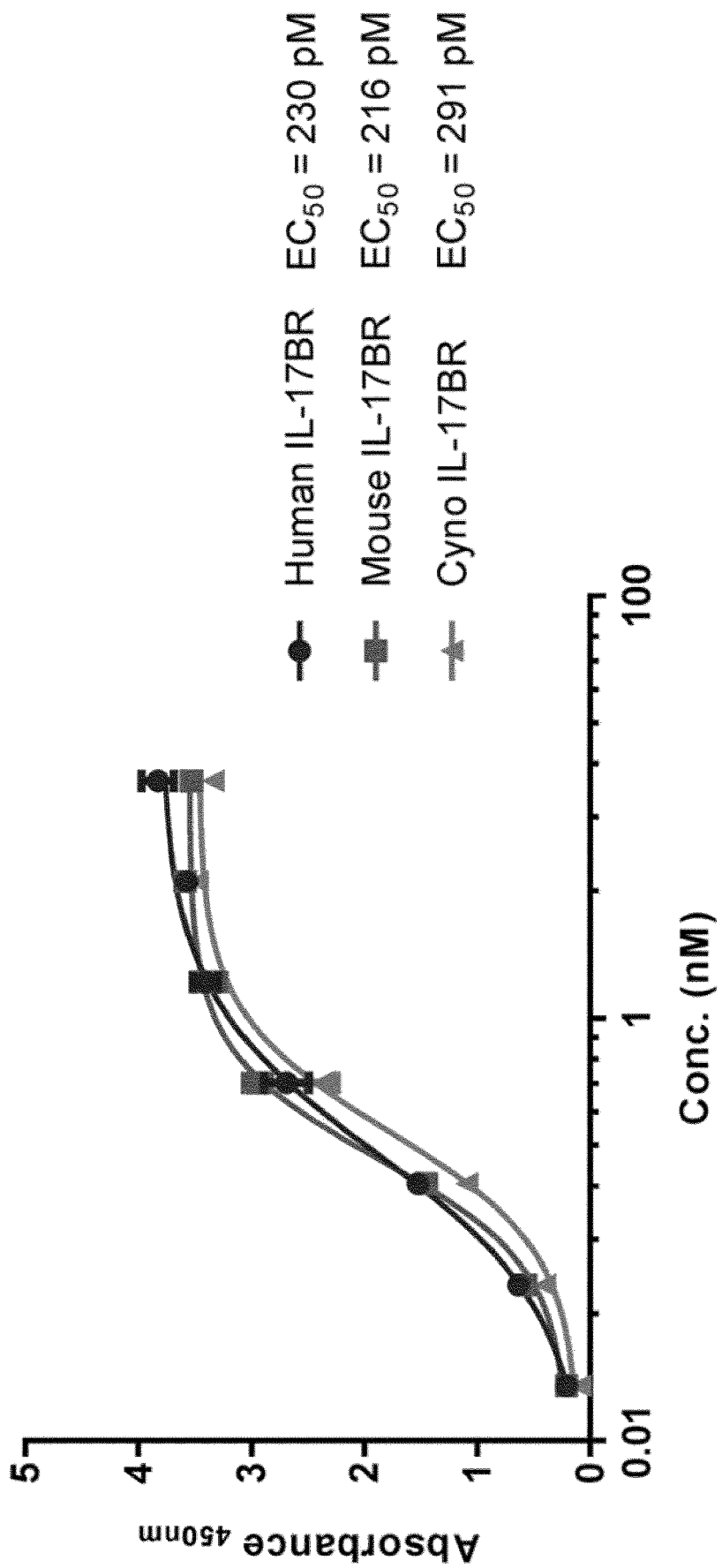
FIG. 1 shows the binding of chimeric cD9001 antibody to Human, Mouse and Cynomolgus monkey to IL-17BR.

This invention relates to the finding that the expression of humanised versions of the murine anti-IL17BR antibody D9.2 is significantly improved without deleterious effects on specificity or affinity by the mutation of certain residues within the variable domains.

An antibody molecule described herein may specifically bind to interleukin-17 receptor B (IL17BR). Preferably, an antibody molecule described herein specifically binds to the extracellular domain of IL17BR (residues 18 to 292 of human IL17BR).

An antibody molecule described herein may bind human IL17BR, mouse IL17BR and/or cynomolgus IL17BR. For example, an antibody molecule may bind human IL17BR and show no binding or substantially no binding to mouse IL17BR and/or cynomolgus IL17BR. Preferably, antibody molecules of the invention are cross reactive with human, mouse and cynomolgus IL17BR. For example, a cross reactive antibody molecule may bind human IL17BR, mouse IL17BR and cynomolgus IL17BR. Typically, specificity may be determined by means of a binding assay such as ELISA employing a panel of antigens.

An antibody molecule described herein will generally be specific for IL17BR. In other words, an antibody molecule may bind IL17BR but show no binding or substantially no binding to other members of the IL-17R family. Preferably, an antibody molecule specific for IL17BR binds IL17BR but shows no binding or substantially no binding to IL-17RA, IL-17RC and/or IL-17RD.

The interleukin-17B receptor, variously known as IL-25R, IL17BR, IL-17RB or IL-17RH1 was first identified in an expressed sequence tag database by its homology to the IL-17A receptor (IL-17RA) (Tian et al., 2000 Oncogene 19, 2098-2109). IL17BR has subsequently been shown to bind both IL17B and IL25 (Lee, J., et al., *J Biol Chem* 276, 1660-1664 (2001); Shi, Y., et al., *J Biol Chem* 275, 19167-19176 (2000); Tian et al., 2000 supra). IL25 binds to IL17BR with a stronger affinity (1.4 nM) than IL-17B (7.6 nM). Murine IL17BR (Gene ID 50905: Nucleic acid: NM_019583.3 GI: 142368701; NP_062529.2 GI: 83025064) is described by Tian et al., 2000 supra. Human IL17BR (Gene ID: 55540, Nucleic acid: NM_018725.3 GI: 112382255; Protein NP_061195.2 GI: 27477074) is described by Shi, Y., et al., 2000 supra.

IL17BR is available from commercial sources (e.g. R&D Systems, MN, USA) as an Fc-fusion protein, or may be cloned or synthesised using the sequences of IL17BR available in the art. For production of antibodies or use in immunoassays, fragments of recombinant IL17BR may be used, particularly those containing the extracellular domain (e.g. residues 18 to 292 of the human IL17BR sequence of NP_061195.2).

Preferably, an antibody molecule as described herein inhibits or blocks the binding or functional interaction of IL17BR with a ligand, such as IL25 or IL17B. For example, an antibody molecule may inhibit the functional interaction of IL17BR and IL25 and/or may block the binding of IL17BR to IL17B.

Preferably, an antibody molecule as described herein reduces or inhibits at least one of IL-25-mediated airway hyperreactivity (AHR); IL-13 production; IL-25-mediated IL-5 production; IL-25-mediated IL-8 production; and γδT cell expansion and infiltration.

In some embodiments, binding of an antibody molecule described herein with IL17BR may be abolished by competition with recombinant ligand, such as IL25 or IL17B.

An anti-IL17BR antibody as described herein may comprise a heavy chain variable (VH) domain and a light chain variable (VL) domain. The VH domain may comprise the VHCDR1, VHCDR2 and VHCDR3 sequences of SEQ ID NOs 1 to 3, respectively. In some embodiments, the VHCDR2 may have the sequence of SEQ ID NO: 14 or SEQ ID NO: 15. The VL domain may comprise the VLCDR1, VLCDR2 and VLCDR3 sequences of SEQ ID NOs 4 to 6, respectively.

In some embodiments, the VH domain of an antibody molecule described herein may comprise the amino acid sequence of SEQ ID NO: 7 with a T to R substitution at Kabat position 94 and optionally substitutions at one, two, three, four, five or all six of Kabat positions 1, 24, 60, 64, 65 and 69, optionally with 1, 2, 3 or 4 further substitutions in the framework regions. For example, the VH domain of an antibody molecule described herein may comprise the amino acid sequence of SEQ ID NO: 7 with N60A, K64Q, D65G, and T94R substitutions or with E1Q, T24A, L69M and T94R substitutions (Kabat numbered), and optionally 1, 2, 3 or 4 further substitutions in the framework regions.

The VH domain of an antibody molecule described herein may comprise the amino acid sequence of SEQ ID NO: 8; or the amino acid sequence of SEQ ID NO: 8 with independently 1 or more, for example 2, 3, or 4 or more amino acid substitutions, deletions or insertions in the framework regions. The substitutions may be conservative substitutions. For example, an anti-IL17BR antibody described herein may comprise a VH domain of SEQ ID NO: 9, 10 or 11, optionally with 1, 2, 3 or 4 amino acid substitutions in the framework regions.

In some embodiments, the VL domain of an antibody molecule described herein may comprise the amino acid sequence of SEQ ID NO: 12 with an R to G substitution at Kabat position 93 and optionally with 1, 2, 3 or 4 additional amino acid substitutions in the framework regions.

The VL domain of an antibody molecule described herein may have the amino acid sequences of SEQ ID NO: 13; or may have the amino acid sequences of SEQ ID NO: 13 with independently 1 or more, for example 2, 3, or 4 or more amino acid substitutions, deletions or insertions in the framework regions. The substitutions may be conservative substitutions. For example, an anti-IL17BR antibody described herein may comprise a VL domain of SEQ ID NO: 13, optionally with 1, 2, 3 or 4 amino acid substitutions in the framework regions.

A suitable anti-IL17BR antibody may comprise (i) the VH domain of SEQ ID NO: 9 and the VL domain of SEQ ID NO: 13, (ii) the VH domain of SEQ ID NO: 10 and the VL domain of SEQ ID NO: 13, or (iii) the VH domain of SEQ ID NO: 11 and the VL domain of SEQ ID NO: 13. Some preferred anti-IL17BR antibodies may comprise the VH domain of SEQ ID NO: 9 and the VL domain of SEQ ID NO: 13.

The terms "immunoglobulin" and "antibody" may be used interchangeably to refer to any protein comprising an antibody antigen-binding site which has the ability to specifically bind one or more antigens.

An "antigen" is an entity (e.g., a proteinaceous entity or peptide) to which an immunoglobulin or antibody (or antigen-binding fragment thereof) specifically binds. The antigens of an anti-IL17BR antibody described herein may include IL17BR or fragments thereof, for example fragments comprising the extracellular domain of IL17BR or immunogenic portions thereof.

Native antibodies are usually heterotetrameric glycoproteins of about 150,000 Daltons, composed of two identical light (L) chains and two identical heavy (H) chains. Each light chain is linked to a heavy chain by one covalent disulphide bond, with varying numbers of disulphide linkages between the heavy chains of different antibody isotypes. Each heavy and light chain also has regularly spaced intra-chain disulphide bridges.

Antibodies comprise globular regions of heavy or light chain polypeptides called "domains". A domain may comprise peptide loops, usually 3 to 4 loops, which are stabilized, for example, by β-pleated sheet and/or intra-chain disulphide bonding. Domains are generally referred to as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions".

The "constant" domains of an antibody light chain may be referred to as "light chain constant regions", "light chain constant domains", "CL" regions or "CL" domains. The "constant" domains of an antibody heavy chain may be referred to as "heavy chain constant regions", "heavy chain constant domains", "CH" regions or "CH" domains. The constant domain of the light chain is aligned with the first constant domain of the heavy chain.

The constant domain of the heavy chain which comprises the tail region of the antibody is referred to herein as the Fc (fragment crystallizable) domain or Fc region. The Fc region may interact with cell surface Fc receptors and some proteins of the complement system, by which method the antibody may activate the immune system. The Fc regions contain three heavy chain constant domains in each polypeptide chain.

In some embodiments, the VH domain of an antibody molecule described herein may be fused to an antibody constant region, for example, an IgG4 constant region, such as SEQ ID NO: 16. The amino acid sequence of the VH domain fused to the IgG4 constant region may comprise SEQ ID NO: 17.

The "variable" domains of an antibody light chain may be referred to as "light chain variable regions", "light chain variable domains", "VL" regions or "VL" domains (the I' here referring to 'light' rather than the light chain isotype 'lambda'). The "variable" domains of an antibody heavy chain may be referred to as "heavy chain variable regions", "heavy chain variable domains", "VH" regions or "VH" domains. Intact light chains have, for example, two domains (VL and CL) and intact heavy chains have, for example, four or five domains (VH, CH1, CH2, and CH3).

Light and heavy chain variable domains include "hypervariable regions" (HVR or HV), also known as "complementarity determining regions" (CDRs), which are hypervariable in sequence and may form structurally defined loops. Generally, antibodies comprise six hypervariable regions; three in the heavy chain (H1, H2, H3) and three in the light chain (L1, L2, L3) interspersed among relatively conserved framework regions (FRs). In antibodies described herein, the amino acid sequences of the variable domains are shown below. The CDRs may be readily identified in these sequences using standard techniques.

The variable regions of each light/heavy chain pair form the antigen binding site. The term "antigen binding site" refers to a site that specifically binds (immunoreacts with) an antigen. Antibodies described herein comprise at least one antigen binding site, preferably comprising two antigen binding sites. An antigen binding site is formed from the heavy and light chain CDRs, aligned by the framework regions, which enable binding to a specific epitope. An "antigen binding region" or "antigen binding domain" is an antibody region or domain that includes an antibody binding site. Antibodies described herein have at least one antigen binding site which recognizes IL17BR.

Naturally-occurring antibody chains or recombinantly-produced antibody chains may be expressed with a leader sequence which is removed during cellular processing to produce a mature chain. Mature chains may also be produced recombinantly, containing a non-naturally occurring leader sequence, for example, to enhance secretion or alter the processing of a particular chain of interest.

The constant regions of the heavy and light chains of an antibody may display phenotypic variation. Antibody light chains are classified as either kappa (κ) or lambda (λ) based on the amino acid sequence of the light chain constant region, and are about 230 residues in length. An antibody described herein comprises a kappa light chain (the variable domain of the kappa light chain is referred to herein as VK). Heavy chains from humans and higher mammals are classified as gamma (γ), mu (μ), alpha (α), delta (δ), or epsilon (ε), are about 450-600 residues in length, and define the antibody's isotype as IgG, IgM, IgA, IgD and IgE, respectively. There are two subclasses of IgM (H and L), three subclasses of IgA (IgA1, IgA2, and secretory IgA), and four subclasses of IgG (IgG1, IgG2, IgG3, and IgG4). An antibody described herein is preferably an immunoglobulin G (IgG) antibody, most preferably an IgG1 antibody.

The antibodies described herein may comprise heavy chains which belong to any of the immunoglobulin isotypes described herein. The antibodies described herein may comprise sequences from more than one class or isotype.

An anti-IL17BR antibody described herein may exhibit cytotoxic activity. In such an antibody, the constant domain is usually a complement fixing constant domain and the class is typically IgG1. Human isotypes IgG1 and IgG4 are exemplary.

An antibody molecule described herein may comprise a fragment of a whole antibody. The term "fragment" refers to a part or portion of an antibody or antibody chain comprising fewer amino acid residues than an intact or complete antibody or antibody chain, wherein the portion preferably retains at least one, preferably most or all, of the functions normally associated with that portion when present in an intact antibody. Fragments may be obtained via chemical or enzymatic treatment of an intact or complete antibody or antibody chain. Fragments may also be obtained by recombinant means.

Fragments of the antibodies described herein may bind antigen or compete with intact antibody (i.e., with the intact antibody from which they were derived) for antigen binding (i.e., specific binding). Antibodies described herein bind to IL17BR. Binding fragments are produced by recombinant DNA techniques, or by enzymatic or chemical cleavage of intact immunoglobulins.

Antibodies described herein may exist as binding fragments including, but not limited to, Fab, Fab', F(ab')$_2$, chemically linked F(ab')₂, monospecific Fab₂, bispecific Fab₂, trispecific Fab₂, monovalent IgG, scFv (single-chain variable fragment), di-scFv (divalent scFv), bispecific diabody, trispecific triabody, scFv-Fc, minibody or sdAb (single domain antibody), and retain the ability to bind IL17BR.

An antibody molecule described herein may be part of a bispecific or trispecific antibody. A bispecific antibody is an artificial hybrid antibody having two different heavy/light chain pairs and two different antigen-binding sites; a trispecific antibody is an artificial hybrid antibody having three different heavy/light chain pairs and three different antigen-binding sites. Bispecific and trispecific antibodies may be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). An exemplary antibody described herein may be a bispecific antibody comprising at least two different antigen binding sites.

Specific binding refers to the situation in which an antibody binds to an epitope on an antigen and will not show any significant binding to molecules other than the specific epitope on the antigen. The term is also applicable where e.g. an antigen binding domain is specific for an epitope which is carried by a number of antigens, in which case the antibody carrying the antigen binding domain will be able to bind to the various antigens carrying the epitope.

Anti-IL17BR antibody molecules described herein, or nucleic acids encoding such antibody molecules, will be in an isolated state. Antibody molecules and nucleic acids will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Antibody molecules and nucleic acid may be formulated with diluents or adjuvants and still for practical purposes be isolated—for example the antibodies will normally be mixed with gelatin or other carriers if used to coat microtitre plates for use in immunoassays, or will be mixed with pharmaceutically acceptable carriers or diluents when used in diagnosis or therapy.

Another aspect of the invention provides a nucleic acid which encodes an antibody or a light chain, heavy chain, VH domain or VL domain thereof, as disclosed herein. A nucleic acid may, for example, encode a heavy chain variable domain (VH domain) comprising SEQ ID NO: 8, for example a VH domain comprising SEQ ID NO: 9, SEQ ID NO: 10 or SEQ ID NO: 11 and/or a light chain variable domain (VL domain) comprising SEQ ID NO: 13, as described above. Optionally, the encoded VH domain and/or VL domain may have up to four additional amino acid mutations in the framework region.

The nucleic acids may include DNA and RNA sequences, wherein the thymine nucleobases are substituted with uracil.

Production of the anti-IL17BR antibody molecule described herein may be carried out by any suitable technique including techniques described herein as well as other techniques known in the art. Antibodies described herein may be produced on a commercial scale using methods that are well-established in the art for large scale manufacturing of antibodies. For example, recombinant expression systems such as those described herein may be employed.

An antibody molecule described herein may be produced by recombinant expression. Nucleic acids as described above, encoding light and heavy chain variable regions optionally linked to constant regions, may be inserted into expression vectors. Vectors which comprise nucleic acids encoding antibodies described herein are themselves an aspect of the invention. The light and heavy chains may be cloned in the same or different expression vectors. The nucleic acids encoding the antibody chains described herein may be operably linked to one or more control sequences in the expression vector(s) that ensure the expression of the antibody chains. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells (e.g., COS, CHO, or Expi293 cells). Such vectors may be incorporated into an appropriate host, whereby the host is maintained under conditions suitable for high level expression of the nucleotide sequences, and the collection and purification of the antibodies.

Aspects of the invention provide a nucleic acid encoding an anti-IL17BR antibody molecule described herein or a VH or VL domain thereof; a vector, preferably an expression vector, comprising one or more nucleic acids that encode an antibody described herein; and a vector comprising one or more nucleic acids that encode an antibody molecule described herein or a VH or VL domain thereof, operably linked to a promoter. Exemplary expression vectors are pHuK and pHuG1 which, in combination with the nucleic acids disclosed herein, comprise nucleotide sequences encoding the antibodies described herein. Other vectors which provide nucleotide sequences encoding the constant regions of antibody light and heavy chains may also be used.

The expression vectors for use as described herein are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g. U.S. Pat. No. 4,704,362).

A vector described herein for use in a eukaryotic host cell may also encode a signal sequence or other polypeptide having a specific cleavage site at the N-terminus of the mature antibody chain or polypeptide. Suitable signal sequences may be heterologous and may be recognized and processed (i.e., cleaved by a signal peptidase) by the host cell. In mammalian cell expression, mammalian signal sequences as well as viral secretory leaders, for example, the herpes simplex gD signal, are available.

Alternatively, antibody-coding sequences described herein may be incorporated in transgenes for introduction into the genome of a transgenic animal and subsequent expression in the milk of the transgenic animal (see, e.g., U.S. Pat. Nos. 5,741,957, 5,304,489, and 5,849,992). Suitable transgenes include coding sequences for light and/or heavy chains in operable linkage with a promoter and enhancer from a mammary gland specific gene, such as casein or β lactoglobulin.

Vectors described herein containing the polynucleotide sequences of interest (e.g., the heavy and light chain encoding sequences and expression control sequences) may be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Green and Sambrook, Molecular Cloning: A Laboratory Manual (Cold Spring Harbor Press, 4th ed., 2012). Other methods used to transform mammalian cells include the use of polybrene, protoplast fusion, liposomes, electroporation, and microinjection (see generally, Sambrook et al., supra). For production of transgenic animals, transgenes may be microinjected into fertilized oocytes, or may be incorporated into the genome of embryonic stem cells, and the nuclei of such cells transferred into enucleated oocytes.

Host cells may be transformed with the expression vectors and cultured in conventional nutrient media as appropriate for inducing promoters, selecting transformants, and/or amplifying the genes encoding the required sequences. A host cell comprising a nucleic acid or vector described above is provided as an aspect of the invention.

Another aspect of the invention provides a method for making an anti-IL17BR antibody molecule described herein, the method comprising expressing, in a host cell culture, a vector described herein to produce said antibody, and recovering the antibody from the cell culture. This method may comprise transferring a vector comprising one or more nucleic acids encoding an anti-IL17BR antibody molecule or antibody chains thereof, as described above, into a host cell, as described herein, growing the host cell culture under conditions which allow for expression of the nucleic acid(s) and recovering the expressed anti-IL17BR antibody molecule. Any suitable method known in the art may be employed.

Microbial host organisms suitable for use in cloning and expressing the nucleic acids and vectors described herein include prokaryotic hosts; *Escherichia coli*, bacilli, such as *Bacillus subtilis*, and other enterobacteriaceae, such as *Salmonella, Serratia*, and various *Pseudomonas* species. In these prokaryotic hosts, one may also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation. Vectors for use in prokaryotic cells may also require an origin of replication component.

Other microbes, such as yeast, may also be used to express the nucleic acids or vectors described herein. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express the nucleic acids or vectors described herein and produce the antibody polypeptides (e.g., polynucleotides encoding antibodies or fragments thereof (see e.g., Winnacker, From Genes to Clones, VCH Publishers, N.Y. 1987). A eukaryotic or mammalian cell host comprising a nucleic acid or vector described herein is itself an aspect of the invention. Eukaryotic cells are actually preferred, because a number of suitable host cell lines capable of secreting heterologous proteins (e.g., intact antibodies) have been developed in the art, and include CHO cell lines, various COS cell lines, HeLa cells, Expi293 cells, ExpiCHO cells, myeloma cell lines, or transformed B-cells or hybridomas. The cells may be human or non-human e.g. non-human mammalian cells. In some preferred embodiments, the cells are Expi293 human cells. The antibodies described herein may be produced in cell lines engineered to produce afucosylated proteins, such as the Potelligent® CHOK1SV cell line (BioWa/Lonza), GlymaxX®-engineered cells (ProBioGen) or the duck embryonic stem cell line EB66 (Valneva). Expression vectors for mammalian cells generally include, but are not limited to, one or more of the following: a signal sequence, one or more marker genes, an enhancer element, a promoter, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like (see for example Co et al., J. Immunol. 148:1149 1992).

When heavy and light chains are cloned on separate expression vectors, the vectors are co-transfected to obtain expression and assembly of intact antibodies described herein. Once expressed, the whole antibodies, their dimers, individual light and heavy chains, or other immunoglobulin forms described herein may be purified according to standard procedures of the art, including ammonium sulphate precipitation, affinity columns, column chromatography, HPLC purification, gel electrophoresis and the like (see generally Scopes, Protein Purification (Springer-Verlag, N.Y., (1982)). Substantially pure anti-IL17BR antibody molecule of at least about 90 to 95% homogeneity are preferred, and 98 to 99% or more homogeneity are most preferred, for pharmaceutical uses as described herein. Standard protein purification methods known in the art may be employed. The following procedures are exemplary of suitable protein purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulphate precipitation, and gel filtration.

An anti-IL17BR antibody molecule described herein may specifically bind to human IL17BR. An antibody described herein may also display the desirable structural, physical, biophysical and chemical properties described below, and with reference to the examples.

The affinity of an anti-IL17BR antibody molecule described herein is the extent or strength of binding of antibody to epitope or antigen. The dissociation constant, $K_D$, and the affinity constant, $K_A$, are quantitative measures of affinity. $K_D$ is the ratio of the antibody dissociation rate ($k_{off}$), how quickly it dissociates from its antigen, to the antibody association rate ($k_{on}$) of the antibody, how quickly it binds to its antigen. The binding of an antibody to its antigen is a reversible process, and the rate of the binding reaction is proportional to the concentrations of the reactants. At equilibrium, the rate of [antibody][antigen] complex formation is equal to the rate of dissociation into its components [antibody]+[antigen]. The measurement of the reaction rate constants may be used to define an equilibrium or affinity constant, $K_A$ ($K_A=1/K_D$). The smaller the $K_D$ value, the greater the affinity of the antibody for its target. Most antibodies have $K_D$ values in the low micromolar ($10^{-6}$) to nanomolar ($10^{-7}$ to $10^{-9}$) range. High affinity antibodies are generally considered to be in the low nanomolar range ($10^{-9}$) with very high affinity antibodies being in the picomolar ($10^{-12}$) range.

An anti-IL17BR antibody molecule described herein may have an association rate constant ($k_{on}$) of at least $2\times10^2$ $M^{-1}s^{-1}$, at least $5\times10^2$ $M^{-1}s^{-1}$, at least $10^3$ $M^{-1}s^{-1}$, or at least $5\times10^3$ $M^{-1}s^{-1}$, at least $10^4$ $M^{-1}s^{-1}$, at least $5\times10^4$ $M^{-1}s^{-1}$, at least $10^5$ $M^{-1}s^{-1}$, at least $5\times10^5$ $M^{-1}s^{-1}$, or at least $10^6$ $M^{-1}s^{-1}$. For example, anti-IL17BR antibody molecule may have an association rate of $3\times10^6$ $M^{-1}s^{-1}$ to $5\times10^6$ $M^{-1}s^{-1}$ An anti-IL17BR antibody molecule described herein may have an antibody dissociation ($k_{off}$) rate of less than $5\times10^{-1}$ $s^{-1}$, less than $10^{-1}$ $s^{-1}$, less than $5\times10^{-2}$ $s^{-1}$, less than $10^{-2}$ $s^{-1}$, or less than $5\times10^{-3}$ $s^{-1}$, less than $10^{-3}$ $s^{-1}$, less than $5\times10^{-4}$ $s^{-1}$, less than $10^{-4}$ $s^{-1}$ or less than $5\times10^{-5}$ $s^{-1}$. For example, anti-IL17BR antibody molecule may have a dissociation rate of $6\times10^{-5}$ $s^{-1}$ to $9\times10^{-5}$ $s^{-1}$.

In some embodiments, an anti-IL17BR antibody molecule described herein may bind to IL17BR with an equilibrium association constant or $K_A$ of $5\times10^6 M^{-1}$ or more, $10^6 M^{-1}$ or more, $5\times10^7 M^{-1}$ or more, $10^7$ $M^{-1}$ or more, $5\times10^8$ $M^{-1}$, $10^{-8}$ $M^{-1}$ or more, $5\times10^9$ $M^{-1}$ or more, $10^9$ $M^{-1}$ or more, $5\times10^{10}$ $M^{-1}$ or more, $10^{10}$ $M^{-1}$ or more, or $5\times10^{11}$ $M^{-1}$ or more. An anti-IL17BR antibody molecule as described herein may bind IL17BR with an affinity which is substantially similar to that of D9.2, e.g. 90% to 110% of the binding affinity of D9.2.

An anti-IL17BR antibody molecule described herein may have an equilibrium dissociation constant or $K_D$ from IL17BR of less than $5\times10^{-6}$M, less than $10^{-6}$M, less than $5\times10^{-7}$M, less than $10^{-7}$M less than $5\times10^{-8}$M, less than $10^{-8}$M, less than $5\times10^{-9}$M, less than $10^{-9}$M, less than $5\times10^{-10}$M, less than $10^{-10}$M, or less than $5\times10^{-11}$M. For example, anti-IL17BR antibody molecule may have an equilibrium dissociation constant or $K_D$ of $1\times10^{-11}$ M to $2\times10^{-11}$ M.

Specific binding of an anti-IL17BR antibody molecule means that the antibody exhibits appreciable affinity for a particular antigen or epitope and, generally, does not exhibit significant cross-reactivity. An antibody that "does not exhibit significant cross-reactivity" is one that will not appreciably bind to an undesirable entity (e.g., an undesirable proteinaceous entity). An antibody specific for a particular epitope will, for example, not significantly cross-react with remote epitopes on the same protein or peptide. Specific binding i.e., $k_{off}$, $k_{on}$, $K_A$ and $K_D$, of an antibody described herein may be determined according to any art-recognized means for determining such binding.

An anti-IL17BR antibody molecule described herein may be thermally stable, i.e., an antibody described herein may bind to IL17BR at temperatures between 30° C. and 85° C., specifically up to 75° C. An antibody described herein may have a melting temperature of between 50° C. and 100° C., specifically between 60 and 80° C., more specifically near 66-67° C.

An anti-IL17BR antibody molecule described herein may have a low propensity for aggregation. The propensity for aggregation may be analysed using standard techniques, such as multi-angle light scattering, or dynamic light scattering as described herein. An antibody described herein may have a low propensity for non-specific protein-protein interactions and good solubility.

An anti-IL17BR antibody molecule described herein may have a low propensity for aggregation when concentrated. A formulation described herein may comprise an antibody concentrated to 50-200 mg/ml, for example 75-150 mg/ml, preferably 80-120 mg/ml and more preferably 90-110 mg/ml, with a preferred concentration of about 100 mg/ml, without forming soluble aggregates in an aqueous solution maintained at physiological pH, for example by Dulbecco's PBS.

An anti-IL17BR antibody molecule described herein may have a low propensity for aggregation when subjected to repeated freezing and thawing, or prolonged temperatures above normal body temperature. For example, a prolonged temperature is 50° C. for 30 days in Dulbecco's PBS.

An anti-IL17BR antibody molecule described herein may have an isoelectric point (pI) between pH 7 and pH 9, preferably pH 7.4 to pH 8.2

An anti-IL17BR antibody molecule described herein may retain binding capability to IL17BR after incubation at 37° C. in serum from a mouse, human and/or cynomolgus primate. For example, an antibody described herein may retain binding capability to IL17BR after incubation in mouse, human and/or cynomolgus monkey serum for 10 to 50 days, preferably 20-40 days, more preferably 30 days. An antibody that retains binding capability may display the same or substantially the same binding capability at 37° C. as that observed in an antibody which was not incubated in serum, or which was incubated in a control solution.

An anti-IL17BR antibody molecule disclosed herein may be aglycosylated. The Fc regions of IgG antibodies bear a highly-conserved N-glycosylation site and glycosylation of the Fc fragment is essential for Fc receptor-mediated activity. The N-gly carbohydrate moieties attached to this site are predominantly core-fucosylated diantennary structures of the complex type. In addition, small amounts of these N-glycans also bear bisecting GlcNAc and α-2, 6 linked sialic acid residues. An aglycosylated antibody may lack one or more carbohydrate moieties by virtue of, for example, a chemical or enzymatic process, the absence or mutation of one or more glycosylation sites or expression in bacteria. An aglycosylated antibody described herein may be a deglycosylated antibody for which the Fc carbohydrate has been removed, for example, chemically or enzymatically. Alternatively, the aglycosylated antibody described herein may be a nonglycosylated or unglycosylated antibody that was expressed without Fc carbohydrate moieties, for example by mutation of one or more residues that encode the glycosylation pattern or by expression in an organism that does not attach carbohydrates to proteins, for example bacteria.

An anti-IL17BR antibody molecule as described herein may be afucosylated, i.e. engineered so that the carbohydrate moieties in the Fc region of the antibody do not have any fucose sugar units. Alternatively, an anti-Aβ antibody disclosed herein may be may have a reduced number of fucose sugar units. Afucosylated antibodies are more effective in antibody-dependent cell-mediated cytotoxicity (see below). Afucosylated antibodies described herein may be produced in cell lines engineered to produce afucosylated proteins, such as the Potelligent® CHOK1SV cell line (BioWa/Lonza), GlymaxX®-engineered cells (ProBioGen) or the duck embryonic stem cell line EB66 (Valneva).

An anti-IL17BR antibody molecule as described herein may be modified to enhance its antibody-dependent cell-mediated cytotoxicity (ADCC). ADCC is a cell-mediated reaction in which non-specific cytotoxic cells (e.g., Natural Killer (NK) cells, neutrophils, and macrophages) recognize bound antibody on a target cell and subsequently cause lysis of the target cell. Such a cell may be a human cell. ADCC activity of antibodies is generally thought to require the binding of the Fc region of an antibody to an antibody receptor existing on the surface of an effector cell, such as, for example, a killer cell, a natural killer cell and an activated macrophage. By altering fucosylation (e.g., reducing or eliminating) of the carbohydrate structure of a humanized antibody (i.e., in the Fc region), the ADCC activity of the antibody may be enhanced in vitro by, for example, 10-fold, or 20-fold, or 30-fold, or 40-fold, or 50-fold, or 100-fold, or 500-fold, or 600-fold, or 700 fold, or 1000-fold, relative to an unmodified humanized antibody. Because of increased ADCC activity, such modified antibodies may be used at lower dosages than their unmodified counterparts and generally have fewer or reduced side effects in patients.

An anti-IL17BR antibody as described herein may be used in complement-dependent cytotoxicity (CDC). CDC involves the central innate complement system which acts as the effector of adaptive immunity. The classical CDC pathway is triggered by antibody molecules binding to an antigen on a target cell and is initiated by binding of a C1q protein to the Fc domain of the bound antibody. The resulting complement cascade activates a membrane attack pathway, leading to the formation of a membrane attack complex which induces lysis of the target cell. An antibody as described herein may be modified to enhance its capability to trigger CDC by any method known in the art, such as but not limited to, engineering the protein backbone to contain amino acid residue substitutions in the constant domains of the antibody heavy chain. For an example of a combination of IgG1 amino acid substitutions used to enhance CDC activity, see Moore et al., *mAbs,* 2(2), 181-189 (2010). The CDC activity of a modified antibody as described herein may be enhanced by, for example, 10-fold, or 20-fold, or 30-fold, or 40-fold, or 50-fold, or 100-fold, or 500-fold, or 600-fold, or 700 fold, or 1000-fold, relative to an unmodified humanized antibody.

Anti-IL17BR antibody molecules may be further modified by chemical modification, for example by PEGylation, or by incorporation in a liposome, to improve their pharmaceutical properties, for example by increasing in vivo half-life.

An anti-IL17BR antibody molecule described herein may be formulated and/or administered as a pharmaceutical composition comprising the active therapeutic antibody agent and a variety of other pharmaceutically acceptable components, see Remington: The Science and Practice of Pharmacy (22nd ed., Pharmaceutical Press, London, Pa. (2013)). The preferred form depends on the intended mode of administration and therapeutic application. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers and the like.

Pharmaceutical compositions containing an anti-IL17BR antibody molecule described herein may also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers may function as immunostimulating agents (i.e., adjuvants).

For parenteral administration, an antibody or composition described herein may be administered as injectable dosages of a solution or suspension of the substance in a physiologically acceptable diluent with a pharmaceutical carrier that may be a sterile liquid such as water oils, saline, glycerol, or ethanol. Additionally, auxiliary substances, such as wetting or emulsifying agents, surfactants, pH buffering substances and the like may be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies may be administered in the form of a depot injection or implant preparation, which may be formulated in such a manner as to permit a sustained release of the active ingredient.

The term "parenteral" as used herein includes subcutaneous, intravenous, intradermal, intramuscular, intraperitoneal, and intrathecal administration of an antibody or composition described herein. An anti-ILI 7BR antibody or composition described herein may also be administered by nasal or gastric methods. Typically, compositions are prepared as injectables, either as liquid solutions or suspensions; solid forms suitable for solution in, or suspension in, liquid vehicles prior to injection may also be prepared. The preparation also may be emulsified or encapsulated in liposomes or micro particles such as polylactide, polyglycolide, or copolymer for enhanced adjuvant effect, as discussed above (see Langer, Science 249: 1527 (1990) and Hanes, Advanced Drug Delivery Reviews 28:97 (1997)). The antibody molecules of this invention may be administered in the form of a depot injection or implant preparation, which may be formulated in such a manner as to permit a sustained or pulsatile release of the active ingredient.

Additional formulations suitable for other modes of administration include oral, intranasal, and pulmonary formulations, suppositories, and transdermal applications. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Therapeutic formulations of the anti-IL17BR antibody molecule may be prepared for storage by mixing the antibody molecule having the desired degree of purity with optional physiologically acceptable carriers, excipients, or stabilizers (see e.g. "Remington: The Science and Practice of Pharmacy", 20th Edition, 2000, pub. Lippincott, Williams & Wilkins.), in the form of lyophilized powder or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

For the anti-IL17BR antibody molecule to be used for in vivo administration it must be sterile. This is readily accomplished by filtration through sterile filtration membranes, prior to or following lyophilization and reconstitution. The antibody molecule ordinarily will be stored in lyophilized form or in solution.

Preferably, an anti-IL17BR antibody molecule described herein or a composition comprising an anti-IL17BR antibody described herein may be administered intravenously (IV), intramuscularly (IM) or topically, for example via aerosol, lotion, ointment or topical solution, such as drops.

Topical application may result in transdermal or intradermal delivery. Topical administration may be facilitated by co-administration of the agent with cholera toxin or detoxified derivatives or subunits thereof or other similar bacterial toxins (See Glenn et al., Nature 391, 851 (1998)). Co-administration may be achieved by using the components as a mixture or as linked molecules obtained by chemical crosslinking or expression as a fusion protein. Alternatively, transdermal delivery may be achieved using a skin patch or using transferosomes (Paul et al., Eur. J. Immunol. 25:3521 (1995); Cevc et al., Biochem. Biophys. Acta 1368:201-15 (1998)).

Compositions may comprise an anti-IL17BR antibody molecule described herein, pharmaceutically acceptable carriers as described herein, and other therapeutic agents, in particular prophylactic or therapeutic agents useful for the prevention, management or treatment of allergic or inflammatory conditions. Such therapeutic agents may comprise analgesic drugs, anti-inflammatory drugs, anti-viral drugs, drugs which ameliorate fever or elevated body temperature, and/or therapeutic compounds designed to numb pain, e.g., mouthwashes or sprays which may numb mouth pain. A composition described herein may additionally comprise compositions for rehydrating a subject, for example by intravenous therapy.

Compositions described herein may comprise nucleic acids, i.e., DNA or RNA, encoding an anti-IL17BR antibody molecule described herein, and any method of delivery of such nucleic acids, with or without any of the other composition compounds discussed above. Compositions may also comprise vectors, for example but not limited to, the expression vectors described herein, themselves comprising the nucleic acids described herein.

Compositions described herein may comprise viral vectors, for use as nucleic acid delivery systems into cells. Suitable viral vector nucleic acid delivery systems include retroviral systems, adenoviral vectors, viral vectors from the pox family including vaccinia virus and the avian pox viruses, and viral vectors from the alpha virus genus. A nucleic acid encoding an antibody described herein, or a vector containing the same, may be packaged into liposomes for delivery to an individual or cell, which may be incorporated into compositions as described. Vectors and nucleic acids encoding an antibody may also be adsorbed to or associated with particulate carriers.

Compositions described herein may comprise gene therapy vectors which contain nucleotide sequences encoding for the antibodies described herein, or naked antibody polypeptide chains according to the invention. Compositions may comprise such vectors or polypeptides in combination with the antibodies described herein, and any other composition components described above.

An anti-IL17BR antibody molecule described herein may be used in a kit. The term "kit" is used in reference to a combination of reagents and other materials which facilitate sample analysis. In some embodiments, an immunoassay kit described herein includes a suitable antigen, binding agent comprising a detectable moiety, and detection reagents. A system for amplifying the signal produced by detectable moieties may or may not also be included in the kit. Furthermore, in other embodiments, the kit includes, but is not limited to, components such as apparatus for sample collection, sample tubes, holders, trays, racks, dishes, plates, instructions to the kit user, solutions or other chemical reagents, and samples to be used for standardization, normalization, and/or control samples.

Kits may contain at least one antibody described herein. A kit may comprise a composition described herein, in one or more containers, optionally with one or more other prophylactic or therapeutic agents useful for the diagnosis, prevention, management or treatment of an allergic or inflammatory condition or a cancer condition. A device capable of delivering the kit components through the route of administration may be included, e.g., a syringe. The kit may further include instructions for preventing, treating, managing or ameliorating allergic or inflammatory condition, as well as side effects and dosage information for method of administration.

The present invention also provides diagnostic kits. Antibodies described herein may be useful for monitoring, diagnosing, or providing a prognosis for the development or progression of an allergic or inflammatory condition or a cancer condition, and may be used in a kit suitable for such purposes. An antibody described herein may be used in a diagnostic kit to detect the presence of IL17BR, in a sample of body fluid taken from an individual, where the individual may be a human, or a mammal, such as a non-human primate or a laboratory animal, including mice, rats and rabbits. A sample of body fluid, such as but not limited to blood or serum is taken from an individual and tested for the presence of IL17BR using the antibodies described herein. Measuring IL17BR levels in the blood of an individual using an antibody described herein may provide information about the susceptibility, risk of onset, diagnosis or prognosis of allergic or inflammatory condition or a cancer condition in the individual, or suitable administration schedules or doses of an antibody or composition described herein for treating the individual. Diagnostic methods are generally performed in vitro. A method of detecting the presence of IL17BR in a sample from an individual may comprise contacting the sample with an anti-IL17BR antibody described herein and determining the binding of the antibody to IL17BR in the sample.

A kit which is useful for the diagnosis described above may comprise antibodies described herein which are coupled to a detectable substance including, but not limited to: various enzymes for use in assays including EIA and ELISA, such as, but not limited to, horseradish peroxidase, alkaline phosphatase, beta-galactosidase, or acetylcholinesterase; prosthetic groups, such as, but not limited to, streptavidin/biotin and avidin/biotin; particles, such as latex beads or bacteria, for use in agglutination tests; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as, but not limited to, luciferase, luciferin, and aequorin; radioactive materials, such as, but not limited to, iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; positron-emitting metals using various positron-emission tomographies, non-radioactive paramagnetic metal ions, and molecules that are radiolabelled or conjugated to specific radioisotopes. Any detectable label that may be readily measured may be conjugated to an antibody described herein and used in diagnosing a disease as described herein. The detectable substance may be coupled or conjugated either directly to an antibody or indirectly, through an intermediate (such as, for example, a linker known in the art) using techniques known in the art. Metal ions which may be conjugated to antibodies for use as a diagnostics are known in the art (see, e.g., US474900).

Detection of the antigen by using any of the methods or detectable substances described above may give a positive result for the presence of IL17BR using the antibodies described herein in a kit as described herein and may diagnose an individual as having allergic or inflammatory condition or a cancer condition or provide prognostic information about an individual with allergic or inflammatory condition or a cancer condition or at risk of allergic or inflammatory condition or a cancer condition. Such an individual may subsequently require and/or undergo treatment for the allergic or inflammatory condition, or the cancer condition, as described herein.

Aspects of the invention are also directed to a method of treatment, including prophylaxis, of an allergic or inflammatory condition or a cancer condition, by administering to an individual in need of treatment an effective amount of an antibody or composition described herein. An antibody or composition, preferably a pharmaceutical composition (e.g., a composition comprising an antibody described herein, a pharmaceutically acceptable excipient and optionally an additional therapeutic agent) described herein may be for use as a medicament for example in a method of treatment of the human or animal body. An antibody or composition, preferably a pharmaceutical composition, described herein may be for use in a method of treatment of the human or animal body, wherein the treatment is therapeutic or prophylactic treatment of an allergic or inflammatory condition or a cancer condition in an individual.

Allergic or inflammatory conditions may include IL25 mediated diseases, such as allergy; inflammatory bowel disease (IBD); inflammation of the colon; asthma, including allergic asthma and rhinovirus exacerbated asthma; airway hyperresponsiveness (AHR); fibrosis, including idiopathic pulmonary fibrosis; colitis, including chronic colitis, ulcerative colitis and Crohn's disease; and inflammatory ocular conditions, such as keratoconjunctivitis sicca (dry eye syndrome).

Cancer conditions may include pancreatic cancer, breast cancer, liver cancer and thyroid cancer.

An anti-IL17BR antibody molecule may for example be useful in preventing or reducing AHR in a subject. A method of preventing or reducing AHR in a subject (e.g. a human) in need thereof may comprise administering to the subject an anti-IL17BR antibody molecule described herein.

An anti-IL17BR antibody molecule may for example be useful in preventing or reducing inflammation of the colon. A method of preventing or reducing inflammation of the colon in a subject (e.g. a human) in need thereof, may comprise administering to the subject an antibody molecule that binds IL17BR as described above. For example, an anti-IL17BR antibody molecule may for example be useful in preventing, reducing or treating IBD. A method of preventing, reducing or treating IBD, which comprises administering to the subject an antibody molecule that binds IL17BR as described above.

The treatment methods mentioned above may comprise administration of the antibody or composition (e.g., a composition comprising an antibody described herein, a pharmaceutically acceptable excipient and optionally an additional therapeutic agent) described herein to an individual under conditions that generate a beneficial therapeutic response in the individual e.g., for the prevention or treatment of an allergic or inflammatory condition.

An individual suitable for treatment as described herein may be suffering from an allergic or inflammatory condition or a cancer condition. The methods of treatment described herein may be used on both asymptomatic patients, and those currently showing symptoms of an allergic or inflammatory condition or a cancer condition. An antibody described herein may be administered prophylactically to an individual who does not have an allergic or inflammatory condition or a cancer condition. An antibody described herein may be administered to an individual who does not have, or does not exhibit the symptoms of an allergic or inflammatory condition or a cancer condition. An antibody described herein may be administered to an individual who does have, or appears to have, an allergic or inflammatory condition or a cancer condition. Individuals amenable to treatment include individuals at risk of or susceptible to an allergic or inflammatory condition but not showing symptoms and individuals suspected of having allergic or inflammatory condition or a cancer condition, as well as individuals presently showing symptoms. Antibodies described herein may be administered prophylactically to the general population without the need for any assessment of the risk of the subject individual.

In some embodiments, an individual suitable for treatment as described herein may display increased levels of biomarkers associated with Th2 responses relative to control individuals, for example healthy members of the population, or relative to levels determined previously in the individual. Biomarkers associated with Th2 responses may include exhaled nitric oxide, blood eosinophils, or serum biomarkers, such as IgE, IL-13, or chemokines such as eotaxin-3, and thymus and activation-regulated chemokine (TARC/CCL17). A method may comprise obtaining a sample from the individual, determining the levels of one or more biomarkers in the sample and administering an antibody as described herein if the level of one or more biomarkers associated with Th2 responses is increased.

The terms "treat", "treating" or "treatment" (or grammatically equivalent terms) mean that the severity of the individual's condition is reduced or at least partially improved or ameliorated and/or that some alleviation, mitigation or decrease in at least one clinical symptom is achieved and/or there is an inhibition or delay in the progression of the condition and/or prevention or delay at the onset of a disease or illness.

An anti-IL17BR antibody molecule described herein which may be used in a method of treatment for allergic or inflammatory condition or cancer condition may be an antibody of any sequence and format described above. The antibody molecule used for methods of treatment as described herein may be fragments of anti-IL17BR antibodies described herein, for example antigen binding fragments.

An anti-IL17BR antibody molecule described herein may be administered to an individual in need of treatment with a pharmaceutical carrier or pharmaceutical composition, or in any composition described herein. Alternatively, the anti-IL17BR antibody molecule may be administered to an individual by administering a polynucleotide encoding at least one antibody chain. The polynucleotide is expressed to produce the antibody chain in the patient. Optionally, the polynucleotide encodes heavy and light chains of the anti-IL17BR antibody molecule. The polynucleotide is expressed to produce the heavy and light chains in the individual.

The terms "patient", "individual" or "subject" include human and other mammalian subjects that receive either prophylactic or therapeutic treatment with one or more agents (e.g. immunotherapeutic agents or antibodies) described herein. Mammalian subjects include primates, e.g., non-human primates. Mammalian subjects also include laboratory animals commonly used in research, such as but not limited to, rabbits and rodents such as rats and mice.

An anti-IL17BR antibody molecule described herein may be used in a method of preventing or treating an allergic or inflammatory condition or a cancer condition that involves administering to the patient an effective dosage of the antibody as described herein. As used herein, an "effective amount" or an "effective dosage" or a "sufficient amount" (or grammatically equivalent terms) of a therapeutic antibody described herein refers to an amount of antibody or composition described herein that is effective to produce a desired effect, which is optionally a therapeutic or prophylactic effect (i.e., by administration of a therapeutically effective amount). For example, an "effective amount" or an "effective dosage" or a "sufficient amount" may be an amount so that the severity of the individual's condition, e.g., allergic or inflammatory condition or a cancer condition, is reduced or at least partially improved or ameliorated and/or that some alleviation, mitigation or decrease in at least one clinical symptom is achieved and/or there is an inhibition or delay in the progression of an allergic or inflammatory condition or a cancer condition and/or prevention or delay at the onset of an allergic or inflammatory condition or a cancer condition.

Effective doses of the compositions described herein, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals, e.g., non-human primates, rabbits, rats and mice, including transgenic mammals, may also be treated. Treatment dosages need to be titrated to optimize safety and efficacy.

For passive immunization with an antibody described herein, the dosage ranges from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages may be 1 mg/kg body weight or 10 mg/kg body weight or within the range of 1-10 mg/kg, preferably at least 1 mg/kg. In another example, dosages may be 0.5 mg/kg body weight or 15 mg/kg body weight or within the range of 0.5-15 mg/kg, preferably at least 1 mg/kg. In another example, dosages may be 0.5 mg/kg body weight or 20 mg/kg body weight or within the range of 0.5-20 mg/kg, preferably at least 1 mg/kg. In another example, dosages may be 0.5 mg/kg body weight or 30 mg/kg body weight or within the range of 0.5-30 mg/kg, preferably at least 1 mg/kg. In a preferred example, dosages may be about 30 kg/mg.

The methods described herein may comprise the administration of an antibody to a subject as a single dose, in two doses, or in multiple doses. The dose of the antibody may be from about 100 μg/kg to 100 mg/kg body weight of the patient, from about 300 μg/kg to 30 mg/kg body weight of the patient, or from about 1 mg/kg to 10 mg/kg body weight of the patient. Subjects may be administered such doses daily, on alternative days, weekly or according to any other schedule determined by empirical analysis. A treatment may involve administration in multiple dosages over a prolonged period, for example, of at least six months. Additional treatment regimens may involve administration once per every two weeks or once a month or once every 3 to 6 months. Exemplary dosage schedules include 1-20 mg/kg or 15 mg/kg on consecutive days, 30 mg/kg on alternate days or 60 mg/kg weekly.

In both prophylactic and therapeutic treatment regimes, reagents may be administered in several dosages until a sufficient immune response has been achieved. The term "immune response" or "immunological response" includes the development of a humoral (antibody mediated) and/or a cellular (mediated by antigen-specific T cells or their secretion products) response directed against an antigen in a recipient subject. Typically, the immune response is monitored and repeated dosages are given if the immune response starts to wane. For example, an antibody described herein may be administered on multiple occasions. Intervals between single dosages may be weekly, monthly or yearly. Intervals may also be irregular as indicated by measuring blood levels of the anti-IL17BR antibody in the patient. In some methods, dosage is adjusted to achieve a plasma antibody concentration of 1-1000 μg/ml and in some methods 25-300 μg/ml. Alternatively, an antibody described herein may be administered as a sustained release formulation, in which case less frequent administration is required. Dosage and frequency vary depending on the half-life of the antibody in the patient. In general, humanized antibodies show a longer half-life than chimeric and nonhuman antibodies.

The dosage and frequency of administration may vary depending on whether the treatment is prophylactic or therapeutic. In prophylactic applications, compositions containing the antibodies described herein or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time.

Doses for nucleic acids encoding antibodies described herein range from about 10 ng to 1 g, 100 ng to 100 mg, 1 μg to 10 mg, or 30-300 μg DNA per patient. Doses for infectious viral vectors vary from 10-100, or more, virions per dose.

Antibodies and compositions described herein may be administered for therapeutic and/or prophylactic treatment by parenteral, topical, intravenous, oral, gastric, subcutaneous, intra-arterial, intracranial, intraperitoneal, intranasal or intramuscular methods, as described herein. Intramuscular injection or intravenous infusion are preferred for administration of antibodies.

Other aspects and embodiments described herein provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope described herein.

All documents and sequence database entries mentioned in this specification are incorporated herein by reference in their entirety for all purposes.

Antibody residues positions described herein are numbered according to the scheme set out in Kabat, E. A., Wu, T. T., Perry, H. M., Gottesmann, K. S & Foeller, C. (1991). Sequences of Proteins of Immunological Interest, 5th edit., NIH Publication no. 91-3242. U.S. Department of Health and Human Services. Where appropriate, the position of a substitution may be described relative to a Kabat numbered residue which is invariant in immunoglobulin sequences. An alternative antibody numbering schemes are described in Honegger, A and Plückthun A. (2001). *J. Mol. Biol* 309, 657-67.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

EXPERIMENTS

Methods

Biacore Kinetics Against Human IL-17BR-His

A Human Antibody Capture kit was used to coat an anti-human IgG (Fc) antibody (in 10 mM sodium acetate, pH 5.0 immobilisation buffer) onto flow paths 2-4 a CM5 chip. Flow-path 1 was blocked and used as a blank control. This anti-human IgG coated chip was then used to immobilize the humanized antibody variants. A concentration series from 20-1.25 nM of Human IL17BR-His using a 2-fold dilution series was made using HBS-EP+ buffer. Purified antibody samples were diluted to 1 µg/ml in HBS-EP+ buffer and each injected onto one coated flow-path on the chip at a flow-rate of 10 µl/min for 2 mins in a Biacore T200 (GE Healthcare). Association time was set to 8 mins and Dissociation to 90 mins at a flow-rate of 30 µl/min Kinetics of binding/dissociation were analysed using a 1:1 model in the BIAevaluation software IL-17BR Biacore Competition Assay Firstly, a Protein A biacore chip was produced by capturing 10 ug/ml biotinylated protein A (Sigma) onto to a SA sensor chip. This chip was inserted into a Biacore 2000 instrument. The anti-IL-17BR antibody was injected at a flow rate of 20 ul/min at 10 ug/ml. This was followed by a 10 ul injection of IL-17B/IL-25 to check for non-specific binding of the antibodies to the ligands. The IL-17 receptor was then injected onto the chip at 10 ug/ml followed by a second injection of IL-17B/IL-25 at the same concentration. Regeneration was performed using 10 ul 10 mM Glycine-HCl, pH 2.2.

Thermal Stability Comparison

Fully humanized antibodies and the chimeric control were diluted to 1 µg/mL in PBS/0.2% Tween and aliquoted at the appropriate volume for the EC80 concentration into PCR tubes. The volume was made up to 100 µl with the same buffer. Each tube was heated separately for 10 min at temperatures between 30° C. and 85° C. with a 5° C. interval and cooled to 4° C. Binding assay was performed against the Human IL-17BR-His extracellular domain using 100 µl of each antibody per well (assay each temperature in duplicate) in a 96-well plate.

Thermal Shift Comparison

Samples were prepared directly into 96 well white PCR plate in a final volume of 25 µL (purified antibody final concentration of 1 and 2 µM). Stock Sypro Orange was diluted 1:100 in PBS buffer, then added 1:10 to final samples (e.g. 2.5 µL in 25 µL). The samples were loaded onto a qPCR machine and amplified using the MxPro software, SYBR Green method, (filter=FRROX, no reference dye), with a thermal profile setup of 71 cycles of 1° increase. Results were plotted and Tm determined.

SEC-MALS (Freeze-Thaw and Heat Induced Stress Tests)

Size exclusion chromatography-multi angle light scattering (SEC-MALS) analysis was carried out on 'non-stressed' and 'stressed samples' to detect for the presence and/or induction of aggregates, which could potentially give rise to downstream manufacturing issues. 10 µl of each sample (1 mg/mL) was injected onto a SEC column (Acquity UPLC BEH200 SEC, 4.6×150 mm, 1.7 µm) and subsequently detected by three in-series detectors: UV (Agilent 1260 Infinity HPLC system with thermostatted column compartment); Light-scattering (Wyatt Technology DAWN HELEOS) and Differential Refractometer (Wyatt Technology Optilab TRex). A constant flow-rate of 0.4 mL/min was applied using a mobile phase of Dulbecco's PBS (Sigma D8537 containing 0.01% sodium azide). All experiments were carried out at 25° C. The data was analyzed with Wyatt Technology ASTRA software (version 6.1.2.83) and with the refractive index increment (dn/dc) set to 0.185 (i.e. for protein analysis). All samples were stored at 4° C., prior to analysis by SEC-MALS.

Cross-Interaction Chromatography (CIC)

Cross-interaction chromatography (CIC) analysis was carried out to assess proneness to non-specific protein-protein interactions and provide an indication of any solubility issues, which can give rise to downstream manufacturing problems. Samples were analyzed by two separate 20 µl injections (0.5 mg/mL); firstly onto a 1 mL NHS activated resin (GE Healthcare) coupled with 30 mg human polyclonal IgG (Sigma 14506) and secondly onto a 1 mL NHS activated resin blank coupled, as control column. The mobile phase consisted of Dulbecco's PBS (Sigma D8537) containing 0.01% sodium azide (0.1 mL/min) and all experiments were performed at 25° C. Eluted samples were detected by UV absorbance (Agilent 1260 Infinity HPLC system with thermostatted column compartment) and data was analyzed using Wyatt Technology ASTRA software (version 6.1.2.83) to determine sample peak retention times. These were then used to calculate a retention factor k':

$$k' = \frac{(Tr - Tm)}{Tm}$$

where $T_r$ is the retention time of the sample on the poly-IgG column and $T_m$ is the retention time on the mock (control) column.

Solubility Assessment by Solvent Absorption

A Vivapore™ solvent absorption concentrator was loaded with 3.5-5.0 ml antibody at 1 mg/ml in PBS at time 0. Antibody concentration was monitored every 10 min by sampling a small amount for measuring on the Nanodrop 2000 (E=1.4) and continuing until the concentrated volume reaches the dead volume of ~30-50 µl. The concentration values (mg/ml) were plotted against the corresponding time points to generate the concentration profiles.

Dynamic light scattering (DLS)

Dynamic light scattering was used as a complementary technique (i.e. to static-light scattering such as SEC-MALS) for the detection of soluble aggregates. Where performed, 30 μl samples (Dulbecco's PBS; Sigma D8537) were loaded into a 348-well polypropylene plate (Greiner bio-one) and data recorded on a Zetasizer APS (Malvern). All values were recorded in triplicate and processed using the associated Zetasizer software (version 7.10). A cumulants analysis was performed to obtain mean particle size (z-average) and the polydispersity index (PDI).

ELISA (Enzyme-Linked Immunosorbent Assay)

ELISA plates were coated overnight at 4° C. with 2 μg/ml human IL17RA-Fc fusion protein(Sino Biological, 10895-H03H), human IL17BR-his tag protein (Sino Biological, 13091-H08H), human IL17RC-histag protein (11747-H08B), human IL17RD-his tag (10507-H08H). The next day, plates were blocked with 1% BSA in PBS, followed by the addition of hD9042. The binding specificity of hD9042 was measured as the absorbance at 450 nm using anti-human IgG F(ab')2 peroxidase antibody (Jackson ImmunoResearch Inc).

In Vitro Human IL-5 and IL-13 Cytokine Production Assay on Human Peripheral Blood Mononuclear Cells (PBMC)

Fresh human PBMCs were resuspended in RPMI1640 with 10% heat inactivated human AB serum (Sigma Aldrich) and then seeded into 96 deep well plate (Nunc) at a density of $7.5 \times 10^4$ cells/well in a total of 200 μL culture medium as indicated above. For the induction of IL-5 and IL-13 expression, 10 U/mL human IL-2 (Peprotech, 200-02) combined with 2 ng/ml or 10 ng/ml human IL-25 (R&D systems, 1258-IL/CF) were added to each well. For the inhibition studies, PBMC were treated with 2 μg/mL hD9042 or Isotype control (ChromPure Human IgG, whole molecule, Jackson ImmunoResearch Inc) for 1 hour prior to the addition of IL-2 and IL-25. Supernatant were harvested on day 7 post cytokine and antibody treatment, and analyzed by IL-5 and IL-13 ELISA kit (SAB biotech).

In Vitro Human IL-8 Cytokine Production Assay on Human Renal Cell Carcinoma Cell Line TK-10

TK-10 cells were maintained in RPMI1640 medium with 10% Fetal Bovine Serum at 37° c., 5% CO2 in humidified atmosphere. For IL-8 stimulation, TK-10 cells were seeded at a density of $2.5 \times 10^4$ cells/well in a total 100 μL volume OptiMEM reduced serum medium(Thermofisher Scientific), followed by the treatment of 10 ng/ml human TNFα (Peprotech, 300-01A) and 100 ng/ml human IL-25 (R&D systems, 1258-IL/CF) for 24 hours. For inhibition studies, TK-10 cells were treated with 100 ng/mL hD9042, hD9043 or Isotype control (ChromPure Human IgG, whole molecule, Jackson Immuno Research Inc) for 1 hour prior to the addition of TNFα and IL-25. The supernatant harvested after the treatment of cytokines and antibody treatment were analyzed by human IL-8 ELISA Kit (R&D systems, D8000C).

Results

Sequence Determination of the D9.2 Antibody

The cloning and sequencing of murine D9.2 was performed as described in patent number U.S. Pat. No. 8,852, 589.

Generation of a Chimeric Version of the D9.2 Antibody

1. Construction of the Chimeric D9.2 Expression Vectors

Construction of chimeric expression vectors entails appending suitable leader sequence DNA to VH and VK genes, preceded by a HindIII restriction site. The leader sequences are selected as the most similar sequence in the Kabat database. Furthermore, the construction of the chimeric heavy chain expression vector entails introducing a 5'-fragment of the human IgG1 heavy chain constant region genes, up to a natural ApaI restriction site, contiguous with the 3' end of the J region of VH gene. For the construction of the chimeric kappa light chain expression vector, a 3'-splice donor site and a 5' BamHI restriction site was added to the VK gene. The splice donor sequence is important for the correct in-frame attachment of the variable region gene to its appropriate constant region genes, thus splicing out the V:C intron. The appropriate constant region genes are encoded downstream of the inserted variable region sequence. The 400 bp (approx.) PCR product of the Advantage HF2 (Clontech) reaction of cD9.2 VK was cloned into the pCR2.1vector using the TOPO-TA Cloning kit and the manufacturers protocol. DNA plasmid minipreps of selected clones for the correct fragment size were cut with HindIII and BamHI and ligated into the vector pKN100. Clones were isolated, after transformation of chemically-competent DH5α bacteria by the ligation product. Overnight cultures (5 ml) of four clones were processed using the QIAprep Spin Miniprep Kit, in accordance with the manufacturer's protocols, to produce DNA plasmid minipreps, sequenced by GATC-Biotech, using primer Hu-K3 and named D9.2 cVK.pKN100. The 450 bp (approx.) PCR product of the Advantage HF2 (Clontech) reaction of cD9.2 VH was treated with DpnI, cut with Hind III and ApaI and directly ligated into the expression vector pG1D200. Clones were isolated after transformation of chemically-competent DH5α bacteria by the ligation product, and screened by PCR using primers HCMVi (F0951) and chD9.2VH REV. Overnight cultures (5 ml) of five clones generating the correctly-sized PCR product were processed using the QIAprep Spin Miniprep Kit, in accordance with the manufacturers protocols, to produce DNA plasmid minipreps, sequenced by GATC-Biotech, using primer HCMVi and named D9.2 cVH.pG1D200.

2. Generation of the Chimeric D9.2 Antibody

Plasmid preparations of D9.2 cVH.pG1D200 and D9.2 cVK.pKN100 were purified from overnight cultures of transformed DH5α bacteria using the Promega Maxiprep System and the manufacturer's protocol. These 2 plasmids were used to co-transfect 293T cells. The conditioned medium was harvested after 3-4 days. $IgG_1$-kappa antibody concentration in the conditioned medium from 293T transfections measured by quantitation ELISA was 1862.78 ng/ml and 3573.13 ng/ml in two sets of triplicate transfections for D9.2.

3. IL-17BR Binding Activity of Chimeric cD9001 Antibody

Antibody binding activity to the extracellular domains of recombinant Human IL-17BR-His (R&D Systems), Mouse IL-17BR-(Fc) (Sino Biological) and Cynomolgus monkey IL-17BR-monoFc was measured by binding ELISA. FIG. 1 shows that the chimeric antibody cD9001 binds to the Human, Mouse and Cynomolgus monkey IL-17BR proteins with similar $EC_{50}$ values.

Design of D9.2 Humanized Antibody Variants

1. Human VH and VK cDNA Databases

The protein sequences of human and mouse immunoglobulins from the International Immunogenetics Database 2009 (Lefranc, 2015) and the Kabat Database Release 5 of Sequences of Proteins of Immunological Interest (last update 17 Nov. 1999) (Kabat et al. 1991) were used to compile a database of human immunoglobulin sequences in Kabat alignment. Our database contains 10,406 VH and 2,894 VK sequences.

2. Molecular Model of D9.2

A homology model of mouse D9.2 antibody variable regions has been calculated using the Discovery Studio 3.5 program run in automatic mode. The atomic coordinates of 3rkd_C.pdb and 1mj8_H.pdb were the highest scoring sequence templates for the VL and VH respectively as determined by Blast analysis of the Accelrys antibody pdb structures database, and the atomic coordinates of 4aeh_LH.pdb was the highest scoring overall (interface) sequence template. These templates were used to generate 30 initial models; the top scoring model was refined by modelling each CDR loop with its 5 best loop templates. The 20 final models were used to determine a consensus of residues which were within 4 Å of the CDR loops.

3. Human Framework Selection

Humanization requires the identification of suitable human V regions. Human VH and VK databases were interrogated with D9.2 VH and VK protein sequences using various selection criteria. FW residues within 4 Å of the CDR residues (Kabat definition) in the structures of mouse D9.2 antibody were identified, and designated as the "4 Å Proximity Residues". Humanized sequences and incomplete sequences were removed from the analysis. The sequence EF178110 was chosen as the human heavy chain donor candidate. This sequence scores fairly high in sequence identity and similarity, and has six 4 Å Proximity Residue changes, but this was the minimal number of changes obtainable (Table 1).

Likewise, the sequence Y14869 was chosen as the human kappa light chain donor candidate. This sequence scores very high in sequence identity and similarity to D9.2 VK and has no somatic mutations from the IGKV1-NL1*01 germline. It has two potential 4 Å Proximity Residue changes (Table 2).

4. Design of D9 HA and HB

As a suitable human framework has been identified, the synthetic protein and DNA sequence can be designed. The initial design of the humanized version of D9.2 is the grafting of CDR 1, 2 and 3 from D9.2 VH into the acceptor FW of EF178110, therefore creating variant D9 HA (SEQ ID NO: 7). The six 4 Å Proximity Residues, at positions 52, 74-76, 79 and 105 are then back mutated to the mouse equivalent residue, in the humanized version D9 HB, and mutated one at a time in the following variants: sequences were assembled in silico and designated D9 HC to D9 HH. Table 1 compares the murine and the humanized versions of D9 VH protein sequences.

5. Design of D9 KA and D9 KB

The framework from Y14869 was used to design the DNA and protein for the humanized constructs. CDR 1, 2 and 3 from D9 VK are shown grafted into the acceptor FW of Y14869 to generate the initial version of humanized D9 (KA SEQ ID NO: 12). The two unmatched 4 Å Proximity residues, 54 and 76, were back mutated to the mouse equivalent residue in the humanized version D9 KB, and mutated one at a time in the following variants: sequences were assembled in silico and designated D9 KC and KD (Table 2).

Generation and Properties of a Humanized Version of D9.2 Antibody

1. Generation of D9 Humanized Antibodies Construction of humanized expression vectors entails cloning the amplified variable regions into IgG/kappa vectors (pHuK and pHuG1), using ligase-independent cloning (LIC). The vectors (pCMV modified) are digested with BfuA1 (BspM1) and then compatible overhangs are generated with T4 DNA polymerase 3'-5' exonuclease activity (+dATP).

The genes for the variable regions of D9 HA, HB, KA and KB were synthesized by GenScript. The natural human framework sequences EF178110 and Y14869, heavy and light chains, respectively, and the natural mouse CDR sequences were assembled in silico and designated D9 HA to D9 HH and designated D9 KA to D9 KE. The sequences for HA/B and KA/B were optimized by silent mutagenesis to use codons preferentially utilized by human cells and synthesized. KA/B and HA/B constructs were PCR amplified with specific primers to the expression vector+insert. Firstly, the variable region was amplified by PCR with primers containing the 3' end of the leader sequence (most of the sequence is present in the vector)—forward primer— or the beginning of the constant region (IgG1 or kappa)— reverse primer—, followed by the beginning of the variable region (in each direction). The complementary overhangs were generated in the PCR products by T4 DNA polymerase+dTTP treatment. Vector and inserts were incubated at RT, transformed into chemically-competent TOP10 bacteria and plated on Kanamycin plates. Several clones were isolated and colonies screened by PCR using primers HCMVi and HuG1 LIC Rev for VH or HuK LIC Rev for VK. The clones generating the correct sized PCR products were selected, miniprepped using the QIAGEN kit and sequenced using the same primers. Version HA and KA were subsequently modified by PCR mutagenesis to obtain other humanized variants annotated in Tables 1 and 2 respectively. Clones were sequenced and plasmid DNA was prepared using the QIAGEN Plasmid Miniprep Kit or Promega Plasmid Maxiprep kit. Expression plasmid preparations encoding (humanized or chimeric) VH, HA, KA and VK were used to transfect Expi293 cells, cultured for 5-7 days in serum free media, whereupon the conditioned medium containing secreted antibody was harvested.

2. Antibody Expression

The concentrations of $IgG_1K$ antibodies in Expi293 cell conditioned media were measured by HTRF and are shown in Table 3. This is a competitive immunoassay based on HTRF technology (Homogeneous Time-Resolved Fluorescence) for the quantitative determination of human IgGs which can displace the binding between IgG labelled with XL665 and Mab anti-human $F_c$ labelled with cryptate. Specific signal (i.e. energy transfer) is inversely proportional to the concentration of human $F_c$ in the sample or standard. The chimeric antibody (cD9001) showed good expression as did the other antibodies expressed with the chimeric light chain (D9 HAcK and D9 HBcK). However, the antibodies containing the KA light chain (cHKA, D9 HAKA and D9 HBKA) all had very low levels of expression. Therefore a model light chain named KM shown in Table 2, was used to determine which heavy chain to use. Antibodies expressed with KM as the light chain mostly showed higher expression levels (hD9002, hD9006, hD9010, hD9014, hD9018, hD9022, hD9026 and hD9030).

3. Antigen Binding by Initial Versions of the Humanized D9 Antibodies

Off-rate ranking was performed using the Biacore on the heavy chain variants with KM to determine which heavy chain version had the slowest off-rate with Human IL-17BR. The data was fitted using the association and dissociation and the data was ranked using the $K_{off}$ values (Table 4). Version H for the heavy chain gave the slowest off-rate (hD9030) so was chosen as the lead heavy chain version at this stage.

4. Biacore Competition Assay with IL-17B or IL-25

Figure 2:
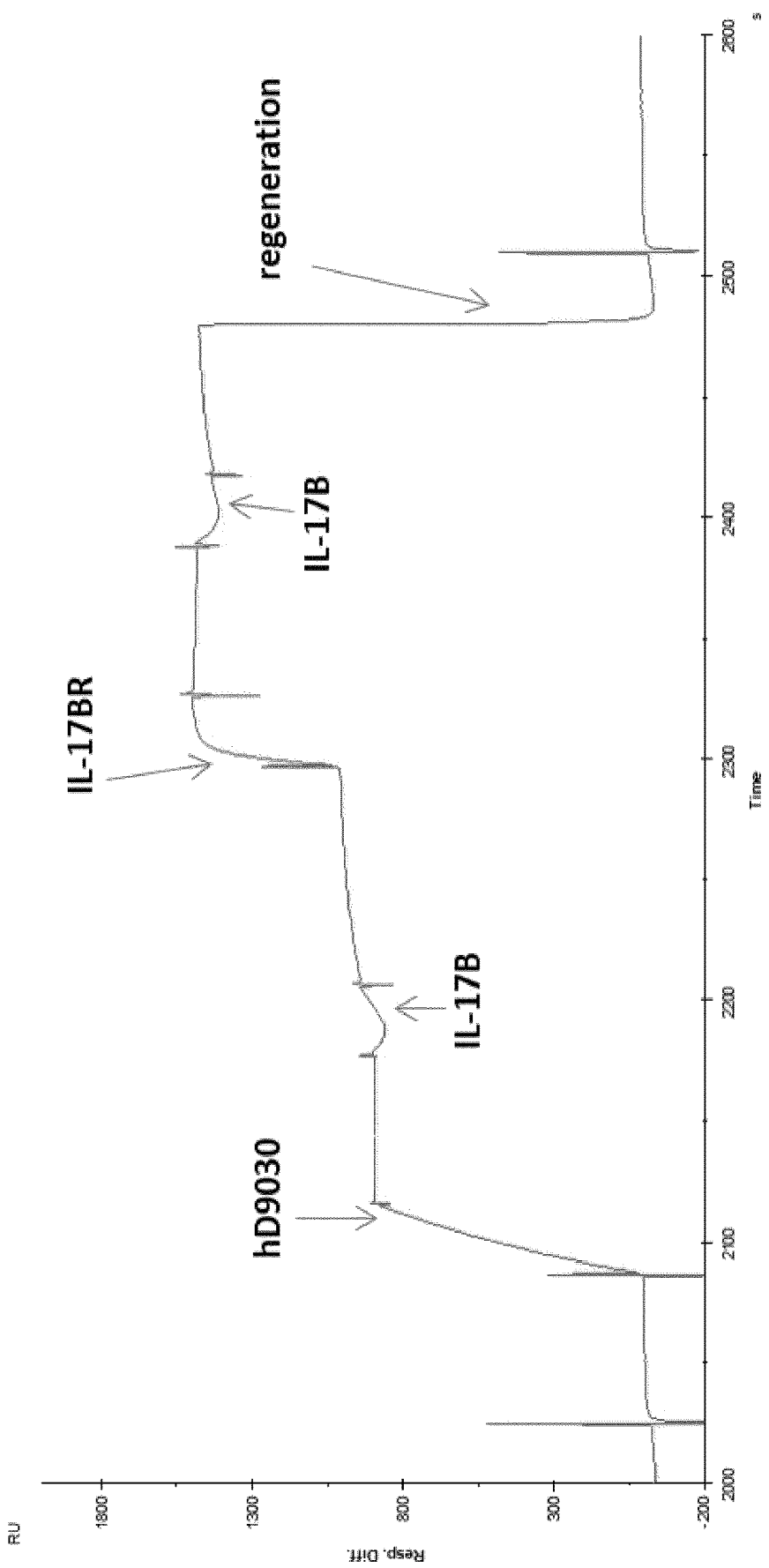
FIG. 2 shows the lack of binding of IL-17B to IL-17BR in the presence of one of the humanised antibodies hD9030.
Figure 3:
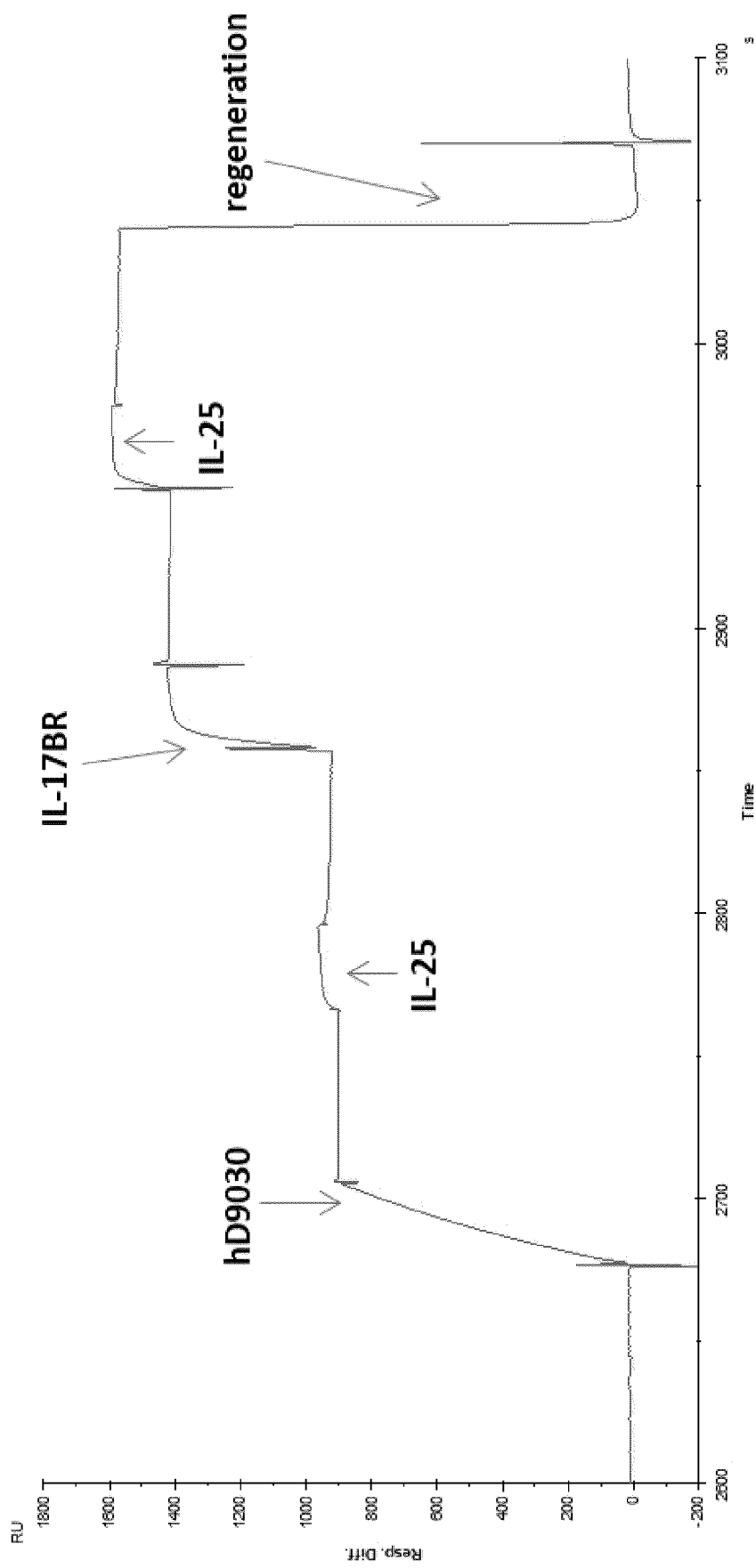
FIG. 3 shows the ability of IL-25 to bind to IL-17BR in the presence of one of the humanised antibodies hD9030.

To determine whether the humanised antibodies compete directly with IL-17B or IL-25 for binding to IL-17BR, a Biacore competition assay was performed. Firstly, the humanised antibody hD9030 was loaded onto a pre-coated Protein A chip. IL-17B or IL-25 was injected to check for binding to the antibody alone. Following this, IL-17BR was injected and the binding to the antibody could be observed as indicated in FIGS. 2 and 3. IL-17B/IL-25 was then injected again to see if the natural ligand could bind to the receptor in the presence of the humanised antibody. In the case of IL-17B, the latter was unable to bind to IL-17BR in the presence of the humanised antibody (FIG. 2), suggesting that their epitopes could overlap. However, for IL-25, binding to IL-17BR could be observed following binding of the humanised antibody to the receptor (FIG. 3), suggesting that they do not directly compete for the same site.

5. Re-Engineering of Heavy and Light Chain Sequences

In light of the data showing the KA light chain variant did not express well, the light chain sequence was analysed further. Version KE was generated with Arg99 in D9 KA mutated to Gly (Table 2) using site-directed mutagenesis.

It was also desired to engineer the heavy chain sequence to have a higher percentage identity to human germline (>85%). The KE light chain identity to human germline is 86% so no engineering was necessary with this construct. For the heavy chain, the identity to human germline of the current lead heavy chain H, was 80.4% so a number of mutations were required to reach >85%. The sequence was examined by molecular modelling and 2 potential versions were considered; mutating 3 residues in the framework regions or 3 residues in CDRH2 which did not seem essential for binding. Both of these heavy chain versions were produced using site-directed mutagenesis (Section 8.8) and were named D9 HI and D9 HJ as shown in Table 1.

6. Re-Engineered Antibodies; Expression and Purification

The expression levels (transfected using Expi293 cells) of antibodies containing D9 HH-HJ heavy chains with either the original KA or the modified KE light chain were quantified using the Octet quantitation assay. Again all of the antibodies containing D9 KA as the light chain (hD9035, hD9036 and hD9037) had low expression levels whereas the antibodies containing D9 KE as the light chain (hD9040, hD9041 and hD9042) showed reasonable expression levels as shown in Table 3. The antibodies hD9040, hD9041 and hD9042 were chosen as the 3 lead humanised antibody candidates to further characterize and were purified using affinity and size-exclusion chromatography.

7. Antigen Binding by the Humanized D9 Antibodies

Figure 4:
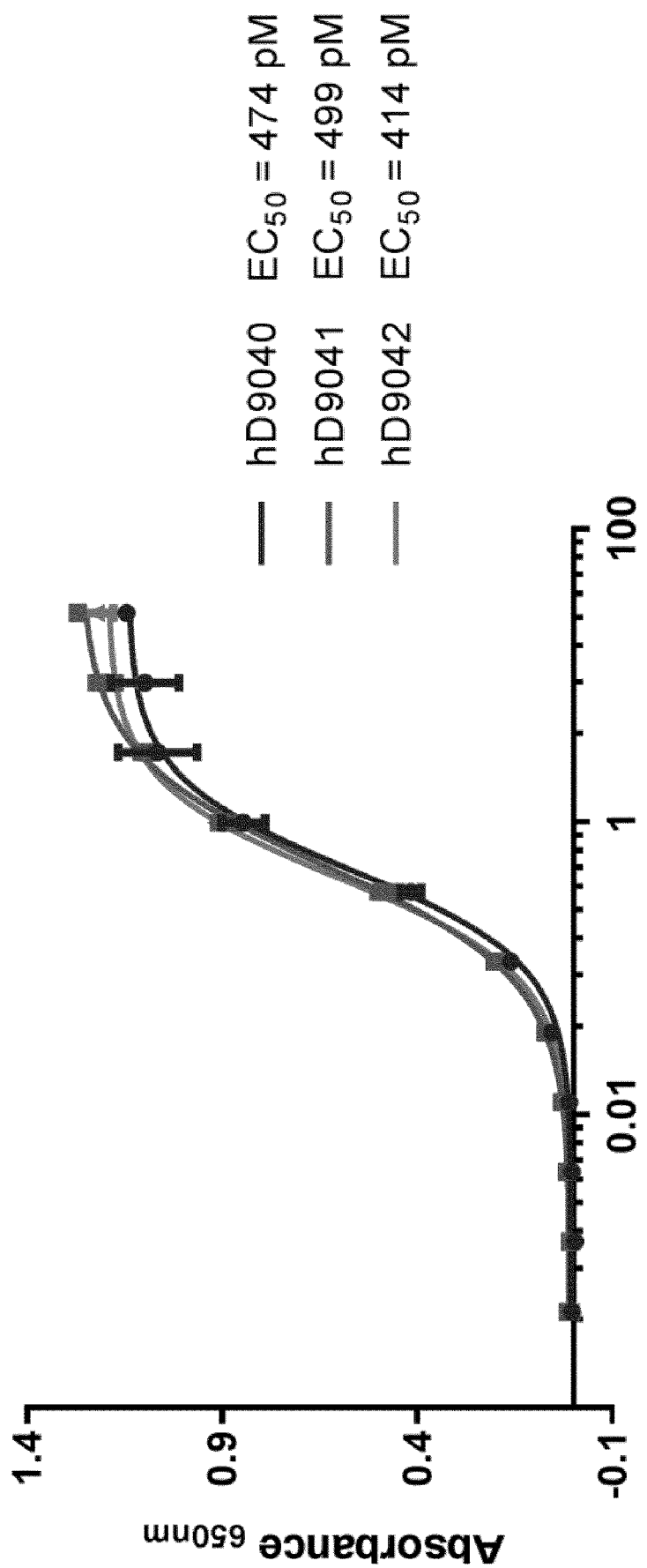
FIG. 4 shows the binding of the humanized antibodies hD9040-42 to Human IL-17BR

The binding of Human IL-17BR to antibody versions hD9040, hD9041 and hD9042 was tested by ELISA. All 3 humanised variants bound to Human IL-17BR-His with very similar $EC_{50}$ values (FIG. 4).

Figure 5:
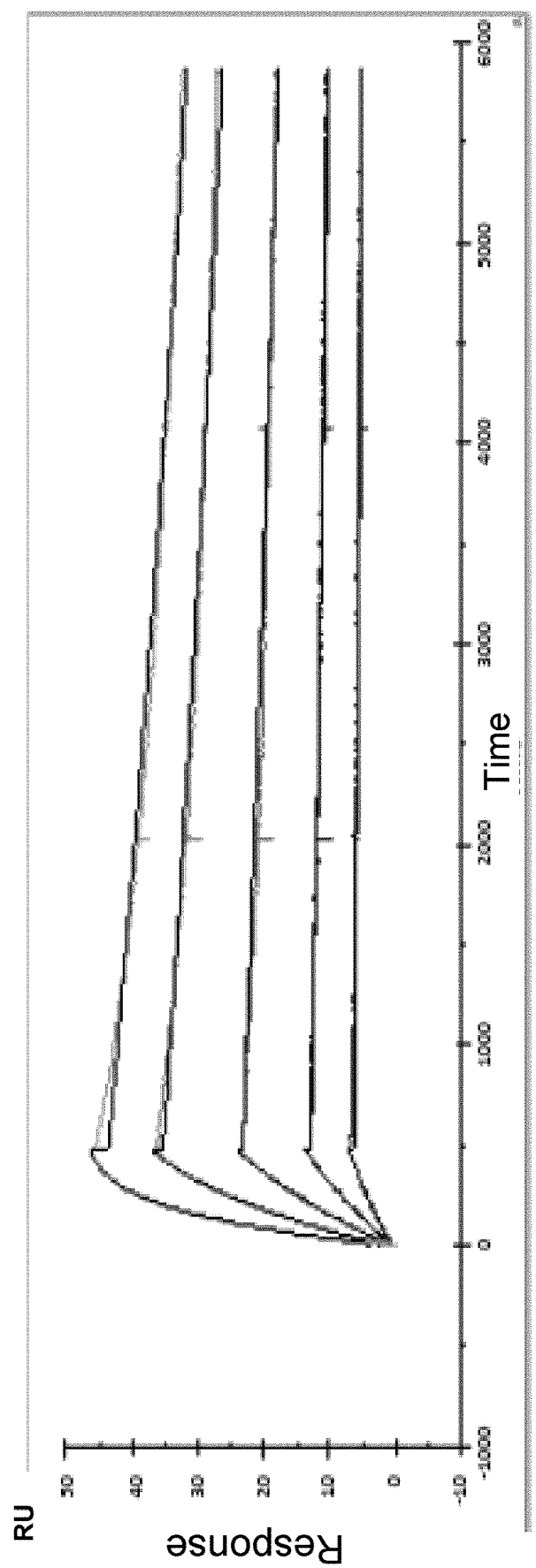
FIG. 5 shows the kinetics of the humanized antibodies hD9040-42 with Human IL-17BR
Figure 5:
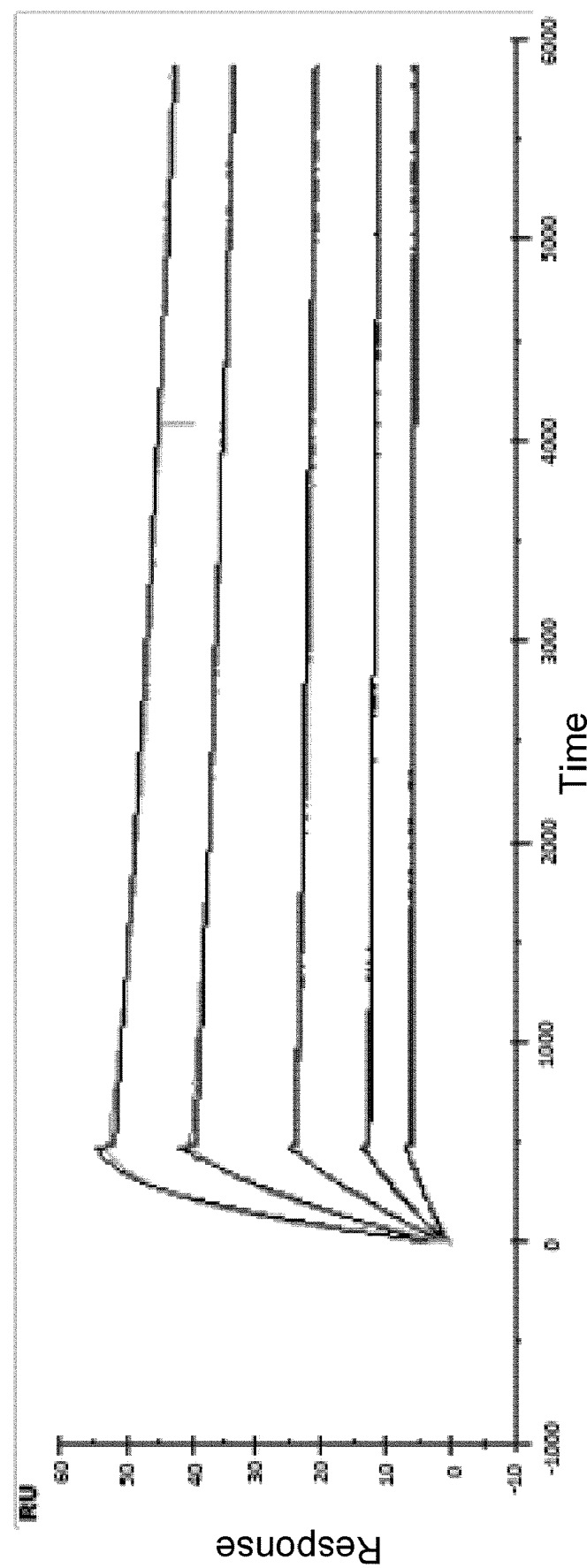
Figure 5:
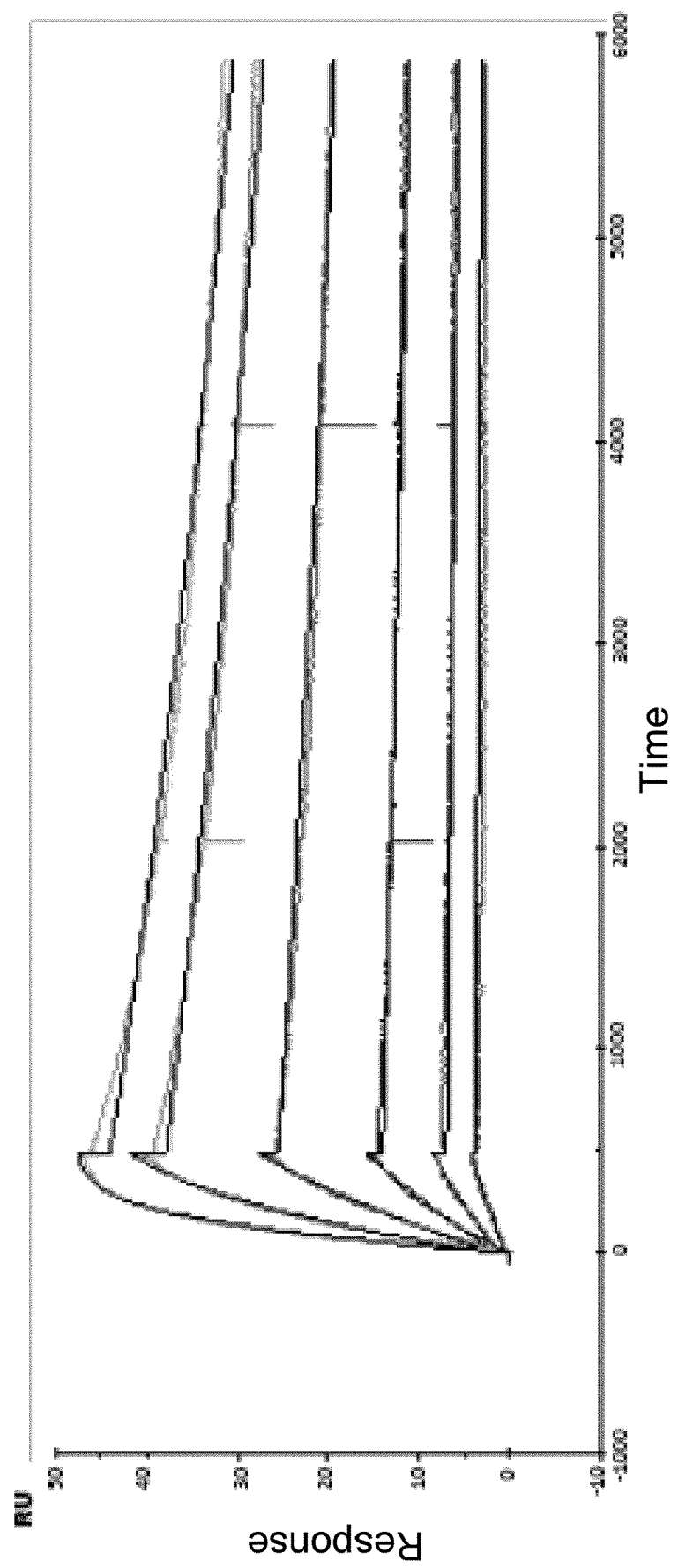

8. Kinetics of the Binding of Humanized hD9040, hD9041 and hD9042 Antibodies to IL-17BR To further characterize the binding of the lead humanized candidates hD9040, hD9041 and hD9042 antibodies to Human IL-17BR-His, kinetics experiments were performed using the Biacore T200 instrument. The three humanized antibodies demonstrate good kinetics with affinities in the low picomolar range (FIG. 5). Although these tight affinities are reaching the limits of the Biacore instrument, it is clear that all three antibodies have comparable affinities to the chimeric antibody.

Figure 6:
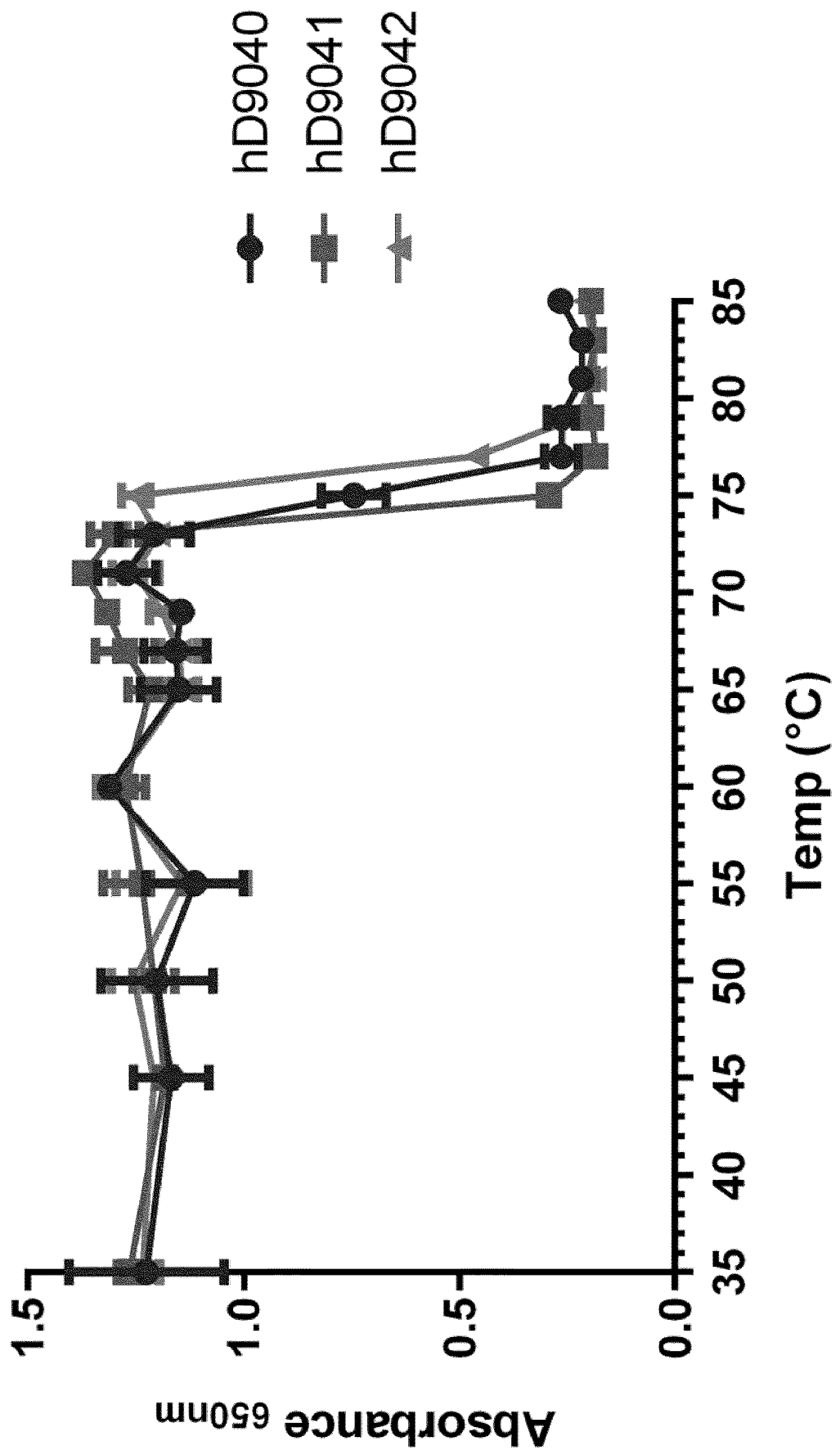
FIG. 6 shows the thermal stability of the humanized antibodies hD9040-42

9. Thermal Stability of Humanized hD9040, hD9041 and hD9042 Antibodies to High Temperatures The aim of this experiment is to test the thermal stability of the humanized antibodies when subjected to high temperatures, varying from 30° to 85° C. for 10 minutes, cooled to 4° C. and used in an ELISA assay at the $EC_{80}$ concentration of each candidate. The humanized candidates hD9040 and hD9041 retain their binding ability to Human IL-17BR-His until 73° C. and hD9042 retains binding up to 75° C. (FIG. 6).

Figure 7:
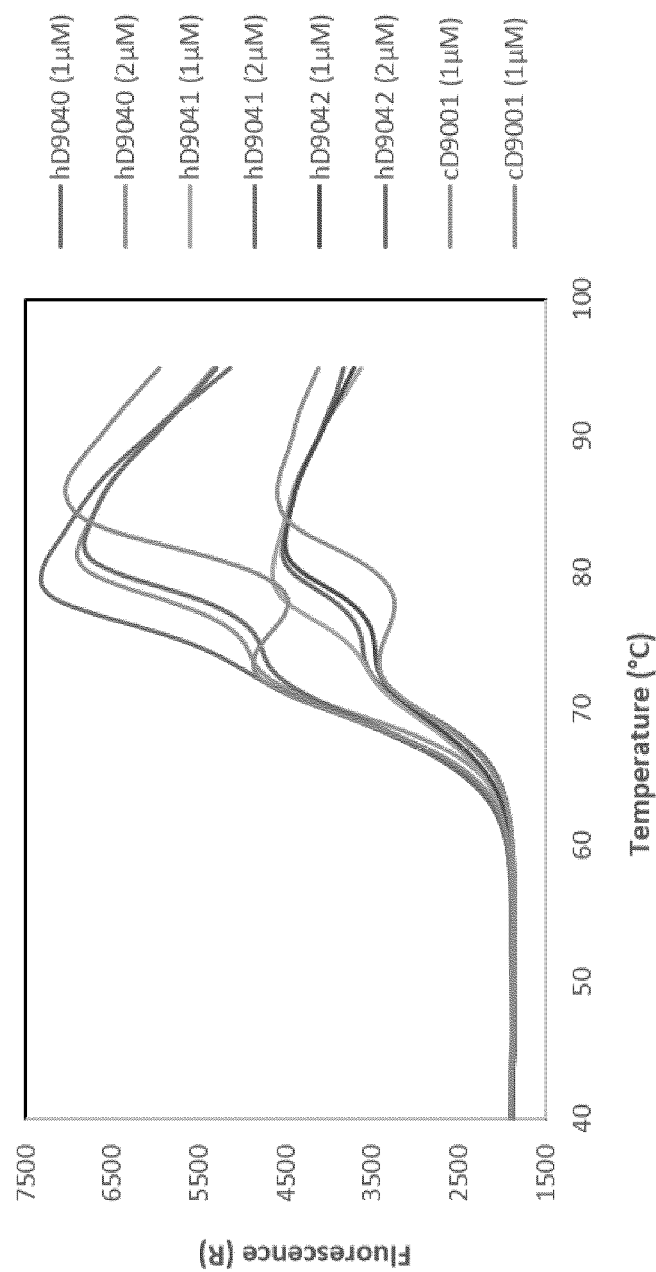
FIG. 7 shows thermal shift analysis of humanized antibodies hD9040-42.

10. Determination of the Tm (Melting Temperature) of Humanized hD9040, hD9041 and hD9042 Antibodies In order to determine the melting temperature of the lead humanized antibodies hD9040, hD9041 and hD9042, they were tested in a thermal shift assay. Samples were incubated with a fluorescent dye (Sypro Orange) for 71 cycles with 1° C. increase per cycle in a qPCR thermal cycler. Tm values for the humanized antibodies were calculated to be between 72-74° C. (FIG. 7, Table 5).

11. Aggregation of Humanized hD9040, hD9041 and hD9042 Antibodies

Figure 8:
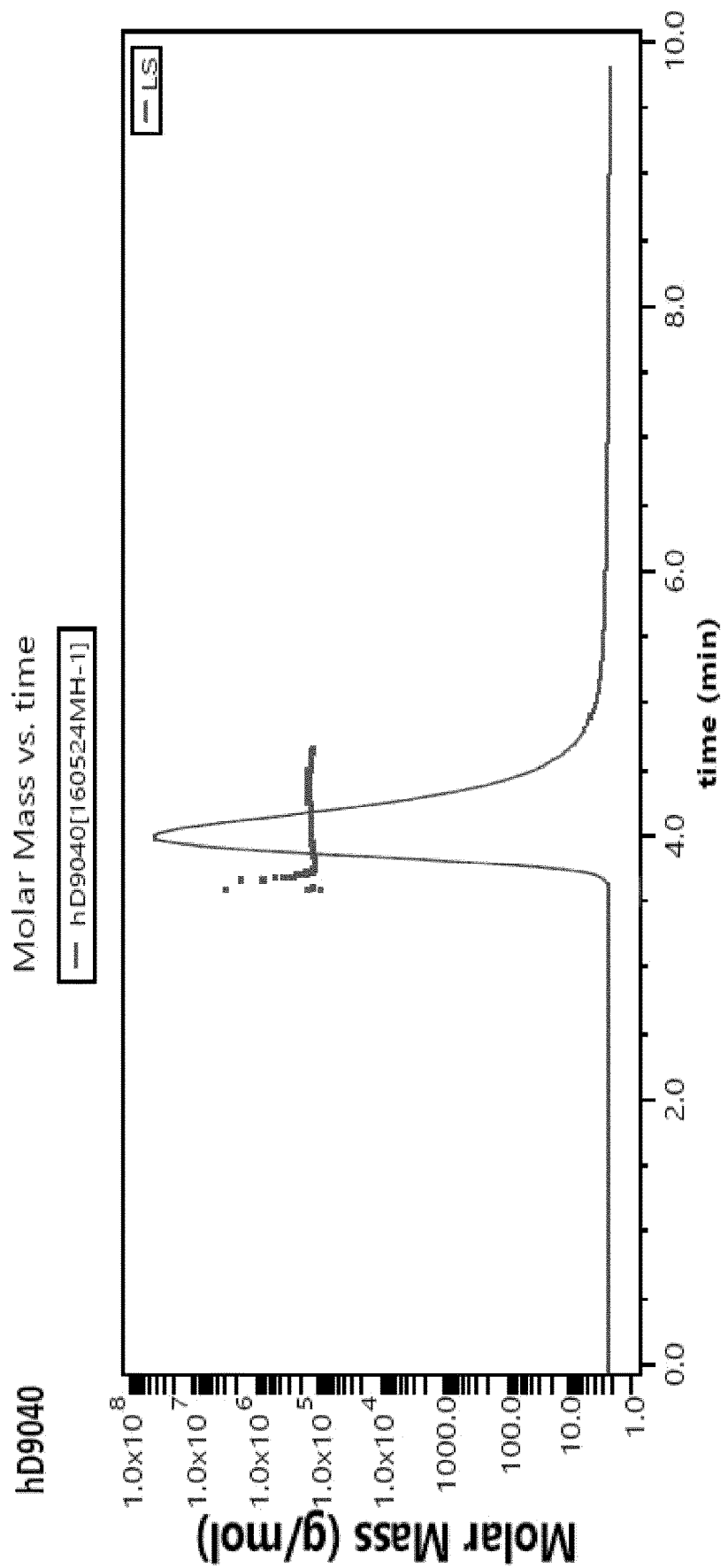
FIG. 8 shows aggregation analysis of humanized antibodies hD9040-42
Figure 8:
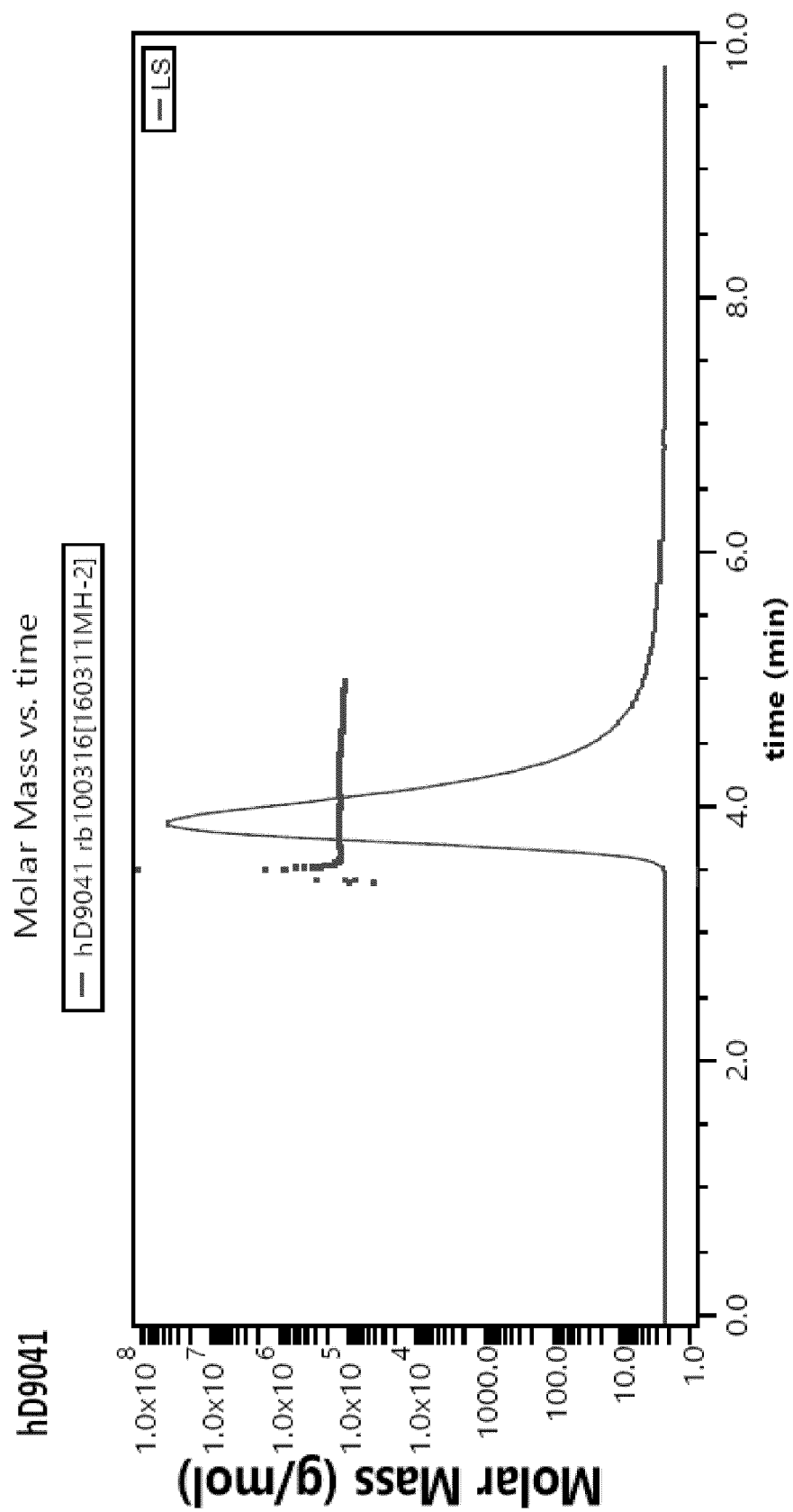
Figure 8:
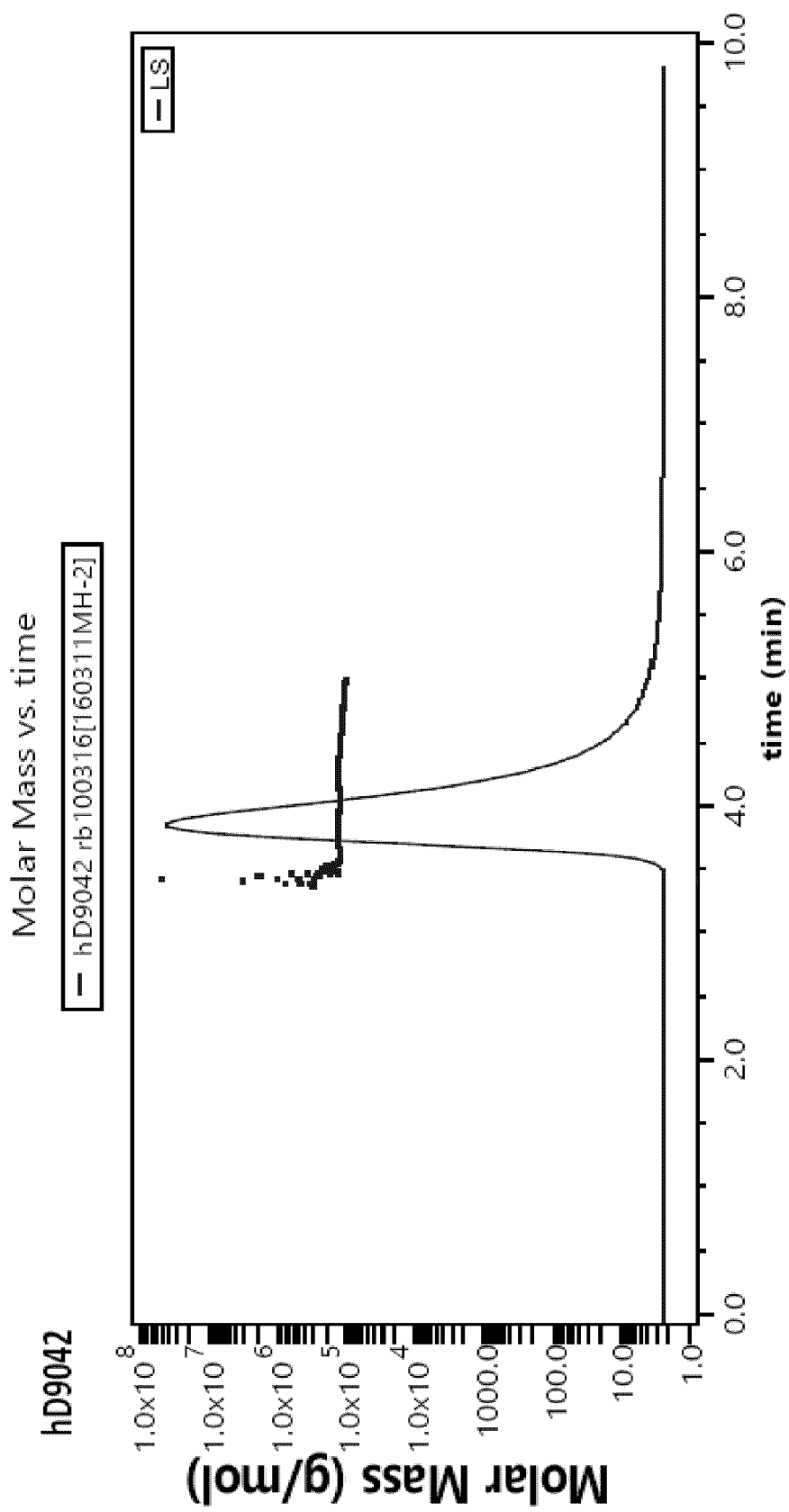

Samples were injected at 0.4 mL/min into a size exclusion column in an HPLC system and analyzed by multi-angle light scattering to determine the absolute molar masses and check for aggregation. The profile shows no signs of aggregation (FIG. 8; Table 6) with an average molecular weight of between 136-132 kDa (Table 6), for the humanized candidates hD9040, hD9041 and hD9042. This is the expected range for an IgG monomer in this analysis setup. The antibodies are monodispersed (Mw/Mn<1.05). The mass recovery is 100% (calculated mass over injected mass), which indicates good protein recovery and that the sample does not seem to stick to the column or contain insoluble aggregates, which would be retained by the guard column. Overall the data suggest there are no aggregation concerns for the humanized antibodies hD9040, hD9041 and hD9042.

Figure 9:
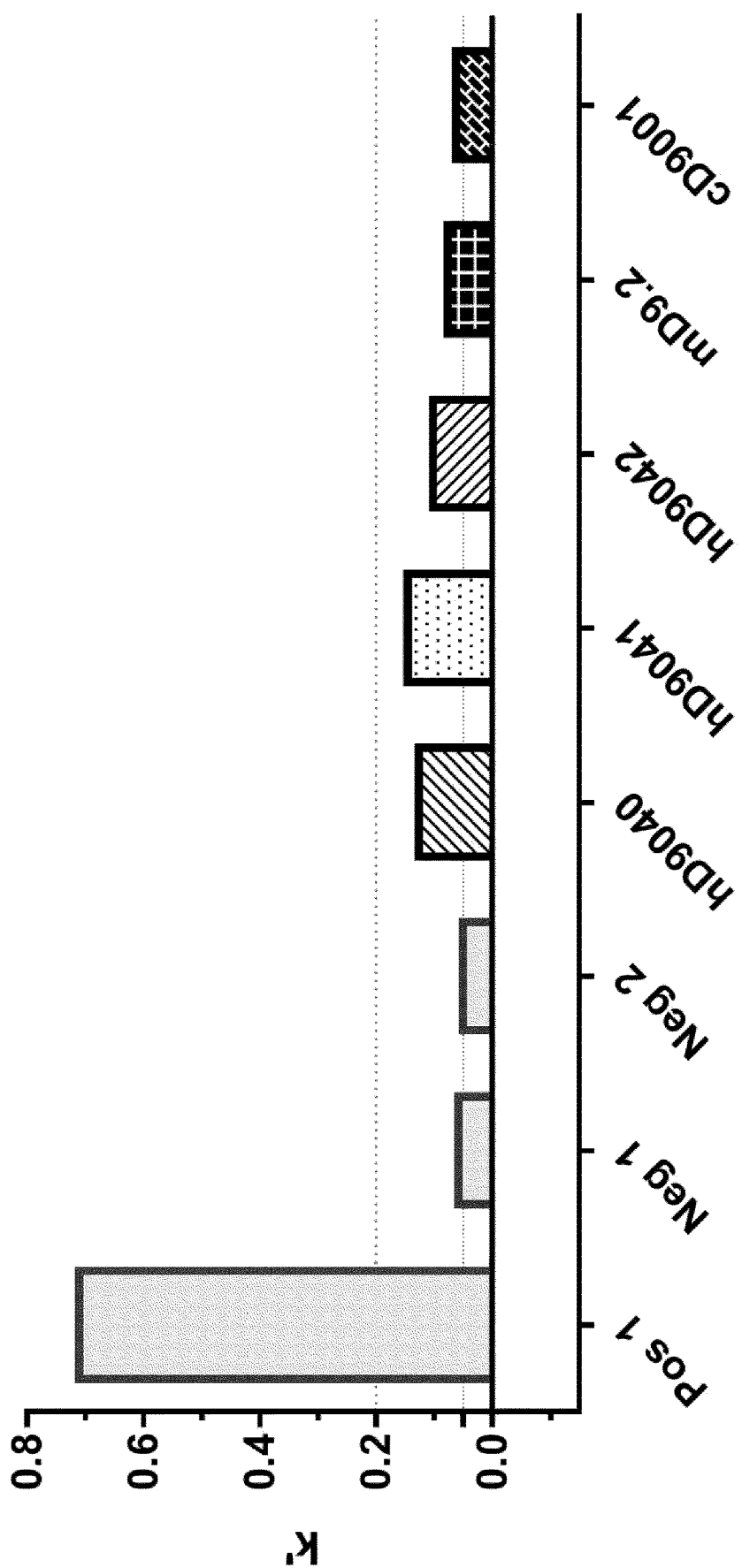
FIG. 9 shows non-specific protein-protein interactions (cross-interaction chromatography) of humanized antibodies hD9040-42.

12. Non-Specific Protein-Protein Interactions (CIC) of Humanized hD9040, hD9041 and hD9042 Antibodies Cross-Interaction Chromatography using bulk purified human polyclonal IgG is a technique for monitoring non-specific protein-protein interactions, and can be used to discriminate between soluble and insoluble antibodies. An elevated Retention Index (k) indicates a self-interaction propensity and a low solubility. Antibody hD9042 has the least propensity for non-specific interactions, followed by hD9040 then hD9041. All three humanized antibodies show Retention Indexes below 0.2, indicating they generally have a low propensity for non-specific interactions and good solubility (FIG. 9).

13. Solubility of Humanized hD9040, hD9041 and hD9042 Antibodies

Figure 10:
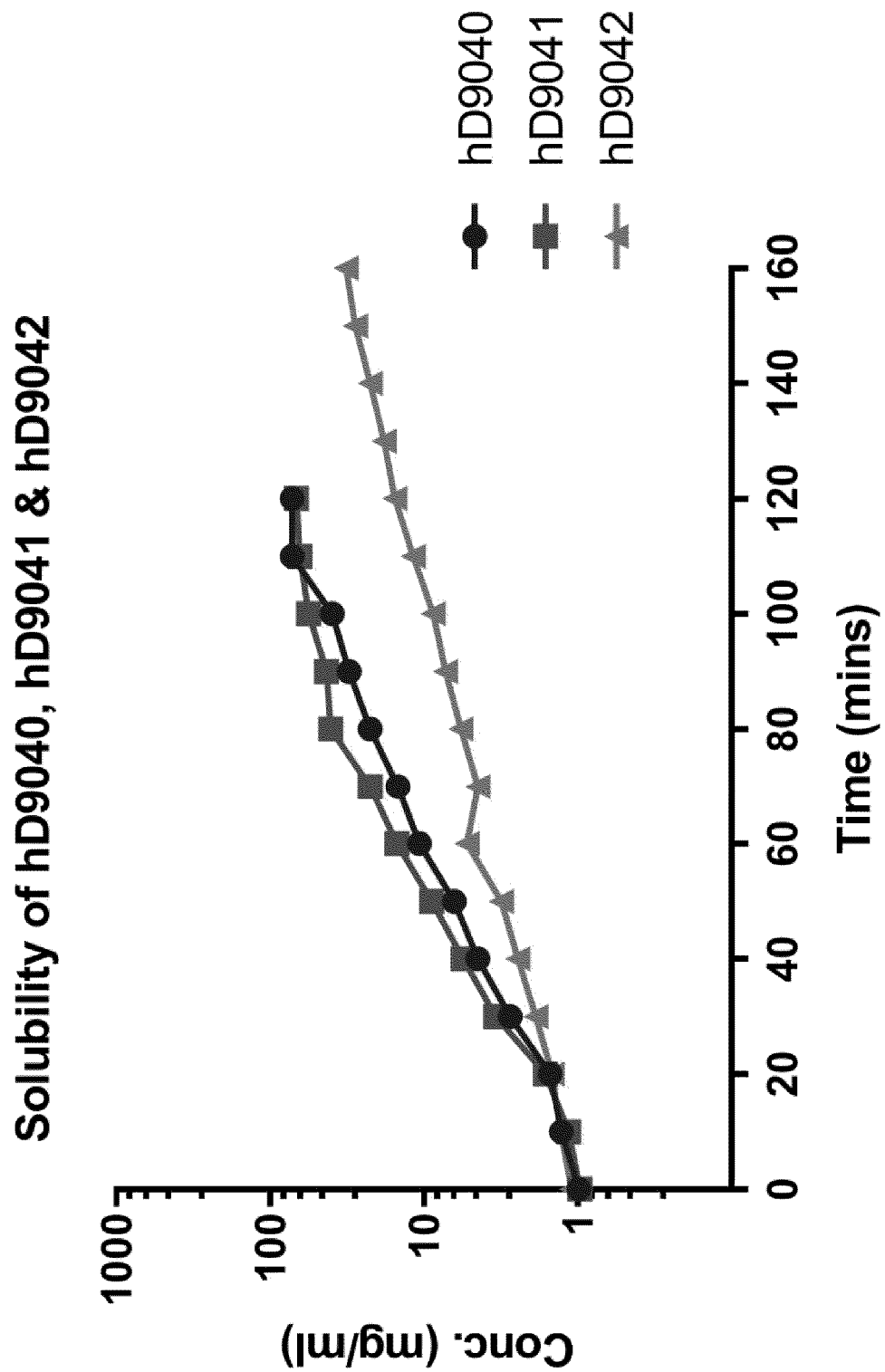
FIG. 10 shows purified humanized antibodies hD9040-42 assessed for solubility.

The humanized antibodies hD9040, hD9041 and hD9042 were concentrated using solvent absorption concentrators (MWCO 7500 kDa) and the concentration measured at timed intervals. The antibodies were concentrated to >65 mg/mL without apparent precipitation indicating they are soluble in PBS to high concentrations (FIG. 10).

Figure 11A:
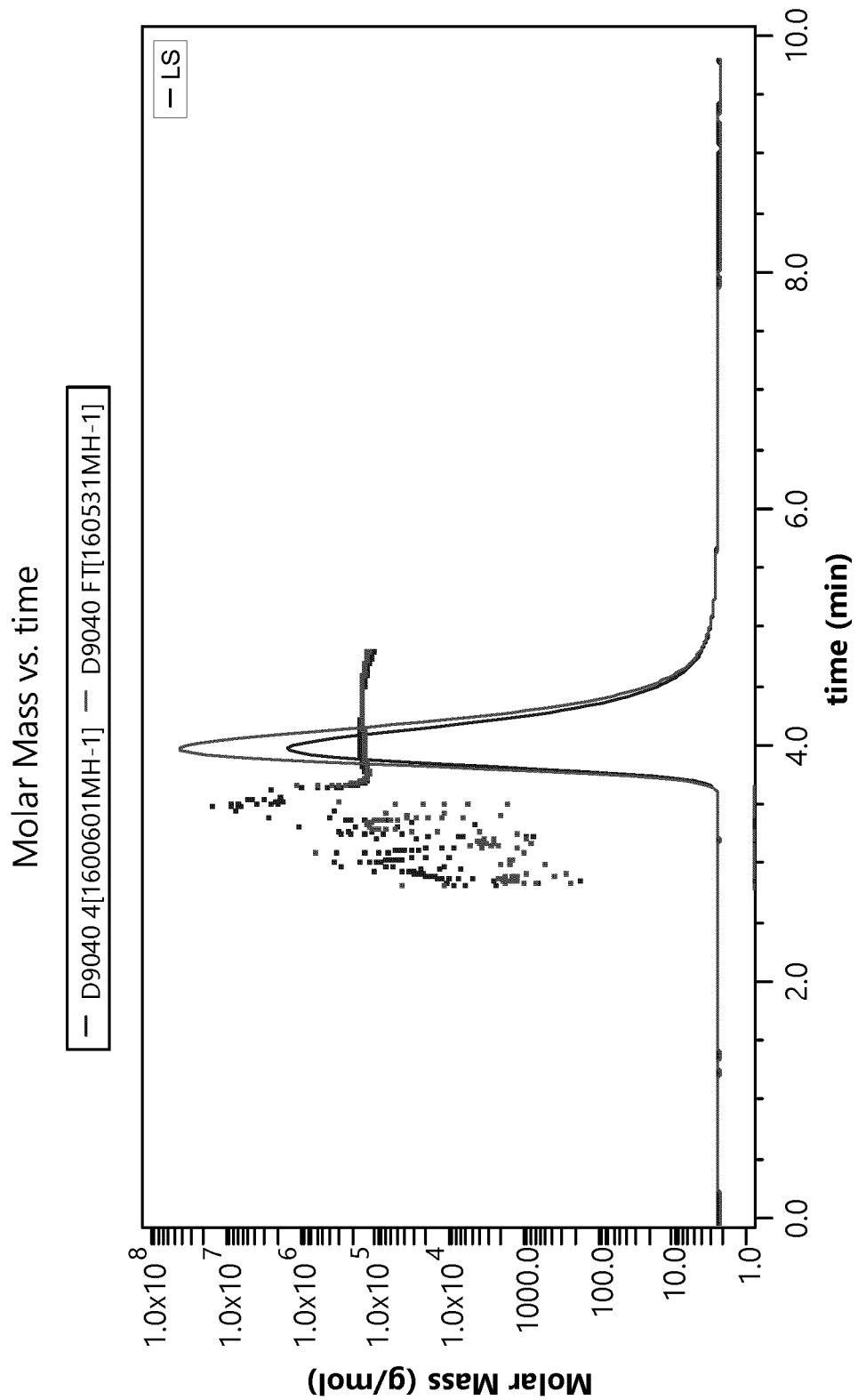
FIG. 11 shows Freeze/Thaw stress analysis of humanized antibodies hD9040 (11A), hD9041 (11B) and hD9042 (11C).
Figure 11B:
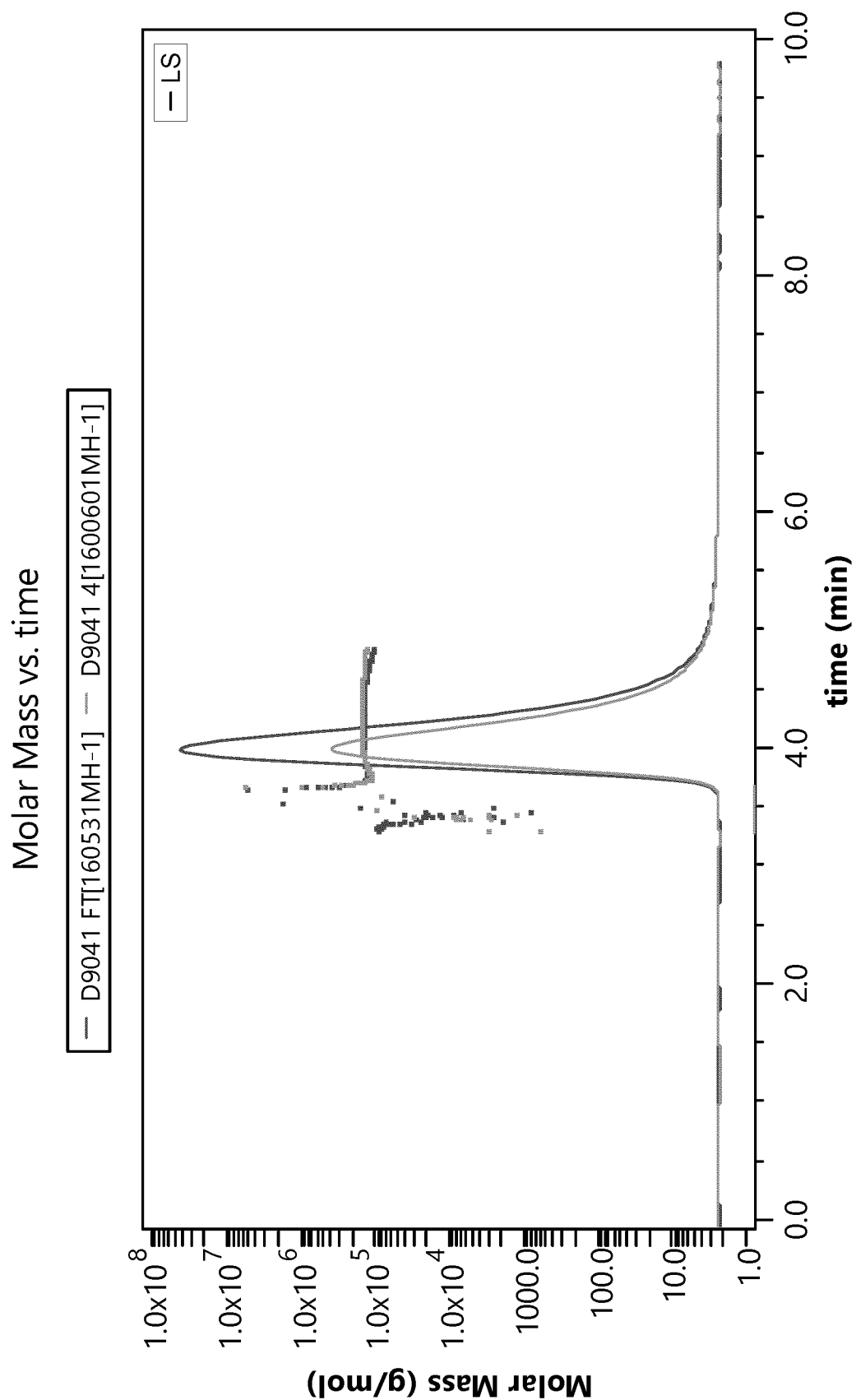
Figure 11C:
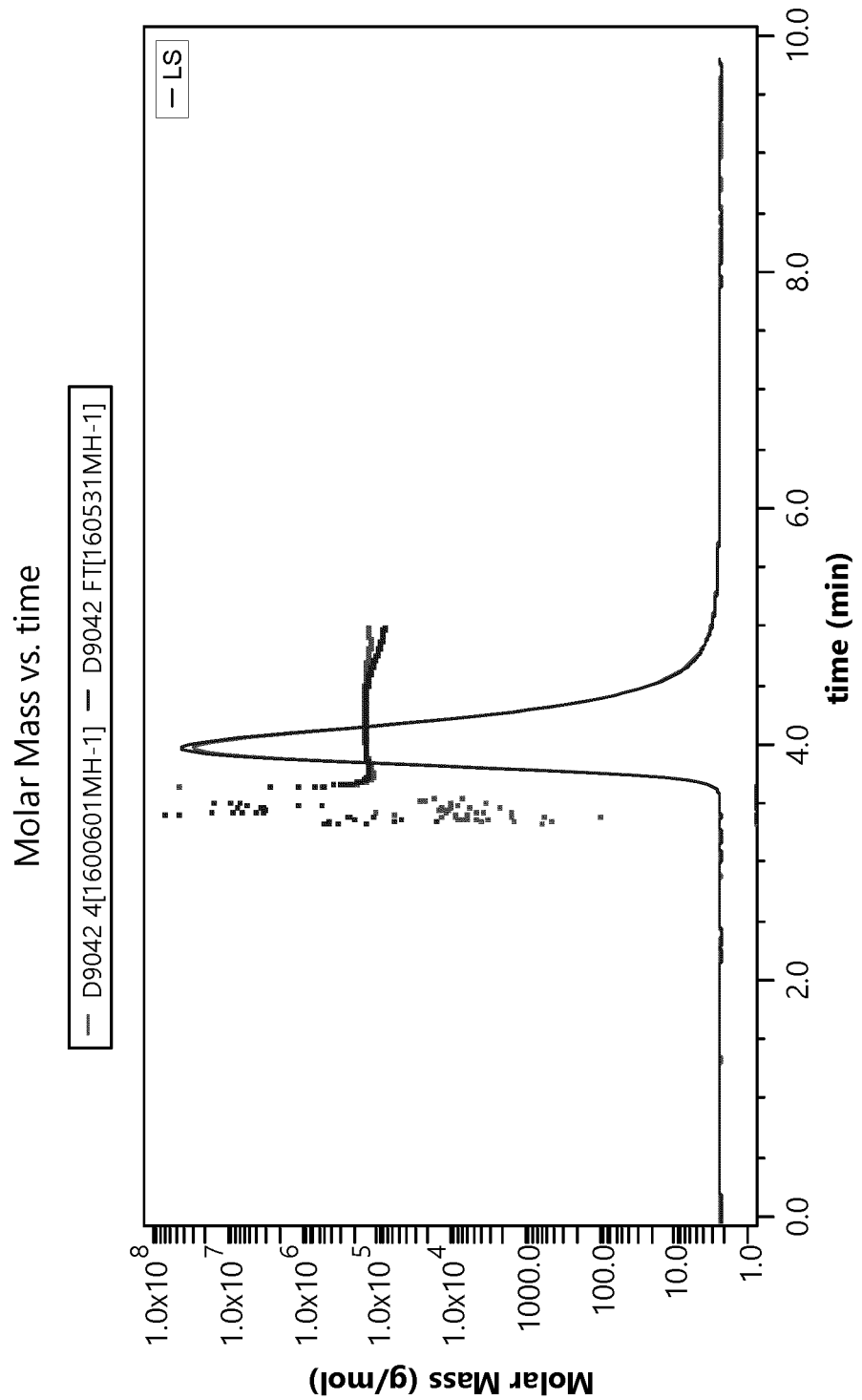

14. Freeze/Thaw Stress Analysis of Humanized hD9040, hD9041 and hD9042 Antibodies Samples of the purified candidate antibodies were subjected to 10 cycles of 15 minutes at −80° C. followed by thawing for 15 minutes at Room Temperature. Samples were then analyzed by SEC-MALS to check for aggregation (FIG. 11). The data suggests that freeze/thaw does not cause aggregation in the humanized antibodies hD9040, hD9041 and hD9042 (FIGS. 11A, 11B and 11C respectively).

Figure 12A:
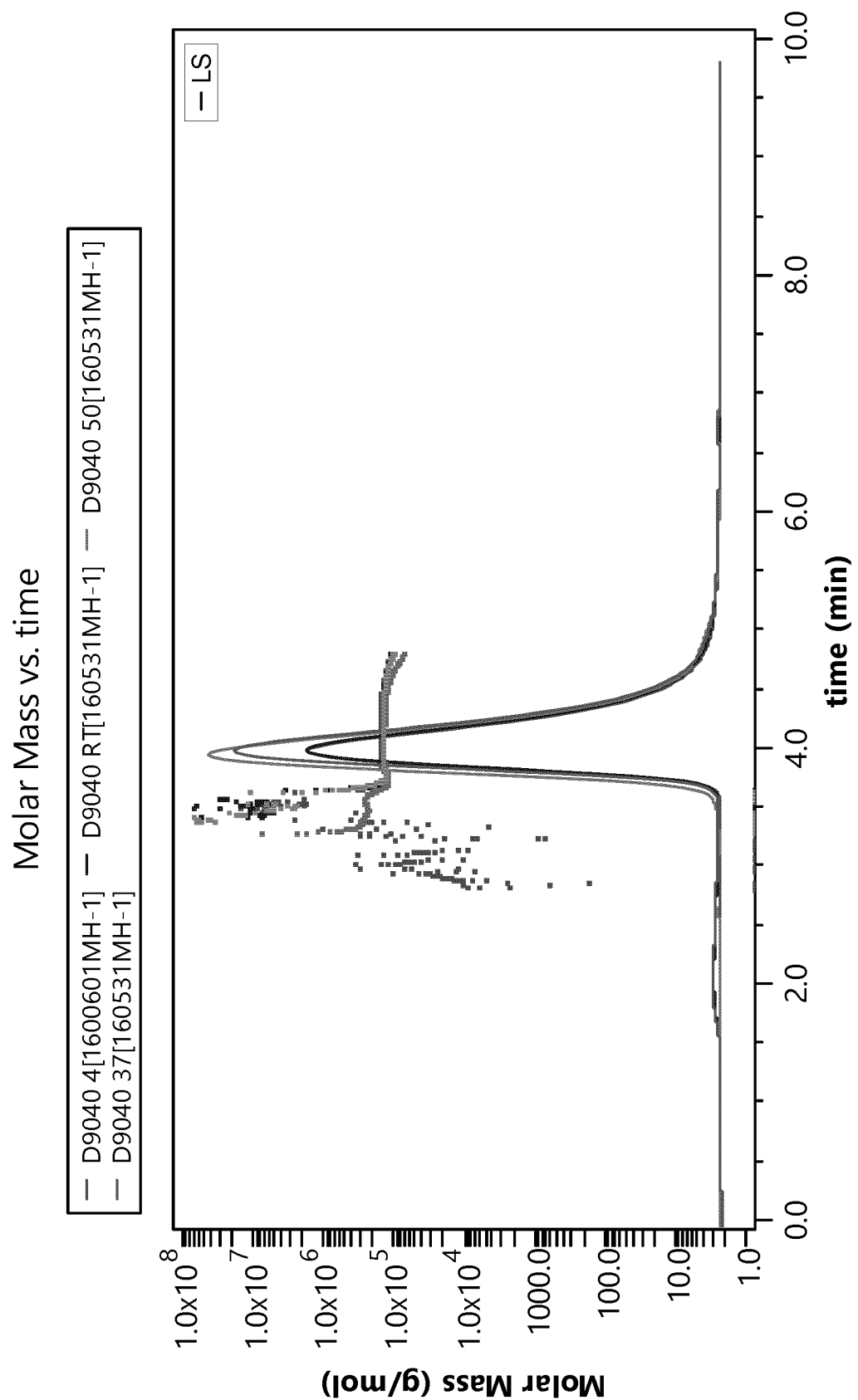
FIG. 12 shows heat induced stress analysis of humanized antibodies hD9040 (12A), hD9041 (12B) and hD9042 (12C).
Figure 12B:
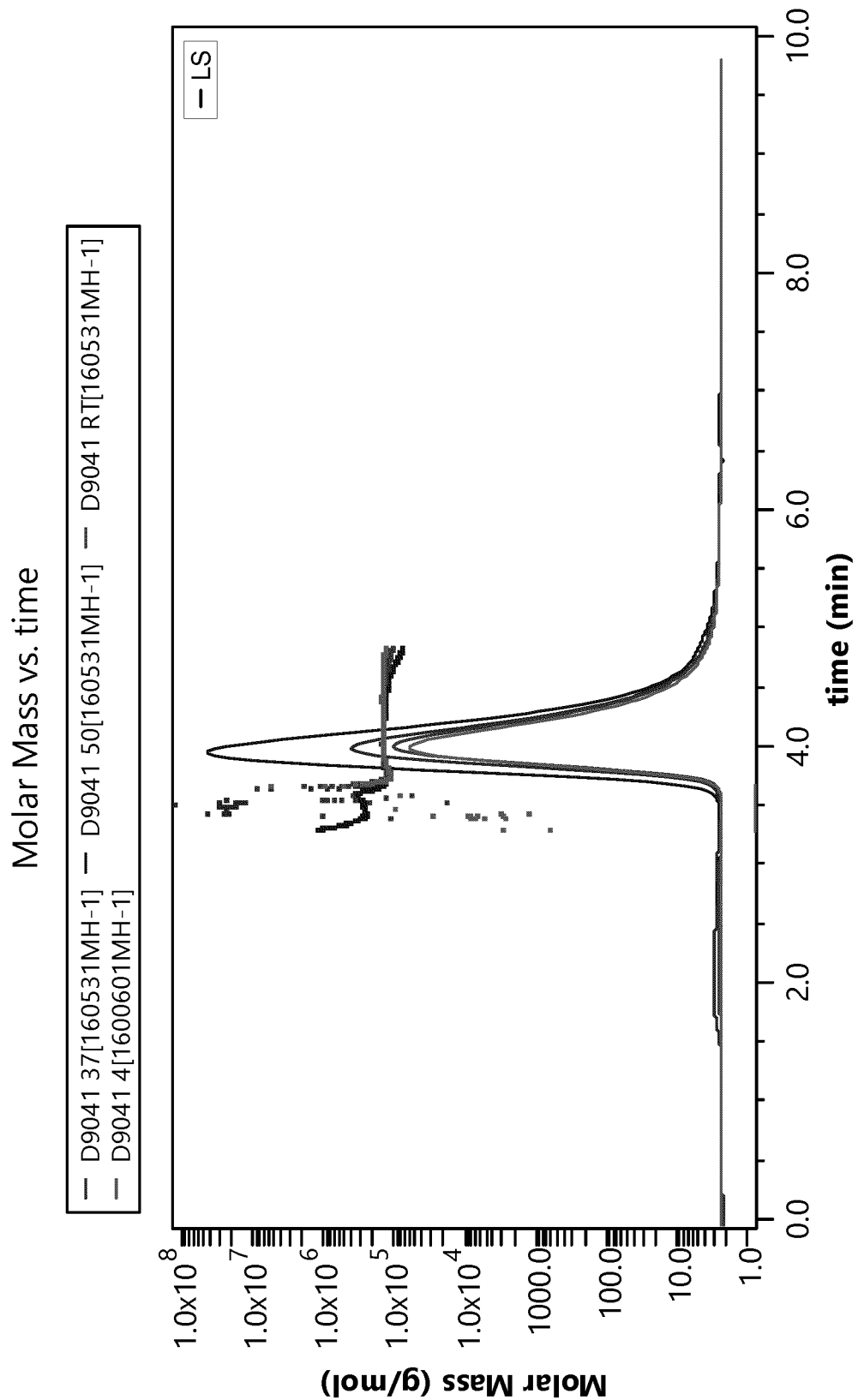
Figure 12C:
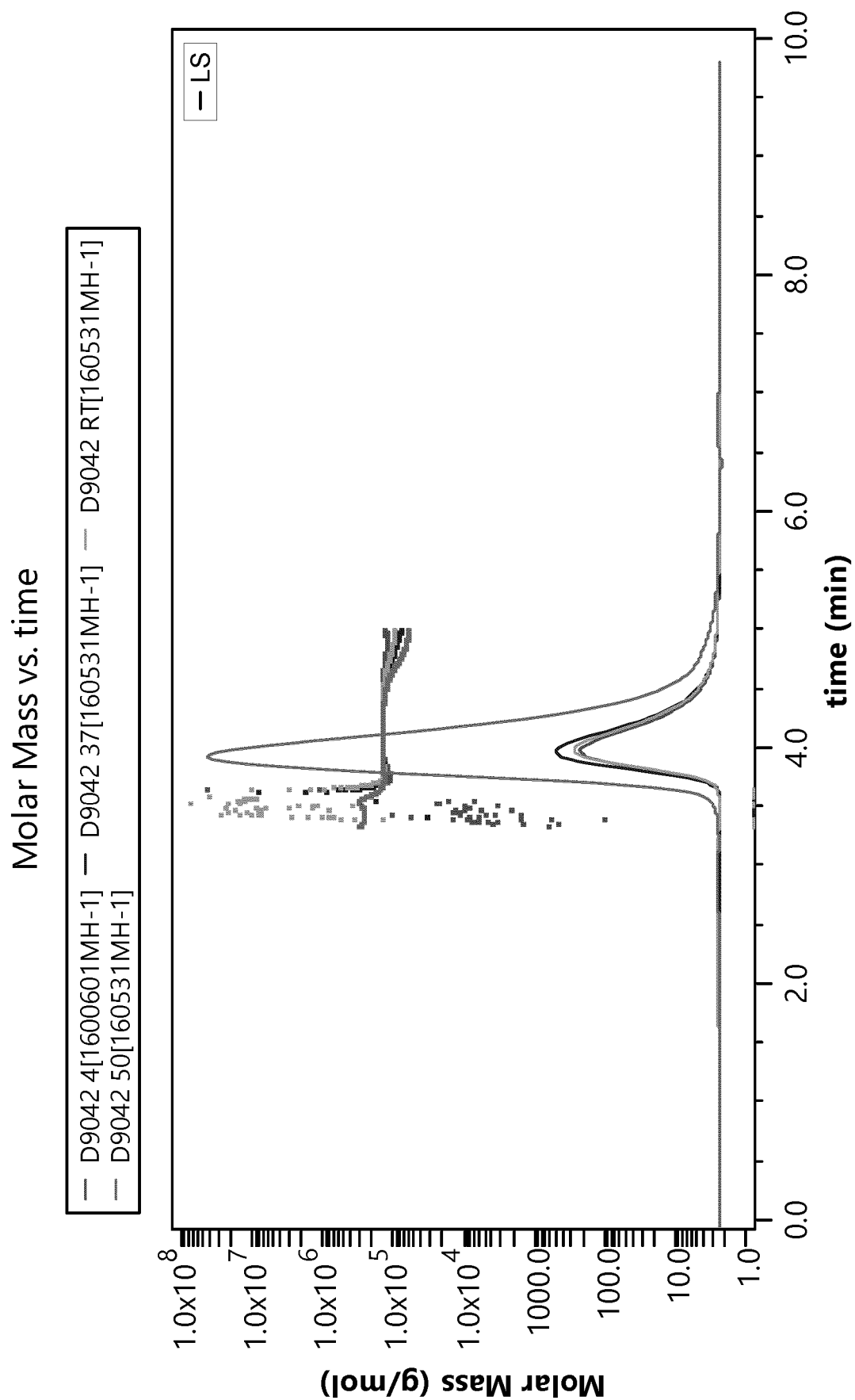

15. Heat-Induced Stress Analysis of Humanized hD9040, hD9041 and hD9042 Antibodies Samples of the purified candidate antibodies were exposed at a) 4° C., b) 25° C., c) 37° C. and d) 50° C. for 33 days. Samples were then analyzed by SEC-MALS to check for aggregation as described in Section 8.19 (FIG. 12). Overall the data suggest there are no aggregation concerns in the humanized antibodies hD9040, hD9041 and hD9042 (FIGS. 12A, 12B and 12C respectively).

16. pI Analysis of Humanized hD9040, hD9041 and hD9042 Antibodies pI analysis of the humanized antibodies hD9040, hD9041 and hD9042 was performed using capillary isoelectric focusing (cIEF). This technique allows antibodies to be separated according to their isoelectric point (pI) using a pH gradient across the capillary. Table 7 displays the main pI isoform of each antibody and the pI range for each antibody. The pI for hD9040 and hD9041 is 7.8 and for hD9042 antibodies is 7.9.

Figure 13:
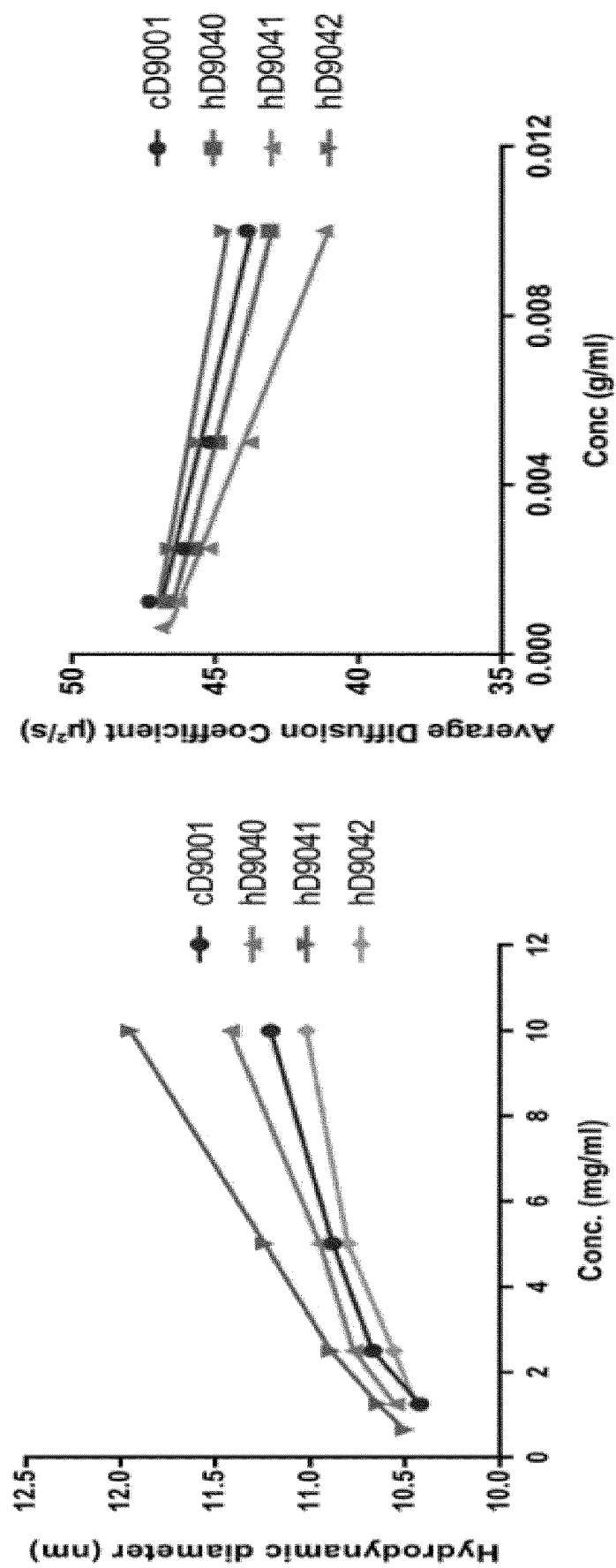
FIG. 13 shows self-association analysis of humanized antibodies hD9040-42 by DLS.

17. Self-Association Analysis by DLS of Humanized hD9040, hD9041 and hD9042 Antibodies Concentrations from 10 mg/ml-0.63 mg/ml with a 2-fold dilution series (5 samples in total) were made for each antibody, hD9040, hD9041 and hD9042. The hydrodynamic diameter and diffusion constant were then determined for each sample using dynamic light scattering (DLS). As shown in FIG. 13, hD9042 has the least propensity to self-associate followed by hD9040 and hD9041.

18. hD9042 Binding Specificity to hIL17 Receptor Family

Figure 14:
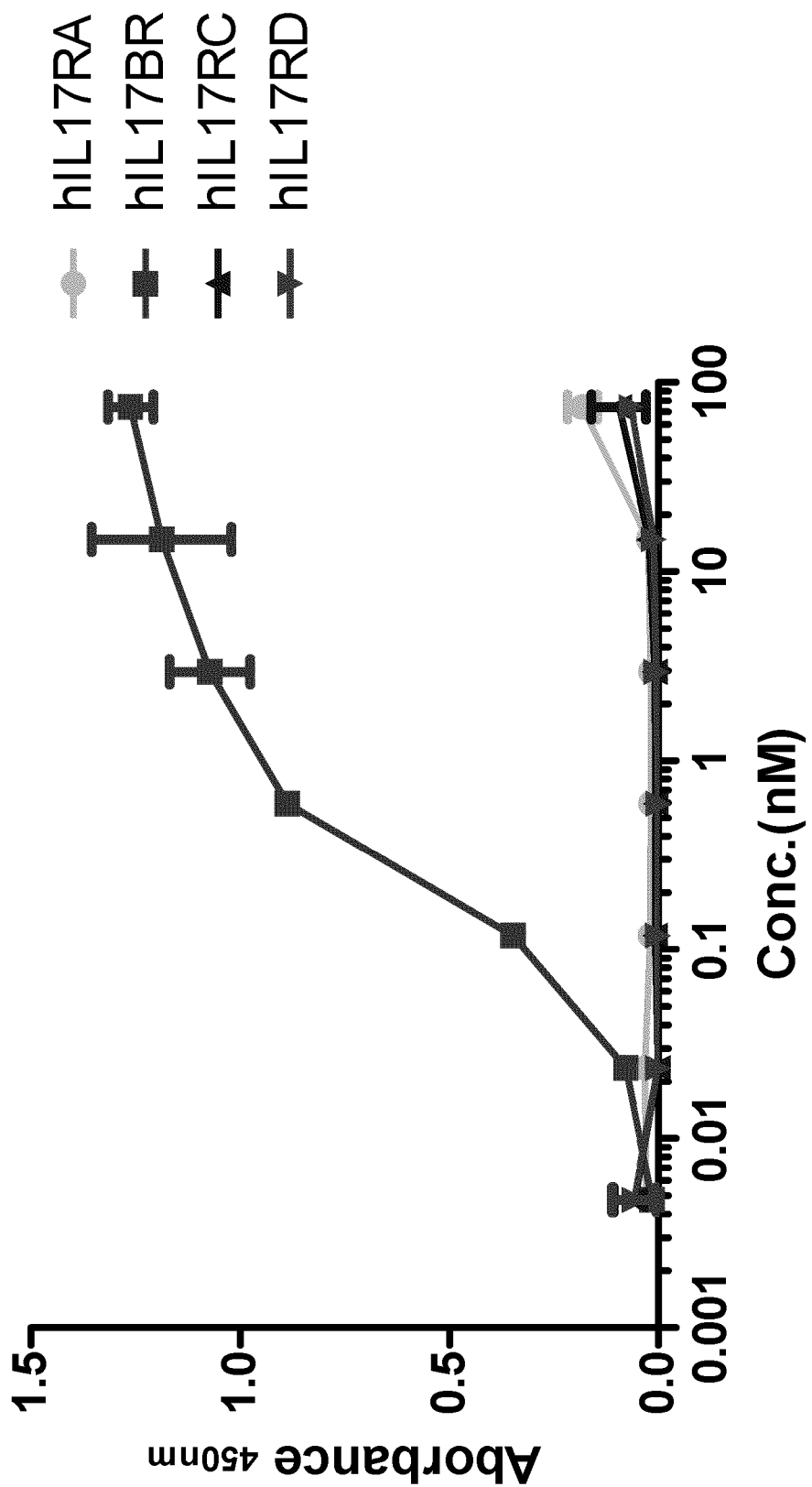
FIG. 14 shows the results of an ELISA assay to determine the binding specificity of the lead candidate hD9042 to human IL17BR relative to human IL17RA, IL17RC and IL17RD.

The binding specificity of the lead candidate hD9042 to human IL17BR was determined by ELISA. hD9042 was found to specifically bind to human IL17BR but did not cross-react with human IL17RA, IL17RC and IL17RD (FIG. 14).

19. In Vitro Human IL-5 and IL-13 Cytokine Production Assay

Figure 15A:
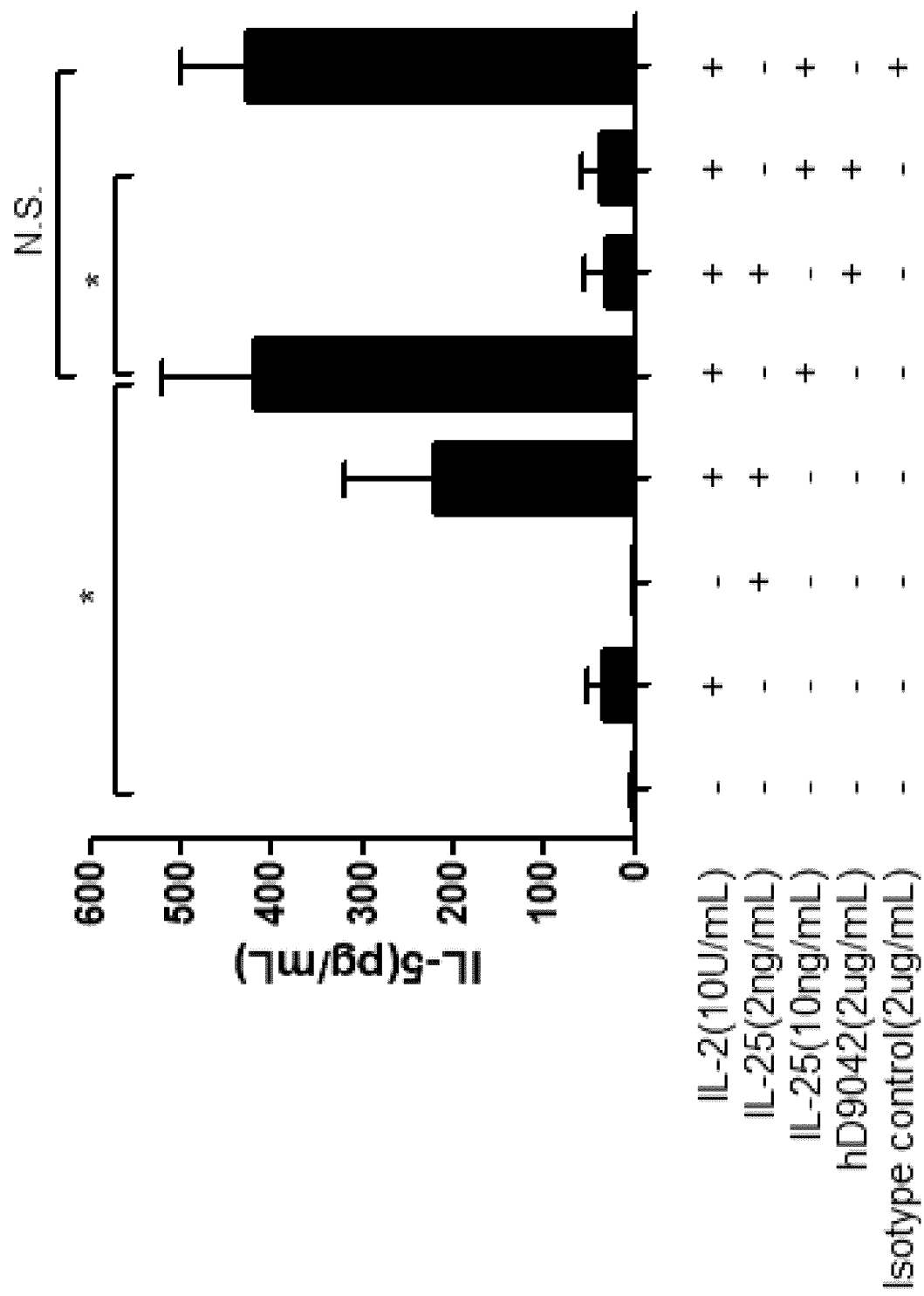
FIG. 15 shows the results of an assay for the induction of human IL-5 (FIG. 15A) and IL-13 (FIG. 15B) by IL-25 and IL-2 in the presence of hD9042
Figure 15B:
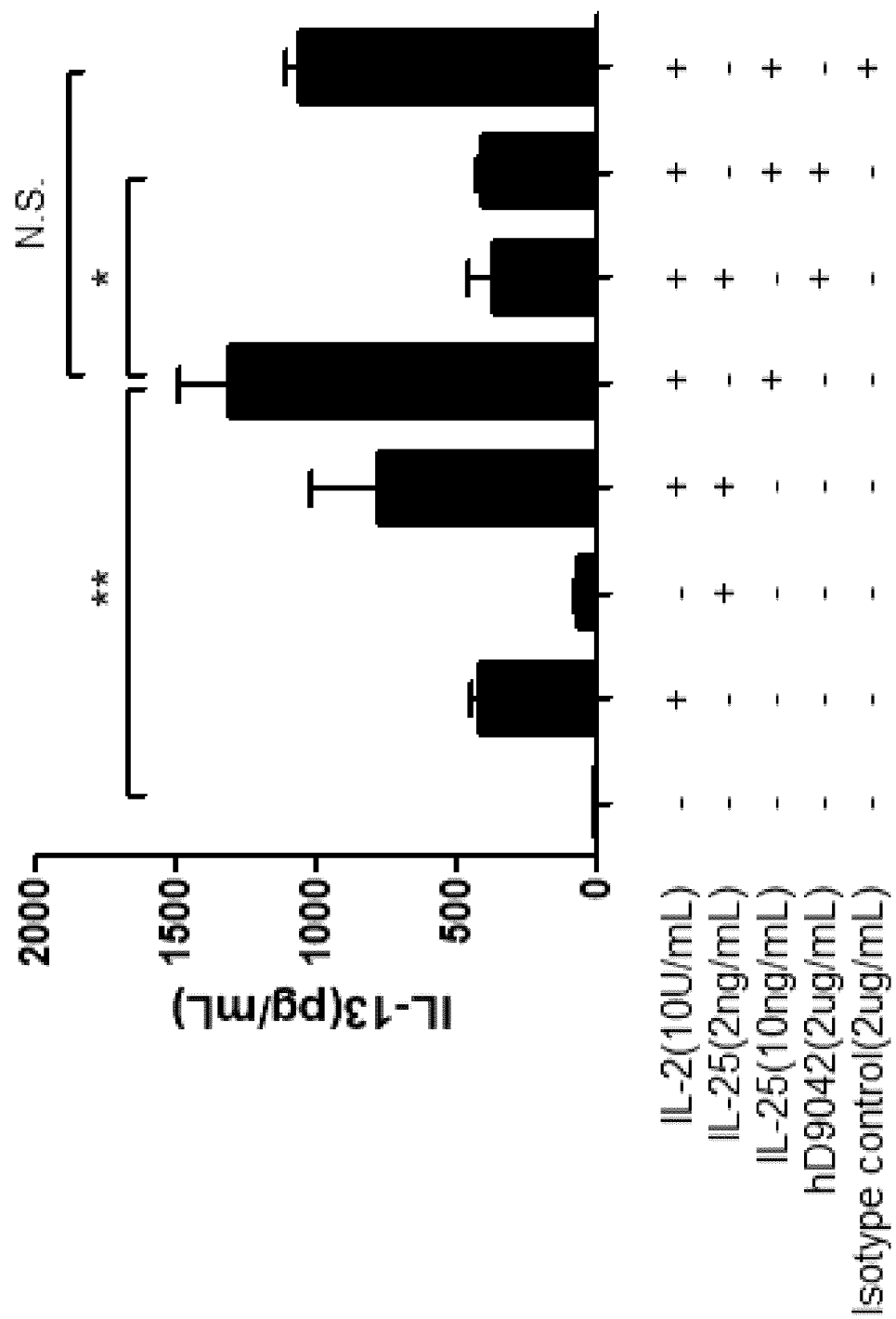

In the presence of IL-2, IL-25 significantly induces human PBMC to produce type 2 cytokines (IL-5 and IL-13). hD9042 blocked the IL-25 induced production of IL-5 (FIG. 15A) and IL-13 (FIG. 15B). Statistical significance is depicted as N.S. ($p>0.05$), $*p\leq0.05$, $**p\leq0.01$ (by non-paired two-tailed Student's t test).

20. Generation of hD9043, Hinge-Stabilized IgG4 Antibody

To minimize the effector functions of Fc region, D9HJ was fused to IgG4 constant region to produce D9HJ-IgG4*. To inhibit Fab-arm exchange and stabilize hinge region, point mutation was introduced to mutate serine at position 228 to proline (EU numbering system) (Angal, S. 1993 Mol Immunol, 30:105-108; Aalberse et al. 2002 Immunol, 105: 9-19). The sequence of D9HJ-IgG4* is shown in SEQ ID NO: 17. The sequences of D9HJ-IgG4* were then optimized by silent mutagenesis to use codons preferentially utilized by human cells and synthesized by GenScript. To generate hD9043, D9HJ-IgG4* were inserted into pcDNA3.1 vector and co-transfected with D9KE to ExpiCHO cells. hD9043 were purified using affinity and size-exclusion chromatography.

21. In Vitro Human IL-8 Cytokine Production Assay

Figure 16:
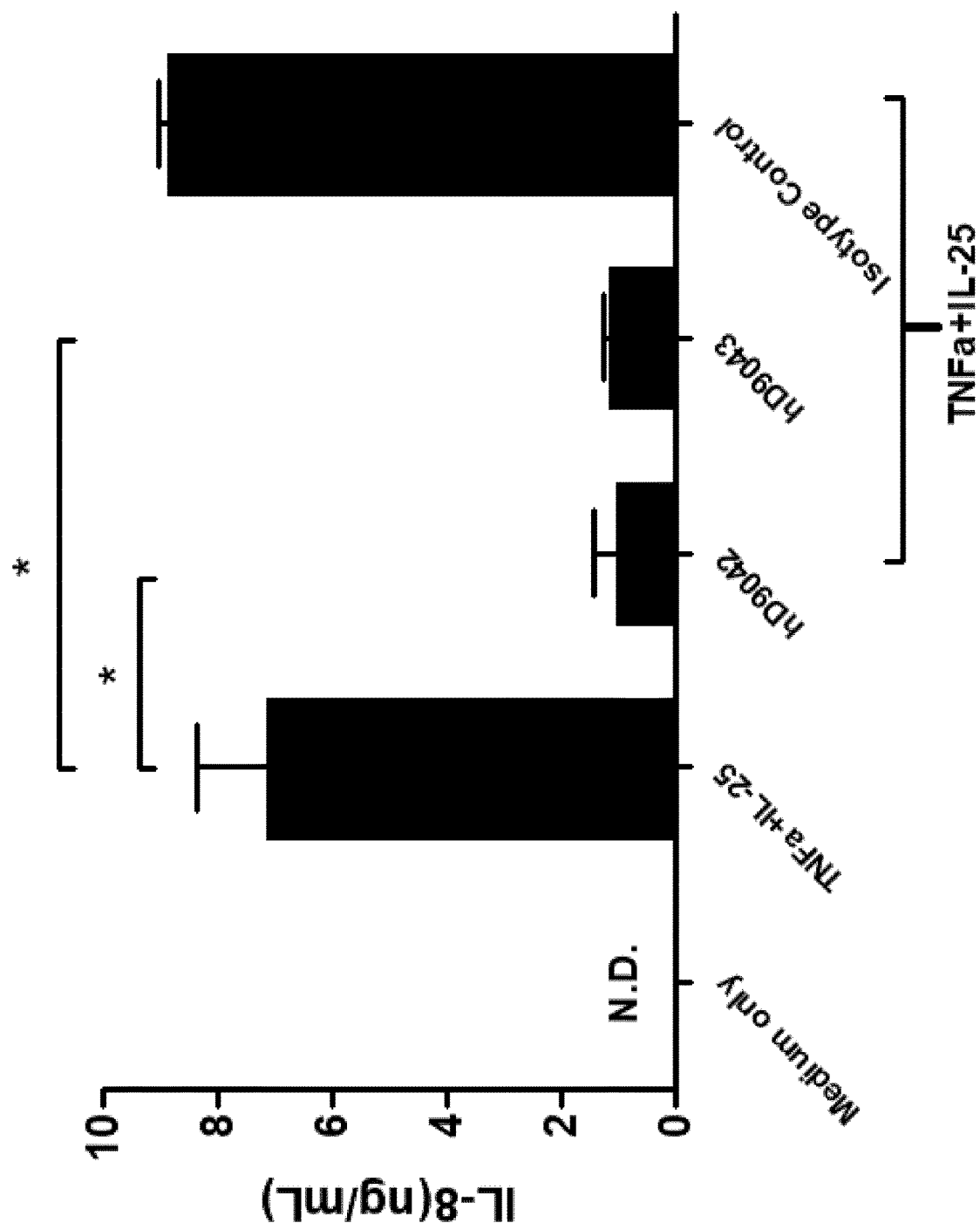
FIG. 16 shows the results of an assay for the induction of human IL-8 by IL-25 and TNFα in the presence of hD9042 or hD9043

IL-25 combined with TNFα could induce the production of IL-8 from TK-10 cells. IL-8 production could be significantly blocked by hD9042 and hD9043 (FIG. 16). Statistical significance is depicted as $*p\leq0.05$, N.D., not-detected.

Summary of Data for hD9040-42 Compared to cD9001

Table 8 shows a summary of the binding, kinetic affinity and biophysical properties of the humanized hD9040, hD9041 and hD9042 humanised candidates. Taking all the data into account, hD9042 was chosen as the lead humanized candidate as it has the slowest off-rate, is the most stable, has the least propensity to self-associate and shows the best expression level of the three candidates.

The D9.2 antibody was humanized and the resulting antibodies retained binding to IL-17BR and had good biophysical properties. The antibodies were engineered and expressed as fully humanized antibodies without significant loss of binding potency. Experiments with the humanized antibodies, hD9040, hD9041 and hD9042 showed high affinities in binding ELISAs and kinetic studies using Biacore, in the low picomolar range (FIGS. 4 and 5). The initial experiments showed that the CDR grafted KA light chain antibodies did not express well but simple re-engineering of the light chain resulted in greatly improved expression of the antibody. The heavy chain was successfully engineered to have >85% identity to human germline so can be referred to as a 'humanized antibody' according to new regulations. The hD9042 antibody shows the best drug-like characteristics as well as excellent kinetics of binding so was chosen as the lead candidate (Table 8). The combination of the excellent binding, expression, thermostability and affinity makes hD9042, a suitable candidate antibody for further development.

```
Sequences

SEQ ID NO: 1
SYWMN

VHCDR1
                                                                        SEQ ID NO: 2
RIDPYDSEIQYX₁QKFX₂X₃  (X₁ is N or A,  X₂ is K or Q and X₃ is D or G)

VHCDR2
                                                                        SEQ ID NO: 3
SGGFDWFAY

VHCDR3
                                                                        SEQ ID NO: 4
RASENINSNLA

VLCDR1
                                                                        SEQ ID NO: 5
DVTNLAD

VLCDR2
```

```
                                                           SEQ ID NO: 6
QHFWGPPYT

VLCDR3
                                                           SEQ ID NO: 7
EVQLVQSGAEVKKPGASVKVSCKTSGYTFISYWMNWVRQAPGQGLEWMGRIDPYDSEIQYNQKFKDRVTLTRDTSIS

TAYMELSRLRSDDTAVYYCATSGGFDWFAYWGQGTLVTVSS

VH sequence HA (CDRs shaded) (Kabat positions 1, 24, 60, 64, 65, 69 and 94
underlined)
                                                           SEQ ID NO: 8
X1VQLVQSGAEVKKPGASVKVSCKX2GYTFISYWMNWVRQAPGQGLEWMGRIDPYDSEIQYX3QKFX4X5RVT

X6TRDTSISTAYMELSRLRSDDTAVYYCARSGGFDWFAYWGQGTLVTVSS (X1 is Q or E, X2 is A or T, X3 is A or N, X4 is Q or K, X5 is G or D and X6
is M or L)
VH sequence (CDRs shaded) with modifications at Kabat positions 1, 24, 60, 64, 65 and
69
                                                           SEQ ID NO: 9
QVQLVQSGAEVKKPGASVKVSCKTSGYTFISYWMNWVRQAPGQGLEWMGRIDPYDSEIQYNQKFKDRVTMTRDTSIS

TAYMELSRLRSDDTAVYYCARSGGFDWFAYWGQGTLVTVSS

VH sequence HJ (CDRs shaded)
                                                           SEQ ID NO: 10
EVQLVQSGAEVKKPGASVKVSCKTSGYTFISYWMNWVRQAPGQGLEWMGRIDPYDSEIQYNQKFKDRVTLTRDTSIS

TAYMELSRLRSDDTAVYYCARSGGFDWFAYWGQGTLVTVSS

VH sequence HH (CDRs shaded)
                                                           SEQ ID NO: 11
EVQLVQSGAEVKKPGASVKVSCKTSGYTFISYWMNWVRQAPGQGLEWMGRIDPYDSEIQYAQKFQGRVTLTRDTSIS

TAYMELSRLRSDDTAVYYCARSGGFDWFAYWGQGTLVTVSS

VH sequence HI (CDRs shaded)
                                                           SEQ ID NO: 12
DIQMTQSPSSLSASVGDRVTITCRASENINSNLAWYQQKPGKAPKLLLYDVTNLADGVPSRFSGSGSGTDYTLTISS

LQPEDFATYYCQHFWRPPYTFGGGTKVEIK

VL sequence KA (CDRs shaded) (Kabat position 93 underlined)
                                                           SEQ ID NO: 13
DIQMTQSPSSLSASVGDRVTITCRASENINSNLAWYQQKPGKAPKLLLYDVTNLADGVPSRFSGSGSGTDYTLTISS

LQPEDFATYYCQHFWGPPYTFGGGTKVEIK

VL sequence KE (CDRs shaded)
                                                           SEQ ID NO: 14
RIDPYDSEIQYNQKFKD VHCDR2 HJ and HH
                                                           SEQ ID NO: 15
RIDPYDSEIQYAQKFQG VHCDR2 HI
                                                           SEQ ID NO. 16
ASTKGPSVFPLAPCSRSTSESTAALGCLVKDYFPEPVTVSWNSGALTSGVHTFPAVLQSSGLYSLSSVVTVPSSSLG
TKTYTCNVDHKPSNTKVDKRVESKYGPPCPPCPAPEFLGGPSVFLEPPKPKDTLMISRTPEVTCVVVDVSQEDPEVQ
FNWYVDGVEVHNAKTKPREEQFNSTYRVVSVLTVLHQDWLNGKEYKCKVSNKGLPSSIEKTISKAKGQPREPQVYTL
PPSQEEMTKNQVSLTCLVKGFYPSDIAVEWESNGQPENNYKTTPPVLDSDGSFELYSRLTVDKSRWQEGNVESCSVM
HEALHNHYTQKSLSLSLGK Hinge stabilized IgG4 constant region
                                                           SEQ ID NO. 17
QVQLVQSGAEVKKPGASVKVSCKASGYTFISYWMNWVRQAPGQGLEWMGRIDPYDSEIQYNQKFKDRVTMTRDTSIS
TAYMELSRLRSDDTAVYYCARSGGEDWFAYWGQGTLVTVSSASTKGPSVFPLAPCSRSTSESTAALGCLVKDYFPEP
VTVSWNSGALTSGVHTFPAVLQSSGLYSLSSVVTVPSSSLGTKTYTCNVDHKPSNTKVDKRVESKYGPPCPPCPAPE
FLGGPSVFLEPPKPKDTLMISRTPEVTCVVVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEMTKNQVSLTCLVKGFYPSDIAVEWESNGQP
ENNYKTTPPVLDSDGSFELYSRLTVDKSRWQEGNVESCSVMHEALHNHYTQKSLSLSLGK
D9HJ-IgG4* sequence
```

TABLE 1

```
        Sequence
        1         10        20        30        40        50        60        70
        |---:----+----:----+----:----+----:----+----:----+----:----+----:----+---
                  80        90        100       110       120       130       140
Name    -:----+----:----+----:----+----:----+----:----+----:----+----:----+----:-

D9.2 VH QVQLQQPGAELVRPGASVKLSCKTSGYTFIS----YWMNWVKQGPEQGLEWIGRIDPYD---SEIQYNQKFKD
        KAILTVDKSSSAAYMQLISLTSEDSAVYYCARSGGFDW---------------FAYWGQGTLVTVSA

EF178110 EVQLVESGAEVKKPGASVKVSCKTSGYTFID----YYIHWVRQAPGQGLEWMGWINPKS---GGTNYARNLRD
        RVTLTRDTSINTAYMELSRLSDDTALYYCATLYGDYR----------------PIQDSWGQGTLVTVSS

D9 HA   EVQLVESGAEVKKPGASVKVSCKTSGYTFIS----YWMNWVRQAPGQGLEWMGRIDPYD---SEIQYNQKFKD
        RVTLTRDTSISTAYMELSRLSDDTAVYYCATSGGFDW---------------FAYWGQGTLVTVSS

D9 HB   EVQLVESGAEVKKPGASVKVSCKTSGYTFIS----YWMNWVRQAPGQGLEWIGRIDPYD---SEIQYNQKFKD
        KAILTVDTSISTAYMELSRLSDDTAVYYCARSGGFDW---------------FAYWGQGTLVTVSS

D9 HC   EVQLVESGAEVKKPGASVKVSCKTSGYTFIS----YWMNWVRQAPGQGLEWIGRIDPYD---SEIQYNQKFKD
        RVTLTRDTSISTAYMELSRLSDDTAVYYCATSGGFDW---------------FAYWGQGTLVTVSS

D9 HD   EVQLVESGAEVKKPGASVKVSCKTSGYTFIS----YWMNWVRQAPGQGLEWMGRIDPYD---SEIQYNQKFKD
        KVTLTRDTSISTAYMELSRLSDDTAVYYCATSGGFDW---------------FAYWGQGTLVTVSS

D9 HE   EVQLVESGAEVKKPGASVKVSCKTSGYTFIS----YWMNWVRQAPGQGLEWMGRIDPYD---SEIQYNQKFKD
        RATLTRDTSISTAYMELSRLSDDTAVYYCATSGGFDW---------------FAYWGQGTLVTVSS

D9 HF   EVQLVESGAEVKKPGASVKVSCKTSGYTFIS----YWMNWVRQAPGQGLEWMGRIDPYD---SEIQYNQKFKD
        RVILTRDTSISTAYMELSRLSDDTAVYYCATSGGFDW---------------FAYWGQGTLVTVSS

D9 HG   EVQLVESGAEVKKPGASVKVSCKTSGYTFIS----YWMNWVRQAPGQGLEWMGRIDPYD---SEIQYNQKFKD
        RVTLTVDTSISTAYMELSRLSDDTAVYYCATSGGFDW---------------FAYWGQGTLVTVSS

D9 HH   EVQLVESGAEVKKPGASVKVSCKTSGYTFIS----YWMNWVRQAPGQGLEWMGRIDPYD---SEIQYNQKFKD
        RVTLTRDTSISTAYMELSRLSDDTAVYYCARSGGFDW---------------FAYWGQGTLVTVSS

D9 HI   EVQLVESGAEVKKPGASVKVSCKTSGYTFIS----YWMNWVRQAPGQGLEWMGRIDPYD---SEIQYAQKFQG
        RVTLTRDTSISTAYMELSRLSDDTAVYYCARSGGFDW---------------FAYWGQGTLVTVSS

D9 HJ   QVQLVESGAEVKKPGASVKVSCKTSGYTFIS----YWMNWVRQAPGQGLEWMGRIDPYD---SEIQYNQKFKD
        RVTMTRDTSISTAYMELSRLSDDTAVYYCARSGGFDW---------------FAYWGQGTLVTVSS
```

Dotted underline residues indicate back-translations to the Mouse Residue and solid underline residues indicate back-mutations to human germline

TABLE 2

```
        Sequence
        1         10        20        30        40        50        60
        |---:----+----:----+----:----+----:----+----:----+----:----+--
                  70        80        90        100       110
Name    --:----+----:----+----:----+----:----+----:----+----:---

D9.2 VK DIQMTQSPASLSVSVGETVTITCRASENINS-------NLAWYQQKKGKSPQLLVYDVTNLAD
        GVPSRFSGSGSGTQYSLKINSLQSEDFGSYYCQHFWRPP------YTFGGGTNLEIK

Y14869  DIQMTQSPASLSVSVGETVTITCRASQ-------GISNSLAWYQQKKGKAPKLLLYAASRLES
        GVPSRFSGSGSGTDYTLTISSLQPEDFATYYCQQYYSTP------LTFGGGTKVEIK

D9_KA   DIQMTQSPSSLSASVGDRVTITCRASENINS-------NLAWYQQKPGKAPKLLLYDVTNLAD
        GVPSRFSGSGSGTDYTLTISSLQPEDFATYYCQHFWRPP------YTFGGGTKVEIK

D9_KB   DIQMTQSPSSLSASVGDRVTITCRASENINS-------NLAWYQQKPGKAPKLLVYDVTNLAD
        GVPSRFSGSGSGTQYTLTISSLQPEDFATYYCQHFWRPP------YTFGGGTKVEIK

D9_KC   DIQMTQSPSSLSASVGDRVTITCRASENINS-------NLAWYQQKPGKAPKLLVYDVTNLAD
        GVPSRFSGSGSGTDYTLTISSLQPEDFATYYCQHFWRPP------YTFGGGTKVEIK

D9_KD   DIQMTQSPSSLSASVGDRVTITCRASENINS-------NLAWYQQKPGKAPKLLLYDVTNLAD
        GVPSRFSGSGSGTQYTLTISSLQPEDFATYYCQHFWRPP------YTFGGGTKVEIK
```

TABLE 2-continued

```
Sequence
1         10        20        30        40        50        60
|---:----+----:----+----:----+----:----+----:----+----:----+--
          70        80        90        100       110
Name      --:----+----:----+----:----+----:----+----:----+----:---

KM        DIQMTQSPSSLSASVGDRVTITCRTSENIYS------NLAWYQQKPGKAPKLLLYDATNLGD
          GVPSRFSGSGSGTDYTLTISSLQPEDFATYYCQHFWGPP------YTFGGGTKVEIK

D9_KE     DIQMTQSPSSLSASVGDRVTITCRASENINS------NLAWYQQKPGKAPKLLLYDVTNLAD
          GVPSRFSGSGSGTDYTLTISSLQPEDFATYYCQHFWGPP------YTFGGGTKVEIK
```

Dotted underline indicates back-translations to the Mouse Residue and the solid underline indicates the residue identified by molecular modelling.

TABLE 3

| Antibody name | VH | VK | IgG CONCENTRATION IN SUPERNATANT | | IgG Yield mg/L |
|---|---|---|---|---|---|
| | | | HTRF µg/mL | Octet µg/mL | |
| 1210 positive control | 1210 VK ctrl | 1210 VH ctrl | 252 | | |
| cD9001 | D9.2 VH.pHuG1 | D9.2 VK.pHuK | 691 | 7.6 | 88 |
| D9 cHKA | D9.2 VH.pHuG1 | D9_KA.pHuK | / | 4.7 | |
| D9 HAcK | D9_HA.pHuG1 | D9.2 VK.pHuK | 243 | | |
| hD9 HAKA | D9_HA.pHuG1 | D9_KA.pHuK | / | | |
| D9 HBcK | D9_HB.pHuG1 | D9.2 VK.pHuK | 379 | | |
| hD9 HBKA | D9_HB.pHuG1 | D9_KA.pHuK | / | | |
| hD9002 | D9_HA.pHuG1 | KM.pHuK | 48 | | |
| hD9006 | D9_HB.pHuG1 | KM.pHuK | 151 | | |
| hD9010 | D9_HC.pHuG1 | KM.pHuK | 94 | | |
| hD9014 | D9_HD.pHuG1 | KM.pHuK | 189 | | |
| hD9018 | D9_HE.pHuG1 | KM.pHuK | 215 | | |
| hD9022 | D9_HF.pHuG1 | KM.pHuK | 217 | | |
| hD9026 | D9_HG.pHuG1 | KM.pHuK | 272 | | |
| hD9030 | D9_HH.pHuG1 | KM.pHuK | 142 | 40.1 | |
| hD9035 | D9_HH.pHuG1 | D9_KA.pHuK | | 2.6 | |
| hD9036 | D9_HI.pHuG1 | D9_KA.pHuK | | 4.5 | |
| hD9037 | D9_HJ.pHuG1 | D9_KA.pHuK | | 6.5 | |
| D9 cHKE | D9.2 VH.pHuG1 | D9_KE.pHuK | 47.2 | | |
| hD9040 | D9_HH.pHuG1 | D9_KE.pHuK | 30 | 15 | |
| hD9041 | D9_HI.pHuG1 | D9_KE.pHuK | 88 | 40 | |
| hD9042 | D9_HJ.pHuG1 | D9_KE.pHuK | 97 | 46 | |

TABLE 4

| Ranked based on $K_{off}$ | $K_{off}$ |
|---|---|
| D9_cHKM | 5.65E-05 |
| hD9030 | 8.27E-05 |
| D9_HBcK | 1.01E-04 |
| hD9006 | 1.03E-04 |
| hD9010 | 1.21E-04 |
| cD9001 | 1.18E-04 |
| hD9022 | 1.58E-04 |
| hD9014 | 1.88E-04 |
| hD9018 | 1.92E-04 |
| hD9026 | 2.25E-04 |
| hD9002 | 2.46E-04 |
| D9_HAcK | 3.21E-04 |

TABLE 5

| | Tm 1 (° C.) | Tm 2 (° C.) | Av. Tm (° C.) |
|---|---|---|---|
| hD9040 (1 µM) | 69 | 78 | 74 |
| hD9040 (2 µM) | 69 | 78 | |
| hD9041 (1 µM) | 68 | 76 | 72 |
| hD9041 (2 µM) | 68 | 76 | |
| hD9042 (1 µM) | 68 | 79 | 74 |
| hD9042 (2 µM) | 68 | 79 | |
| cD9001 (1 µM) | 68 | 82 | 75 |
| cD9001 (2 µM) | 68 | 82 | |

TABLE 6

| | Mw (kDa) | Polydispersity | Mass fraction (%) |
|---|---|---|---|
| hD9040 | 131.04 | 1.00 | 100.00 |
| hD9041 | 132.34 | 1.00 | 100.00 |
| hD9042 | 131.92 | 1.00 | 100.00 |

TABLE 7

| Sample | pI range | Main Isoform |
|---|---|---|
| hD9040 | 7.4-7.8 | 7.8 (49%) |
| hD9041 | 7.4-7.8 | 7.8 (41%) |
| hD9042 | 7.4-8.2 | 7.9 (58%) |

TABLE 8

|  | cD9001 | hD9040 | hD9041 | hD9042 |
| --- | --- | --- | --- | --- |
| Expression | 87.5 mg/L | 15 mg/L | 39.6 mg/L | 45.6 mg/L |
| ka (1/Ms) | 2.90E+06 | 3.42E+06 | 3.89E+06 | 4.85E+06 |
| kd (1/s) | 5.00E−05 | 6.66E−05 | 4.44E−05 | 8.23E−05 |
| $K_D$ (pM) | 17 | 20 | 11 | 17 |
| pI range | 7.1-7.35 | 7.4-7.8 | 7.4-7.8 | 7.4-8.2 |
| Average Tm (° C.) | 76 | 74 | 72 | 74 |
| Thermal stability | >70° C. | <73° C. | <73° C. | <75° C. |
| Solubility | ≥50 mg/ml | ≥50 mg/ml | ≥50 mg/ml | ≥50 mg/ml |
| Mass fraction (%) - 50° C. incubation | 100 | 100 | 100 | 100 |
| Mass fraction (%) - repeated freeze-thaw | 100 | 100 | 100 | 100 |
| Non-specific interactions | 0.15-Pass | 0.15-Pass | 0.13-Pass | 0.11-Pass |
| DLS self-association $k_D$ | −0.36 | −0.39 | −0.59 | −0.28 |

The invention claimed is:

1. An antibody that specifically binds to interleukin-17 receptor B (IL17BR), the antibody comprising a heavy chain variable domain and a light chain variable domain, wherein
a) the heavy chain variable domain comprises a VHCDR1 of SEQ ID NO: 1, a VHCDR2 of SEQ ID NO: 2, and a VHCDR3 of SEQ ID NO: 3, and
b) the light chain variable domain comprises a VLCDR1 of SEQ ID NO: 4, a VLCDR2 of SEQ ID NO: 5, and a VLCDR3 of SEQ ID NO: 6.

2. An antibody according to claim 1 wherein the antibody binds to interleukin-17 receptor with a binding affinity of at least 75% of the binding affinity of the murine antibody D9.2 to interleukin-17 receptor B, as measured by ELISA, wherein the murine antibody D9.2 comprises a heavy chain variable domain of SEQ ID NO: 18 and a light chain variable domain of SEQ ID NO: 26.

3. An antibody according to claim 1 wherein the expression level of the antibody is at least 40% of the expression level of the murine antibody D9.2 in mammalian cells, wherein the murine antibody D9.2 comprises a heavy chain variable domain of SEQ ID NO: 18 and a light chain variable domain of SEQ ID NO: 26.

4. An antibody according to claim 1 wherein the heavy chain variable domain comprises SEQ ID NO: 8, optionally with up to four additional framework substitutions.

5. An antibody according to claim 4 wherein the heavy chain variable domain (VH) comprises SEQ ID NO: 9.

6. An antibody according to claim 4 wherein the heavy chain variable domain comprises SEQ ID NO: 10.

7. An antibody according to claim 4 wherein the heavy chain variable domain comprises SEQ ID NO: 11.

8. An antibody according to claim 1 wherein the heavy chain variable domain is fused to an antibody constant region comprising SEQ ID NO: 16.

9. An antibody according to claim 8 wherein the amino acid sequence of the heavy chain variable domain and constant region comprises SEQ ID NO: 17.

10. An antibody according to claim 1 wherein the light chain variable domain comprises SEQ ID NO: 13, optionally with up to four additional framework substitutions.

11. An antibody according to claim 1 further comprising a second heavy chain variable domain and a second light chain variable domain which form an antigen binding site for an antigen other than IL17BR.

12. A pharmaceutical composition comprising an antibody according to claim 1 and a pharmaceutically acceptable carrier.

13. A nucleic acid encoding an antibody of claim 1.

14. A vector comprising the nucleic acid of claim 13 operably linked to a promoter.

15. A host cell comprising the nucleic acid of claim 13 or vector comprising said nucleic acid.

16. A method for making an antibody according to claim 1, the method comprising expressing, in a host cell culture, a vector comprising a nucleic acid encoding said antibody to produce said antibody; and recovering the antibody from the cell culture.

17. A method of treatment of a cancer or an allergic or inflammatory condition by administering, to an individual in need of treatment, an effective amount of an antibody according to claim 1, or a pharmaceutical composition comprising said antibody and a pharmaceutically acceptable carrier,
wherein the cancer or allergic or inflammatory condition is characterized by IL-17BR expression.

18. A method of treatment according to claim 17 wherein the allergic or inflammatory condition is asthma, ulcerative colitis or fibrosis.

19. A method of treatment according to claim 18 wherein the asthma is allergic asthma or rhinovirus exacerbated asthma.

20. A method of treatment according to claim 18 wherein the fibrosis is idiopathic pulmonary fibrosis.

21. A method of treatment according to claim 17 wherein the cancer condition is breast cancer or pancreatic cancer.

* * * * *

SEQUENCE LISTING

<160> NUMBER OF SEQ ID NOS: 31

<210> SEQ ID NO 1
<211> LENGTH: 5
<212> TYPE: PRT
<213> ORGANISM: Artificial Sequence
<220> FEATURE:
<223> OTHER INFORMATION: VHCDR1

<400> SEQUENCE: 1

Ser Tyr Trp Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: VHCDR2
<220> FEATURE:
<221> NAME/KEY: MISC_FEATURE
<222> LOCATION: (12)..(12)
<223> OTHER INFORMATION: Xaa = N or A
<220> FEATURE:
<221> NAME/KEY: MISC_FEATURE
<222> LOCATION: (16)..(16)
<223> OTHER INFORMATION: Xaa = K or Q
<220> FEATURE:
<221> NAME/KEY: MISC_FEATURE
<222> LOCATION: (17)..(17)
<223> OTHER INFORMATION: Xaa = D or G

<400> SEQUENCE: 2

Arg Ile Asp Pro Tyr Asp Ser Glu Ile Gln Tyr Xaa Gln Lys Phe Xaa
1               5                   10                  15

Xaa

<210> SEQ ID NO 3
<211> LENGTH: 9
<212> TYPE: PRT
<213> ORGANISM: Artificial Sequence
<220> FEATURE:
<223> OTHER INFORMATION: VHCDR3

<400> SEQUENCE: 3

Ser Gly Gly Phe Asp Trp Phe Ala Tyr
1               5

<210> SEQ ID NO 4
<211> LENGTH: 11
<212> TYPE: PRT

```
<213> ORGANISM: Artificial Sequence
<220> FEATURE:
<223> OTHER INFORMATION: VLCDR1

<400> SEQUENCE: 4

Arg Ala Ser Glu Asn Ile Asn Ser Asn Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: VLCDR2

<400> SEQUENCE: 5

Asp Val Thr Asn Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: VLCDR3

<400> SEQUENCE: 6

Gln His Phe Trp Gly Pro Pro Tyr Thr
1               5

<210> SEQ ID NO 7
<211> LENGTH: 118
<212> TYPE: PRT
<213> ORGANISM: Artificial Sequence
<220> FEATURE:
<223> OTHER INFORMATION: VH sequence HA

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Ser Tyr
                20                  25                  30

Trp Met Asn Trp Val Arg Gln Ala Pro Gly Gln Gly Leu Glu Trp Met
            35                  40                  45

Gly Arg Ile Asp Pro Tyr Asp Ser Glu Ile Gln Tyr Asn Gln Lys Phe
        50                  55                  60

Lys Asp Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Thr Ser Gly Gly Phe Asp Trp Phe Ala Tyr Trp Gly Gln Gly Thr
                100                 105                 110

Leu Val Thr Val Ser Ser
            115

<210> SEQ ID NO 8
<211> LENGTH: 118
<212> TYPE: PRT
<213> ORGANISM: Artificial Sequence
<220> FEATURE:
<223> OTHER INFORMATION: VH sequence
<220> FEATURE:
<221> NAME/KEY: MISC_FEATURE
<222> LOCATION: (1)..(1)
```

<223> OTHER INFORMATION: Xaa = Q or E
<220> FEATURE:
<221> NAME/KEY: MISC_FEATURE
<222> LOCATION: (24)..(24)
<223> OTHER INFORMATION: Xaa = A or T
<220> FEATURE:
<221> NAME/KEY: MISC_FEATURE
<222> LOCATION: (61)..(61)
<223> OTHER INFORMATION: Xaa = A or N
<220> FEATURE:
<221> NAME/KEY: MISC_FEATURE
<222> LOCATION: (65)..(65)
<223> OTHER INFORMATION: Xaa = Q or K
<220> FEATURE:
<221> NAME/KEY: MISC_FEATURE
<222> LOCATION: (66)..(66)
<223> OTHER INFORMATION: Xaa = G or D
<220> FEATURE:
<221> NAME/KEY: MISC_FEATURE
<222> LOCATION: (70)..(70)
<223> OTHER INFORMATION: Xaa = M or L

<400> SEQUENCE: 8

```
Xaa Val Gln Leu Val Gln Ser Gly Ala Glu Val Lys Lys Pro Gly Ala
1               5                   10                  15

Ser Val Lys Val Ser Cys Lys Xaa Ser Gly Tyr Thr Phe Ile Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Ile Gln Tyr Xaa Gln Lys Phe
    50                  55                  60

Xaa Xaa Arg Val Thr Xaa Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Phe Asp Trp Phe Ala Tyr Trp Gly Gln Gly Thr
            100                 105                 110

Leu Val Thr Val Ser Ser
            115
```

<210> SEQ ID NO 9
<211> LENGTH: 118
<212> TYPE: PRT
<213> ORGANISM: Artificial Sequence
<220> FEATURE:
<223> OTHER INFORMATION: VH sequence HJ

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Ile Gln Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Phe Asp Trp Phe Ala Tyr Trp Gly Gln Gly Thr
            100                 105                 110
```

```
Leu Val Thr Val Ser Ser
        115

<210> SEQ ID NO 10
<211> LENGTH: 118
<212> TYPE: PRT
<213> ORGANISM: Artificial Sequence
<220> FEATURE:
<223> OTHER INFORMATION: VH sequence HH

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Ile Gln Tyr Asn Gln Lys Phe
    50                  55                  60

Lys Asp Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Phe Asp Trp Phe Ala Tyr Trp Gly Gln Gly Thr
            100                 105                 110

Leu Val Thr Val Ser Ser
        115

<210> SEQ ID NO 11
<211> LENGTH: 118
<212> TYPE: PRT
<213> ORGANISM: Artificial Sequence
<220> FEATURE:
<223> OTHER INFORMATION: VH sequence HI

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Ile Gln Tyr Ala Gln Lys Phe
    50                  55                  60

Gln Gly Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Phe Asp Trp Phe Ala Tyr Trp Gly Gln Gly Thr
            100                 105                 110

Leu Val Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: VL sequence KA
```

```
<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Asn Ser Asn
            20                  25                  30

Leu Ala Trp Tyr Gln Gln Lys Pro Gly Lys Ala Pro Lys Leu Leu Leu
        35                  40                  45

Tyr Asp Val Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Arg Pro Pro Tyr
                85                  90                  95

Thr Phe Gly Gly Gly Thr Lys Val Glu Ile Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: VL sequence KE

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Asn Ser Asn
            20                  25                  30

Leu Ala Trp Tyr Gln Gln Lys Pro Gly Lys Ala Pro Lys Leu Leu Leu
        35                  40                  45

Tyr Asp Val Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Pro Pro Tyr
                85                  90                  95

Thr Phe Gly Gly Gly Thr Lys Val Glu Ile Lys
            100                 105

<210> SEQ ID NO 14
<211> LENGTH: 17
<212> TYPE: PRT
<213> ORGANISM: Artificial Sequence
<220> FEATURE:
<223> OTHER INFORMATION: VHCDR2 HJ and HH

<400> SEQUENCE: 14

Arg Ile Asp Pro Tyr Asp Ser Glu Ile Gln Tyr Asn Gln Lys Phe Lys
1               5                   10                  15

Asp

<210> SEQ ID NO 15
<211> LENGTH: 17
<212> TYPE: PRT
<213> ORGANISM: Artificial Sequence
<220> FEATURE:
<223> OTHER INFORMATION: VHCDR2 HI
```

-continued

<400> SEQUENCE: 15

Arg Ile Asp Pro Tyr Asp Ser Glu Ile Gln Tyr Ala Gln Lys Phe Gln
1               5                   10                  15

Gly

<210> SEQ ID NO 16
<211> LENGTH: 327
<212> TYPE: PRT
<213> ORGANISM: Artificial Sequence
<220> FEATURE:
<223> OTHER INFORMATION: Hinge stabilized IgG4 constant region

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

```
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 17
<211> LENGTH: 445
<212> TYPE: PRT
<213> ORGANISM: Artificial Sequence
<220> FEATURE:
<223> OTHER INFORMATION: D9HJ-IgG4* sequence

<400> SEQUENCE: 17

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Ile Ser Tyr
                20                  25                  30

Trp Met Asn Trp Val Arg Gln Ala Pro Gly Gln Gly Leu Glu Trp Met
            35                  40                  45

Gly Arg Ile Asp Pro Tyr Asp Ser Glu Ile Gln Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Phe Asp Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335
```

```
Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 18
<211> LENGTH: 118
<212> TYPE: PRT
<213> ORGANISM: Artificial Sequence
<220> FEATURE:
<223> OTHER INFORMATION: D9.2 VH

<400> SEQUENCE: 18

Gln Val Gln Leu Gln Gln Pro Gly Ala Glu Leu Val Arg Pro Gly Ala
1               5                   10                  15

Ser Val Lys Leu Ser Cys Lys Thr Ser Gly Tyr Thr Phe Ile Ser Tyr
            20                  25                  30

Trp Met Asn Trp Val Lys Gln Gly Pro Glu Gln Gly Leu Glu Trp Ile
        35                  40                  45

Gly Arg Ile Asp Pro Tyr Asp Ser Glu Ile Gln Tyr Asn Gln Lys Phe
    50                  55                  60

Lys Asp Lys Ala Ile Leu Thr Val Asp Lys Ser Ser Ala Ala Tyr
65                  70                  75                  80

Met Gln Leu Ile Ser Leu Thr Ser Glu Asp Ser Ala Val Tyr Tyr Cys
                85                  90                  95

Ala Arg Ser Gly Gly Phe Asp Trp Phe Ala Tyr Trp Gly Gln Gly Thr
            100                 105                 110

Leu Val Thr Val Ser Ala
        115

<210> SEQ ID NO 19
<211> LENGTH: 120
<212> TYPE: PRT
<213> ORGANISM: Artificial Sequence
<220> FEATURE:
<223> OTHER INFORMATION: EF178110

<400> SEQUENCE: 19

Glu Val Gln Leu Val Glu Ser Gly Ala Glu Val Lys Lys Pro Gly Ala
1               5                   10                  15

Ser Val Lys Val Ser Cys Lys Thr Ser Gly Tyr Thr Phe Ile Asp Tyr
            20                  25                  30

Tyr Ile His Trp Val Arg Gln Ala Pro Gly Gln Gly Leu Glu Trp Met
        35                  40                  45

Gly Trp Ile Asn Pro Lys Ser Gly Gly Thr Asn Tyr Ala Arg Asn Leu
    50                  55                  60
```

```
Arg Asp Arg Val Thr Leu Thr Arg Asp Thr Ser Ile Asn Thr Ala Tyr
65                  70                  75                  80

Met Glu Leu Ser Arg Leu Arg Ser Asp Asp Thr Ala Leu Tyr Tyr Cys
                85                  90                  95

Ala Thr Leu Tyr Gly Asp Tyr Arg Pro Ile Gln Asp Ser Trp Gly Gln
            100                 105                 110

Gly Thr Leu Val Thr Val Ser Ser
        115                 120

<210> SEQ ID NO 20
<211> LENGTH: 118
<212> TYPE: PRT
<213> ORGANISM: Artificial Sequence
<220> FEATURE:
<223> OTHER INFORMATION: D9 HB

<400> SEQUENCE: 20

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Ser Tyr
            20                  25                  30

Trp Met Asn Trp Val Arg Gln Ala Pro Gly Gln Gly Leu Glu Trp Ile
        35                  40                  45

Gly Arg Ile Asp Pro Tyr Asp Ser Glu Ile Gln Tyr Asn Gln Lys Phe
    50                  55                  60

Lys Asp Lys Ala Ile Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Phe Asp Trp Phe Ala Tyr Trp Gly Gln Gly Thr
            100                 105                 110

Leu Val Thr Val Ser Ser
        115

<210> SEQ ID NO 21
<211> LENGTH: 118
<212> TYPE: PRT
<213> ORGANISM: Artificial Sequence
<220> FEATURE:
<223> OTHER INFORMATION: D9 HC

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Ser Tyr
            20                  25                  30

Trp Met Asn Trp Val Arg Gln Ala Pro Gly Gln Gly Leu Glu Trp Ile
        35                  40                  45

Gly Arg Ile Asp Pro Tyr Asp Ser Glu Ile Gln Tyr Asn Gln Lys Phe
    50                  55                  60

Lys Asp Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Thr Ser Gly Gly Phe Asp Trp Phe Ala Tyr Trp Gly Gln Gly Thr
            100                 105                 110

Leu Val Thr Val Ser Ser
        115

<210> SEQ ID NO 22
<211> LENGTH: 118
<212> TYPE: PRT
<213> ORGANISM: Artificial Sequence
<220> FEATURE:
<223> OTHER INFORMATION: D9 HD

<400> SEQUENCE: 22

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Ile Gln Tyr Asn Gln Lys Phe
    50                  55                  60

Lys Asp Lys Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Thr Ser Gly Gly Phe Asp Trp Phe Ala Tyr Trp Gly Gln Gly Thr
            100                 105                 110

Leu Val Thr Val Ser Ser
        115

<210> SEQ ID NO 23
<211> LENGTH: 118
<212> TYPE: PRT
<213> ORGANISM: Artificial Sequence
<220> FEATURE:
<223> OTHER INFORMATION: D9 HE

<400> SEQUENCE: 23

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Ile Gln Tyr Asn Gln Lys Phe
    50                  55                  60

Lys Asp Arg Ala Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Thr Ser Gly Gly Phe Asp Trp Phe Ala Tyr Trp Gly Gln Gly Thr
            100                 105                 110

Leu Val Thr Val Ser Ser
        115

<210> SEQ ID NO 24
<211> LENGTH: 118
<212> TYPE: PRT
```

-continued

```
<213> ORGANISM: Artificial Sequence
<220> FEATURE:
<223> OTHER INFORMATION: D9 HF

<400> SEQUENCE: 24

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Ser Tyr
                20                  25                  30

Trp Met Asn Trp Val Arg Gln Ala Pro Gly Gln Gly Leu Glu Trp Met
            35                  40                  45

Gly Arg Ile Asp Pro Tyr Asp Ser Glu Ile Gln Tyr Asn Gln Lys Phe
        50                  55                  60

Lys Asp Arg Val Ile Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Thr Ser Gly Gly Phe Asp Trp Phe Ala Tyr Trp Gly Gln Gly Thr
            100                 105                 110

Leu Val Thr Val Ser Ser
        115

<210> SEQ ID NO 25
<211> LENGTH: 118
<212> TYPE: PRT
<213> ORGANISM: Artificial Sequence
<220> FEATURE:
<223> OTHER INFORMATION: D9 HG

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Ser Tyr
                20                  25                  30

Trp Met Asn Trp Val Arg Gln Ala Pro Gly Gln Gly Leu Glu Trp Met
            35                  40                  45

Gly Arg Ile Asp Pro Tyr Asp Ser Glu Ile Gln Tyr Asn Gln Lys Phe
        50                  55                  60

Lys Asp Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Thr Ser Gly Gly Phe Asp Trp Phe Ala Tyr Trp Gly Gln Gly Thr
            100                 105                 110

Leu Val Thr Val Ser Ser
        115

<210> SEQ ID NO 26
<211> LENGTH: 107
<212> TYPE: PRT
<213> ORGANISM: Artificial Sequence
<220> FEATURE:
<223> OTHER INFORMATION: D9.2 VK

<400> SEQUENCE: 26

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Asn Ser Asn
                20                  25                  30
```

```
Leu Ala Trp Tyr Gln Gln Lys Gly Lys Ser Pro Gln Leu Leu Val
        35                  40                  45

Tyr Asp Val Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Arg Pro Pro Tyr
                85                  90                  95

Thr Phe Gly Gly Gly Thr Asn Leu Glu Ile Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: Y14869

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gly Gly Thr Lys Val Glu Ile Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: D9_KB

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Asn Ser Asn
            20                  25                  30

Leu Ala Trp Tyr Gln Gln Lys Pro Gly Lys Ala Pro Lys Leu Leu Val
        35                  40                  45

Tyr Asp Val Thr Asn Leu Ala Asp Gly Val Pro Ser Arg Phe Ser Gly
    50                  55                  60

Ser Gly Ser Gly Thr Gln Tyr Thr Leu Thr Ile Ser Ser Leu Gln Pro
65                  70                  75                  80

Glu Asp Phe Ala Thr Tyr Tyr Cys Gln His Phe Trp Arg Pro Pro Tyr
                85                  90                  95

Thr Phe Gly Gly Gly Thr Lys Val Glu Ile Lys
            100                 105
```

```
<210> SEQ ID NO 29
<211> LENGTH: 107
<212> TYPE: PRT
<213> ORGANISM: Artificial Sequence
<220> FEATURE:
<223> OTHER INFORMATION: D9_KC

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Asn Ser Asn
            20                  25                  30

Leu Ala Trp Tyr Gln Gln Lys Pro Gly Lys Ala Pro Lys Leu Leu Val
        35                  40                  45

Tyr Asp Val Thr Asn Leu Ala Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Arg Pro Pro Tyr
                85                  90                  95

Thr Phe Gly Gly Gly Thr Lys Val Glu Ile Lys
            100                 105

<210> SEQ ID NO 30
<211> LENGTH: 107
<212> TYPE: PRT
<213> ORGANISM: Artificial Sequence
<220> FEATURE:
<223> OTHER INFORMATION: D9_KD

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Asn Ser Asn
            20                  25                  30

Leu Ala Trp Tyr Gln Gln Lys Pro Gly Lys Ala Pro Lys Leu Leu Leu
        35                  40                  45

Tyr Asp Val Thr Asn Leu Ala Asp Gly Val Pro Ser Arg Phe Ser Gly
50                  55                  60

Ser Gly Ser Gly Thr Gln Tyr Thr Leu Thr Ile Ser Ser Leu Gln Pro
65                  70                  75                  80

Glu Asp Phe Ala Thr Tyr Tyr Cys Gln His Phe Trp Arg Pro Pro Tyr
                85                  90                  95

Thr Phe Gly Gly Gly Thr Lys Val Glu Ile Lys
            100                 105

<210> SEQ ID NO 31
<211> LENGTH: 107
<212> TYPE: PRT
<213> ORGANISM: Artificial Sequence
<220> FEATURE:
<223> OTHER INFORMATION: KM

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Asn
            20                  25                  30

Leu Ala Trp Tyr Gln Gln Lys Pro Gly Lys Ala Pro Lys Leu Leu Leu
        35                  40                  45
```

-continued

```
Tyr Asp Ala Thr Asn Leu Gly Asp Gly Val Pro Ser Arg Phe Ser Gly
         50              55              60

Ser Gly Ser Gly Thr Asp Tyr Thr Leu Thr Ile Ser Ser Leu Gln Pro
 65              70              75              80

Glu Asp Phe Ala Thr Tyr Tyr Cys Gln His Phe Trp Gly Pro Pro Tyr
             85              90              95

Thr Phe Gly Gly Gly Thr Lys Val Glu Ile Lys
             100             105
```